(12) United States Patent
Jenkins et al.

(10) Patent No.: US 8,768,433 B2
(45) Date of Patent: *Jul. 1, 2014

(54) MRI-GUIDED DEVICES AND MRI-GUIDED INTERVENTIONAL SYSTEMS THAT CAN TRACK AND GENERATE DYNAMIC VISUALIZATIONS OF THE DEVICES IN NEAR REAL TIME

(71) Applicant: MRI Interventions, Inc., Memphis, TN (US)

(72) Inventors: Kimble L. Jenkins, Memphis, TN (US); Peter Piferi, Orange, CA (US); Kamal Vij, Chandler, AZ (US)

(73) Assignee: MRI Interventions, Inc., Memphis, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/723,612

(22) Filed: Dec. 21, 2012

(65) Prior Publication Data

US 2013/0116543 A1 May 9, 2013

Related U.S. Application Data

(63) Continuation of application No. 12/816,757, filed on Jun. 16, 2010, now Pat. No. 8,396,532.

(60) Provisional application No. 61/187,323, filed on Jun. 16, 2009, provisional application No. 61/219,638, filed on Jun. 23, 2009, provisional application No. 61/261,103, filed on Nov. 13, 2009.

(51) Int. Cl.
*A61B 5/05* (2006.01)

(52) U.S. Cl.
USPC ........................... 600/423; 600/410; 600/424

(58) Field of Classification Search
USPC .......... 600/407–429, 473–480; 607/119–123; 324/307, 309, 318
See application file for complete search history.

(56) References Cited

U.S. PATENT DOCUMENTS

| 3,499,435 A | 3/1970 | Rockwell et al. |
| 3,661,158 A | 5/1972 | Berkovits |

(Continued)

FOREIGN PATENT DOCUMENTS

| EP | 0466424 | 1/1992 |
| EP | 0498996 | 8/1992 |

(Continued)

OTHER PUBLICATIONS

Ackerman et al., "Rapid 3D Tracking of Small RF Coils [abstract]," Proceedings of the 5th Annual Meeting of ISMRM, Montreal, Canada pp. 1131-1132 (1986).

(Continued)

*Primary Examiner* — Sanjay Cattungal
(74) *Attorney, Agent, or Firm* — Myers Bigel Sibley & Sajovec, P.A.

(57) ABSTRACT

An MRI-guided medical device includes an elongated sheath, an elongated dilator, and an elongated needle. The sheath has a distal end, an opposite proximal end, and a central lumen extending between the proximal and distal ends. The sheath comprises MRI-compatible material and includes a tracking member located adjacent to the sheath distal end that is visible in an MRI image. The dilator comprises MRI-compatible material and is movably disposed within the sheath lumen. A distal end of the dilator is configured to extend outwardly from the sheath distal end and dilator includes at least one tracking member that is visible in an MRI image. The needle is movably disposed within the dilator lumen and is movable between stored and operative positions relative to the dilator. An RF shield may be coaxially disposed within the elongated sheath so as to surround a portion of the sheath central lumen.

19 Claims, 29 Drawing Sheets

(56) References Cited

U.S. PATENT DOCUMENTS

| | | |
|---|---|---|
| 4,295,467 A | 10/1981 | Mann et al. |
| 4,431,005 A | 2/1984 | McCormick |
| 4,445,501 A | 5/1984 | Bresler |
| 4,572,198 A | 2/1986 | Codrington |
| 4,612,930 A | 9/1986 | Bremer |
| 4,639,365 A | 1/1987 | Sherry |
| 4,643,186 A | 2/1987 | Rosen et al. |
| 4,672,972 A | 6/1987 | Berke |
| 4,752,198 A | 6/1988 | Boschman |
| 4,754,752 A | 7/1988 | Ginsburg et al. |
| 4,757,820 A | 7/1988 | Itoh |
| 4,766,381 A | 8/1988 | Conturo et al. |
| 4,791,934 A | 12/1988 | Brunnett |
| 4,793,359 A | 12/1988 | Sharrow |
| 4,813,429 A | 3/1989 | Eshel et al. |
| 4,823,812 A | 4/1989 | Eshel et al. |
| 4,832,023 A | 5/1989 | Murphy-Chutorian et al. |
| 4,859,950 A | 8/1989 | Keren |
| 4,932,411 A | 6/1990 | Fritschy et al. |
| 4,951,672 A | 8/1990 | Buchwald et al. |
| 4,960,106 A | 10/1990 | Kubokawa et al. |
| 4,989,608 A | 2/1991 | Ratner |
| 4,991,580 A | 2/1991 | Moore |
| 5,019,075 A | 5/1991 | Spears et al. |
| 5,078,140 A | 1/1992 | Kwoh |
| 5,095,911 A | 3/1992 | Pomeranz |
| 5,099,208 A | 3/1992 | Fitzpatrick et al. |
| 5,125,896 A | 6/1992 | Hojeibane |
| 5,151,856 A | 9/1992 | Halmann et al. |
| 5,154,179 A | 10/1992 | Ratner |
| 5,156,151 A | 10/1992 | Imran |
| 5,167,233 A | 12/1992 | Eberle et al. |
| 5,170,789 A | 12/1992 | Narayan et al. |
| 5,178,618 A | 1/1993 | Kandarpa |
| 5,190,046 A | 3/1993 | Shturman |
| 5,190,528 A | 3/1993 | Fonger et al. |
| 5,209,233 A | 5/1993 | Holland et al. |
| 5,211,165 A | 5/1993 | Dumoulin et al. |
| 5,217,010 A | 6/1993 | Tsitlik et al. |
| 5,218,025 A | 6/1993 | Kurimoto et al. |
| 5,230,338 A | 7/1993 | Allen et al. |
| 5,246,438 A | 9/1993 | Langberg |
| 5,251,120 A | 10/1993 | Smith |
| 5,251,635 A | 10/1993 | Dumoulin et al. |
| 5,255,680 A | 10/1993 | Darrow et al. |
| 5,263,485 A | 11/1993 | Hickey |
| 5,271,400 A | 12/1993 | Dumoulin et al. |
| 5,275,163 A | 1/1994 | McKimmon et al. |
| 5,276,927 A | 1/1994 | Day |
| 5,284,144 A | 2/1994 | Delannoy et al. |
| 5,290,266 A | 3/1994 | Rohling et al. |
| 5,293,868 A | 3/1994 | Nardella |
| 5,297,549 A | 3/1994 | Beatty et al. |
| 5,307,808 A | 5/1994 | Dumoulin et al. |
| 5,307,814 A | 5/1994 | Kressel et al. |
| 5,318,025 A | 6/1994 | Dumoulin et al. |
| 5,323,776 A | 6/1994 | Blakeley et al. |
| 5,323,778 A | 6/1994 | Kandarpa |
| 5,347,221 A | 9/1994 | Rubinson |
| 5,348,010 A | 9/1994 | Schnall et al. |
| 5,352,979 A | 10/1994 | Conturo |
| 5,353,795 A | 10/1994 | Souza et al. |
| 5,355,087 A | 10/1994 | Clairone et al. |
| 5,358,515 A | 10/1994 | Hurter et al. |
| 5,362,475 A | 11/1994 | Gries et al. |
| 5,365,928 A | 11/1994 | Rhinehart et al. |
| 5,370,644 A | 12/1994 | Langberg |
| 5,377,678 A | 1/1995 | Dumoulin et al. |
| 5,383,454 A | 1/1995 | Bucholz |
| 5,384,537 A | 1/1995 | Ito et al. |
| 5,389,101 A | 2/1995 | Heilbrun et al. |
| 5,391,199 A | 2/1995 | Ben-Haim |
| 5,394,873 A | 3/1995 | Kraemer et al. |
| 5,398,683 A | 3/1995 | Edwards et al. |
| 5,398,692 A | 3/1995 | Hickey |
| 5,405,346 A | 4/1995 | Grundy et al. |
| 5,409,008 A | 4/1995 | Svenson et al. |
| 5,413,104 A | 5/1995 | Buijs et al. |
| 5,415,163 A | 5/1995 | Harms et al. |
| 5,422,576 A | 6/1995 | Kao et al. |
| 5,433,198 A | 7/1995 | Desai |
| 5,433,717 A | 7/1995 | Rubinsky et al. |
| 5,436,564 A | 7/1995 | Kreger et al. |
| 5,437,277 A | 8/1995 | Dumoulin et al. |
| 5,443,066 A | 8/1995 | Dumoulin et al. |
| 5,443,489 A | 8/1995 | Ben-Haim |
| 5,447,156 A | 9/1995 | Dumoulin et al. |
| 5,462,055 A | 10/1995 | Casey et al. |
| 5,480,422 A | 1/1996 | Ben-Haim |
| 5,507,743 A | 4/1996 | Edwards et al. |
| 5,512,825 A | 4/1996 | Atalar et al. |
| 5,529,068 A | 6/1996 | Hoenninger, III et al. |
| 5,531,227 A | 7/1996 | Schneider |
| 5,546,940 A | 8/1996 | Panescu et al. |
| 5,546,951 A | 8/1996 | Ben-Haim |
| 5,558,093 A | 9/1996 | Pomeranz |
| 5,568,809 A | 10/1996 | Ben-Haim |
| 5,569,266 A | 10/1996 | Siczek |
| 5,577,502 A | 11/1996 | Darrow et al. |
| 5,588,432 A | 12/1996 | Crowley |
| 5,590,657 A | 1/1997 | Cain et al. |
| 5,617,026 A | 4/1997 | Yoshino et al. |
| 5,622,170 A | 4/1997 | Schulz |
| 5,634,467 A | 6/1997 | Nevo |
| 5,643,255 A | 7/1997 | Organ |
| 5,644,234 A | 7/1997 | Rasche et al. |
| 5,647,361 A | 7/1997 | Damadian |
| 5,657,755 A | 8/1997 | Desai |
| 5,662,108 A | 9/1997 | Budd et al. |
| 5,671,739 A | 9/1997 | Darrow et al. |
| 5,682,886 A | 11/1997 | Delp et al. |
| 5,682,897 A | 11/1997 | Pomeranz |
| 5,685,878 A | 11/1997 | Falwell et al. |
| 5,687,725 A | 11/1997 | Wendt |
| 5,694,945 A | 12/1997 | Ben-Haim |
| 5,699,801 A | 12/1997 | Atalar et al. |
| 5,706,823 A | 1/1998 | Wodlinger |
| 5,713,357 A | 2/1998 | Meulenbrugge et al. |
| 5,713,946 A | 2/1998 | Ben-Haim |
| 5,715,822 A | 2/1998 | Watkins et al. |
| 5,722,402 A | 3/1998 | Swanson et al. |
| 5,728,079 A | 3/1998 | Weber et al. |
| 5,738,096 A | 4/1998 | Ben-Haim |
| 5,739,691 A | 4/1998 | Hoenninger, III |
| 5,740,808 A | 4/1998 | Panescu et al. |
| 5,744,958 A | 4/1998 | Werne |
| 5,749,835 A | 5/1998 | Glantz |
| 5,754,085 A | 5/1998 | Danby et al. |
| 5,769,846 A | 6/1998 | Edwards et al. |
| 5,782,764 A | 7/1998 | Werne |
| 5,792,055 A | 8/1998 | McKinnon |
| 5,797,849 A | 8/1998 | Vesely et al. |
| 5,800,352 A | 9/1998 | Ferre et al. |
| 5,810,728 A | 9/1998 | Kuhn |
| 5,817,130 A | 10/1998 | Cox et al. |
| 5,820,580 A | 10/1998 | Edwards et al. |
| 5,833,608 A | 11/1998 | Acker |
| 5,836,874 A | 11/1998 | Swanson et al. |
| 5,840,025 A | 11/1998 | Ben-Haim |
| 5,840,031 A | 11/1998 | Crowley |
| 5,864,234 A | 1/1999 | Ludeke |
| 5,868,674 A | 2/1999 | Glowinski et al. |
| 5,882,304 A | 3/1999 | Ehnholm et al. |
| 5,891,047 A | 4/1999 | Lander et al. |
| 5,908,445 A | 6/1999 | Whayne et al. |
| 5,916,162 A | 6/1999 | Snelton et al. |
| 5,928,145 A | 7/1999 | Ocali et al. |
| 5,938,599 A | 8/1999 | Rasche et al. |
| 5,938,609 A | 8/1999 | Pomeranz |
| 5,944,022 A | 8/1999 | Nardella et al. |
| 5,951,472 A | 9/1999 | Van Vaals et al. |
| 5,961,528 A | 10/1999 | Birk et al. |
| 5,964,705 A | 10/1999 | Truwit et al. |
| 5,964,753 A | 10/1999 | Edwards |

(56) References Cited

U.S. PATENT DOCUMENTS

| | | |
|---|---|---|
| 5,978,696 A | 11/1999 | VomLehn et al. |
| 6,004,269 A | 12/1999 | Crowley et al. |
| 6,014,579 A | 1/2000 | Pomeranz et al. |
| 6,014,581 A | 1/2000 | Whayne et al. |
| 6,019,725 A | 2/2000 | Vesely et al. |
| 6,023,165 A | 2/2000 | Damadian et al. |
| 6,023,636 A | 2/2000 | Wendt et al. |
| 6,026,316 A | 2/2000 | Kucharczyk et al. |
| 6,027,500 A | 2/2000 | Buckles et al. |
| 6,031,375 A | 2/2000 | Atalar et al. |
| 6,045,532 A | 4/2000 | Eggers et al. |
| 6,045,553 A | 4/2000 | Iversen et al. |
| 6,052,614 A | 4/2000 | Morris, Sr. et al. |
| 6,052,618 A | 4/2000 | Dahlke et al. |
| 6,066,136 A | 5/2000 | Geistert |
| 6,067,371 A | 5/2000 | Gouge et al. |
| 6,070,094 A | 5/2000 | Swanson et al. |
| 6,071,281 A | 6/2000 | Burnside et al. |
| 6,073,039 A | 6/2000 | Berson |
| 6,076,007 A | 6/2000 | England et al. |
| 6,095,150 A | 8/2000 | Panescu et al. |
| 6,119,032 A | 9/2000 | Martin et al. |
| 6,128,522 A | 10/2000 | Acker et al. |
| 6,129,670 A | 10/2000 | Burdette et al. |
| 6,167,296 A | 12/2000 | Shahidi |
| 6,171,240 B1 | 1/2001 | Young et al. |
| 6,171,241 B1 | 1/2001 | McVeigh et al. |
| 6,179,833 B1 | 1/2001 | Taylor |
| 6,188,219 B1 | 2/2001 | Reeder et al. |
| 6,190,353 B1 | 2/2001 | Makower et al. |
| 6,192,144 B1 | 2/2001 | Holz |
| 6,201,394 B1 | 3/2001 | Danby et al. |
| 6,216,029 B1 | 4/2001 | Paltieli |
| 6,224,553 B1 | 5/2001 | Nevo |
| 6,226,542 B1 | 5/2001 | Reisfeld |
| 6,226,545 B1 | 5/2001 | Gilderdale |
| 6,231,570 B1 | 5/2001 | Tu et al. |
| 6,233,474 B1 | 5/2001 | Lemelson |
| 6,234,970 B1 | 5/2001 | Nevo et al. |
| 6,236,205 B1 | 5/2001 | Lüdeke et al. |
| 6,238,390 B1 | 5/2001 | Tu et al. |
| 6,241,725 B1 | 6/2001 | Cosman |
| 6,246,896 B1 | 6/2001 | Dumoulin et al. |
| 6,256,529 B1 | 7/2001 | Holupka et al. |
| 6,263,229 B1 | 7/2001 | Atalar et al. |
| 6,272,370 B1 | 8/2001 | Gillies et al. |
| 6,272,371 B1 | 8/2001 | Shlomo |
| 6,280,385 B1 | 8/2001 | Melzer et al. |
| 6,284,970 B1 | 9/2001 | Buskmiller et al. |
| 6,284,971 B1 | 9/2001 | Atalar et al. |
| 6,289,233 B1 | 9/2001 | Dumoulin et al. |
| 6,301,496 B1 | 10/2001 | Reisfeld |
| 6,317,619 B1 | 11/2001 | Boernert et al. |
| 6,322,558 B1 | 11/2001 | Taylor et al. |
| 6,332,089 B1 | 12/2001 | Acker et al. |
| 6,368,285 B1 | 4/2002 | Osadchy et al. |
| 6,370,434 B1 | 4/2002 | Zhang et al. |
| 6,375,606 B1 | 4/2002 | Garibaldi et al. |
| 6,385,472 B1 | 5/2002 | Hall et al. |
| 6,385,476 B1 | 5/2002 | Osadchy et al. |
| 6,393,314 B1 | 5/2002 | Watkins et al. |
| 6,408,202 B1 | 6/2002 | Lima et al. |
| 6,422,748 B1 | 7/2002 | Shepherd et al. |
| 6,428,537 B1 | 8/2002 | Swanson et al. |
| 6,430,429 B1 | 8/2002 | Van Vaals |
| 6,431,173 B1 | 8/2002 | Hoffmann |
| 6,456,867 B2 | 9/2002 | Reisfeld |
| 6,470,204 B1 | 10/2002 | Uzgiris et al. |
| 6,475,223 B1 | 11/2002 | Werp et al. |
| 6,487,431 B1 | 11/2002 | Iwano et al. |
| 6,487,437 B1 | 11/2002 | Viswanathan et al. |
| 6,490,473 B1 | 12/2002 | Katznelson et al. |
| 6,506,189 B1 | 1/2003 | Rittman, II et al. |
| 6,516,213 B1 | 2/2003 | Nevo |
| 6,522,913 B2 | 2/2003 | Swanson et al. |
| 6,529,758 B2 | 3/2003 | Shahidi |
| 6,529,764 B1 | 3/2003 | Kato et al. |
| 6,534,982 B1 | 3/2003 | Jakab |
| 6,535,755 B2 | 3/2003 | Ehnholm |
| 6,546,273 B2 | 4/2003 | Suzuki et al. |
| 6,546,279 B1 | 4/2003 | Bova et al. |
| 6,549,800 B1 | 4/2003 | Atalar et al. |
| 6,556,009 B2 | 4/2003 | Kellman et al. |
| 6,556,695 B1 | 4/2003 | Packer et al. |
| 6,558,333 B2 | 5/2003 | Gilboa et al. |
| 6,558,382 B2 | 5/2003 | Jahns et al. |
| 6,575,969 B1 | 6/2003 | Rittman, II et al. |
| 6,591,128 B1 | 7/2003 | Wu et al. |
| 6,591,130 B2 | 7/2003 | Shahidi |
| 6,593,884 B1 | 7/2003 | Gilboa et al. |
| 6,594,517 B1 | 7/2003 | Nevo |
| 6,597,935 B2 | 7/2003 | Prince et al. |
| 6,600,319 B2 | 7/2003 | Golan |
| 6,603,997 B2 | 8/2003 | Doody |
| 6,606,513 B2 | 8/2003 | Lardo et al. |
| 6,626,902 B1 | 9/2003 | Kucharczyk et al. |
| 6,628,980 B2 | 9/2003 | Atalar et al. |
| 6,633,773 B1 | 10/2003 | Reisfeld |
| 6,640,126 B2 | 10/2003 | Chang |
| 6,643,535 B2 | 11/2003 | Eum et al. |
| 6,650,923 B1 | 11/2003 | Lesh et al. |
| 6,650,927 B1 | 11/2003 | Keidar |
| 6,654,628 B1 | 11/2003 | Silber et al. |
| 6,668,184 B1 | 12/2003 | Kleiman |
| 6,675,033 B1 | 1/2004 | Lardo et al. |
| 6,675,037 B1 | 1/2004 | Tsekos |
| 6,687,530 B2 | 2/2004 | Dumoulin |
| 6,690,963 B2 | 2/2004 | Ben-Haim et al. |
| 6,701,176 B1 | 3/2004 | Halperin et al. |
| 6,702,835 B2 | 3/2004 | Ginn |
| 6,711,429 B1 | 3/2004 | Gilboa et al. |
| 6,714,809 B2 | 3/2004 | Lee et al. |
| 6,725,079 B2 * | 4/2004 | Zuk et al. .................. 600/414 |
| 6,740,883 B1 | 5/2004 | Stodilka et al. |
| 6,741,879 B2 | 5/2004 | Chang |
| 6,741,882 B2 | 5/2004 | Schäffter et al. |
| 6,743,248 B2 | 6/2004 | Edwards et al. |
| 6,771,067 B2 | 8/2004 | Kellman et al. |
| 6,780,183 B2 | 8/2004 | Jimenez, Jr. et al. |
| 6,785,572 B2 | 8/2004 | Yanof et al. |
| 6,788,062 B2 | 9/2004 | Schweikard et al. |
| 6,788,967 B2 | 9/2004 | Ben-Haim et al. |
| 6,793,664 B2 | 9/2004 | Mazzocchi et al. |
| 6,794,872 B2 | 9/2004 | Meyer et al. |
| 6,813,512 B2 | 11/2004 | Aldefeld et al. |
| 6,829,509 B1 | 12/2004 | MacDonald et al. |
| 6,847,210 B1 | 1/2005 | Eydelman et al. |
| 6,847,837 B1 | 1/2005 | Melzer et al. |
| 6,853,856 B2 | 2/2005 | Yanof et al. |
| 6,871,086 B2 | 3/2005 | Nevo et al. |
| 6,879,160 B2 | 4/2005 | Jakab |
| 6,892,090 B2 | 5/2005 | Verard et al. |
| 6,892,091 B1 | 5/2005 | Ben-Haim et al. |
| 6,896,678 B2 | 5/2005 | Tweardy |
| 6,898,302 B1 | 5/2005 | Brummer |
| 6,898,454 B2 | 5/2005 | Atalar et al. |
| 6,904,307 B2 * | 6/2005 | Karmarkar et al. ........... 600/423 |
| 6,920,347 B2 | 7/2005 | Simon et al. |
| 6,941,166 B2 | 9/2005 | MacAdam et al. |
| 6,949,929 B2 | 9/2005 | Gray et al. |
| 6,950,543 B2 | 9/2005 | King et al. |
| 6,958,035 B2 | 10/2005 | Friedman et al. |
| 6,961,602 B2 | 11/2005 | Fuimaono et al. |
| 6,961,608 B2 * | 11/2005 | Hoshino et al. ............. 600/423 |
| 6,975,896 B2 | 12/2005 | Ehnholm et al. |
| 6,980,865 B1 | 12/2005 | Wang et al. |
| 6,985,775 B2 | 1/2006 | Reinke et al. |
| 6,988,001 B2 | 1/2006 | Greatbatch et al. |
| 6,994,094 B2 | 2/2006 | Schwartz |
| 6,996,430 B1 | 2/2006 | Gilboa et al. |
| 7,001,383 B2 | 2/2006 | Keidar |
| 7,011,647 B2 * | 3/2006 | Purdy et al. ............. 604/164.04 |
| 7,020,312 B2 | 3/2006 | Desmedt et al. |
| 7,027,851 B2 | 4/2006 | Mejia |

(56) References Cited

U.S. PATENT DOCUMENTS

| | | |
|---|---|---|
| 7,027,854 B2 | 4/2006 | Fuderer et al. |
| 7,047,060 B1 | 5/2006 | Wu |
| 7,048,716 B1 | 5/2006 | Kucharczyk et al. |
| 7,056,294 B2 | 6/2006 | Khairkhahan et al. |
| 7,081,748 B2 | 7/2006 | Jakab |
| 7,082,325 B2 | 7/2006 | Hashimshony et al. |
| 7,089,045 B2 | 8/2006 | Fuimaono et al. |
| 7,095,890 B2 | 8/2006 | Paragios et al. |
| 7,096,057 B2 | 8/2006 | Hockett et al. |
| 7,099,712 B2 | 8/2006 | Fuimaono et al. |
| 7,123,013 B2 | 10/2006 | Gray |
| 7,133,714 B2 | 11/2006 | Karmarkar et al. |
| 7,134,438 B2 | 11/2006 | Makower et al. |
| 7,154,498 B2 | 12/2006 | Cowan et al. |
| 7,155,271 B2 | 12/2006 | Halperin et al. |
| 7,162,293 B2 | 1/2007 | Weiss |
| 7,187,964 B2 | 3/2007 | Khoury |
| 7,204,840 B2 | 4/2007 | Skakoon |
| 7,205,768 B2 | 4/2007 | Schulz et al. |
| 7,209,777 B2 | 4/2007 | Saranathan |
| 7,211,082 B2 | 5/2007 | Hall et al |
| 7,220,265 B2 | 5/2007 | Chanduszko et al. |
| 7,225,012 B1 | 5/2007 | Susil et al. |
| 7,228,164 B2 | 6/2007 | Fuimaono et al. |
| 7,236,816 B2 * | 6/2007 | Kumar et al. ............... 600/411 |
| 7,239,400 B2 | 7/2007 | Bock |
| 7,241,283 B2 | 7/2007 | Putz |
| 7,255,691 B2 | 8/2007 | Tolkoff et al. |
| 7,263,397 B2 | 8/2007 | Hauck et al. |
| 7,276,905 B2 | 10/2007 | Tamaroff et al. |
| 7,280,863 B2 | 10/2007 | Shachar |
| 7,285,119 B2 | 10/2007 | Stewart |
| 7,289,843 B2 | 10/2007 | Beatty et al. |
| 7,302,285 B2 | 11/2007 | Fuimaono et al. |
| 7,306,593 B2 | 12/2007 | Keidar et al. |
| 7,307,420 B2 | 12/2007 | Dumoulin |
| 7,308,299 B2 | 12/2007 | Burrell et al. |
| 7,311,705 B2 | 12/2007 | Sra |
| 7,320,695 B2 | 1/2008 | Carroll |
| 7,343,195 B2 | 3/2008 | Strommer et al. |
| 7,347,829 B2 | 3/2008 | Mark et al. |
| 7,363,090 B2 | 4/2008 | Halperin et al. |
| 7,386,339 B2 | 6/2008 | Strommer et al. |
| 7,398,116 B2 | 7/2008 | Edwards |
| 7,412,276 B2 | 8/2008 | Halperin et al. |
| 7,415,301 B2 | 8/2008 | Hareyama et al. |
| 7,418,289 B2 | 8/2008 | Hyde et al. |
| 7,422,568 B2 | 9/2008 | Yang et al. |
| 7,440,792 B2 | 10/2008 | Eggers |
| 7,463,920 B2 | 12/2008 | Purdy |
| 7,473,843 B2 | 1/2009 | Wang et al. |
| 7,474,913 B2 | 1/2009 | Durlak |
| 7,477,054 B2 | 1/2009 | Hoogenraad et al. |
| 7,480,398 B2 | 1/2009 | Kleen et al. |
| 7,483,732 B2 | 1/2009 | Zhong et al. |
| 7,495,438 B2 | 2/2009 | Prince et al. |
| 7,499,743 B2 | 3/2009 | Vass et al. |
| 7,505,808 B2 | 3/2009 | Anderson et al. |
| 7,505,809 B2 | 3/2009 | Strommer et al. |
| 7,505,810 B2 | 3/2009 | Harlev et al. |
| 7,542,793 B2 | 6/2009 | Wu et al. |
| 7,551,953 B2 | 6/2009 | Lardo et al. |
| 7,561,906 B2 | 7/2009 | Atalar et al. |
| 7,587,234 B2 | 9/2009 | Owens et al. |
| 7,593,558 B2 | 9/2009 | Boese |
| 7,599,730 B2 | 10/2009 | Hunter et al. |
| 7,602,190 B2 | 10/2009 | Piferi et al. |
| 7,606,611 B2 | 10/2009 | Speier |
| 7,609,862 B2 | 10/2009 | Black |
| 7,623,903 B2 | 11/2009 | Wacker |
| 7,632,265 B2 | 12/2009 | Hauck et al. |
| 7,660,623 B2 | 2/2010 | Hunter et al. |
| 7,689,264 B2 | 3/2010 | Nauerth |
| 7,697,972 B2 | 4/2010 | Verard et al. |
| 7,720,520 B2 | 5/2010 | Willis |
| 7,725,157 B2 | 5/2010 | Dumoulin et al. |
| 7,725,160 B2 | 5/2010 | Weber |
| 7,725,161 B2 | 5/2010 | Karmarkar et al. |
| 7,726,708 B2 | 6/2010 | Bourrieres |
| 7,751,865 B2 | 7/2010 | Jascob et al. |
| 7,769,427 B2 | 8/2010 | Shachar |
| 7,777,485 B2 * | 8/2010 | Dumoulin et al. ............ 324/309 |
| 7,787,935 B2 | 8/2010 | Dumoulin et al. |
| 7,811,294 B2 | 10/2010 | Strommer et al. |
| 7,815,623 B2 | 10/2010 | Bankiewicz |
| 7,822,460 B2 | 10/2010 | Halperin et al. |
| 7,840,253 B2 * | 11/2010 | Tremblay et al. ............ 600/424 |
| 7,841,986 B2 | 11/2010 | He |
| 7,844,320 B2 | 11/2010 | Shahidi |
| 7,853,332 B2 | 12/2010 | Olsen |
| 7,881,769 B2 | 2/2011 | Sobe |
| 7,894,877 B2 | 2/2011 | Lewin et al. |
| 7,920,911 B2 * | 4/2011 | Hoshino et al. ............... 600/423 |
| 7,999,547 B2 | 8/2011 | Green et al. |
| 8,010,177 B2 | 8/2011 | Csavoy et al. |
| 8,016,857 B2 * | 9/2011 | Sater et al. .................... 606/213 |
| 8,221,442 B2 * | 7/2012 | Domb et al. .................. 606/192 |
| 8,521,257 B2 * | 8/2013 | Whitcomb et al. ........... 600/411 |
| 8,532,742 B2 | 9/2013 | Unal et al. |
| 2001/0025142 A1 | 9/2001 | Wessels et al. |
| 2002/0019629 A1 | 2/2002 | Dietz et al. |
| 2002/0019644 A1 | 2/2002 | Hastings et al. |
| 2002/0055678 A1 | 5/2002 | Scott et al. |
| 2002/0058868 A1 * | 5/2002 | Hoshino et al. ............... 600/423 |
| 2002/0072712 A1 * | 6/2002 | Nool et al. ................. 604/167.01 |
| 2002/0103430 A1 | 8/2002 | Hastings et al. |
| 2002/0169371 A1 | 11/2002 | Gilderdale |
| 2002/0177771 A1 | 11/2002 | Guttman et al. |
| 2003/0028095 A1 | 2/2003 | Tulley et al. |
| 2003/0050557 A1 | 3/2003 | Susil et al. |
| 2003/0055332 A1 | 3/2003 | Daum et al. |
| 2003/0078494 A1 | 4/2003 | Panescu et al. |
| 2003/0088181 A1 | 5/2003 | Gleich et al. |
| 2003/0093067 A1 | 5/2003 | Panescu |
| 2003/0097149 A1 * | 5/2003 | Edwards et al. ............... 606/214 |
| 2003/0100829 A1 | 5/2003 | Zhong et al. |
| 2003/0130577 A1 * | 7/2003 | Purdy et al. ................... 600/433 |
| 2003/0158477 A1 | 8/2003 | Panescu |
| 2003/0208252 A1 | 11/2003 | O'Boyle et al. |
| 2003/0216642 A1 | 11/2003 | Pepin et al. |
| 2004/0006268 A1 | 1/2004 | Gilboa et al. |
| 2004/0015075 A1 * | 1/2004 | Kimchy et al. ............... 600/424 |
| 2004/0024308 A1 | 2/2004 | Wickline et al. |
| 2004/0030244 A1 | 2/2004 | Garibaldi et al. |
| 2004/0034297 A1 | 2/2004 | Darrow et al. |
| 2004/0046557 A1 | 3/2004 | Karmarkar et al. |
| 2004/0049121 A1 | 3/2004 | Yaron |
| 2004/0054279 A1 | 3/2004 | Hanley |
| 2004/0064148 A1 * | 4/2004 | Daum et al. .................. 606/130 |
| 2004/0073088 A1 | 4/2004 | Friedman et al. |
| 2004/0082948 A1 * | 4/2004 | Stewart et al. .................... 606/41 |
| 2004/0092813 A1 | 5/2004 | Takizawa et al. |
| 2004/0111022 A1 | 6/2004 | Grabek et al. |
| 2004/0116800 A1 | 6/2004 | Helfer et al. |
| 2004/0124838 A1 * | 7/2004 | Duerk et al. .................. 324/304 |
| 2004/0143180 A1 | 7/2004 | Zhong et al. |
| 2004/0152968 A1 | 8/2004 | Iversen et al. |
| 2004/0152974 A1 | 8/2004 | Solomon |
| 2004/0171934 A1 | 9/2004 | Khan et al. |
| 2004/0181160 A1 | 9/2004 | Rudy |
| 2004/0181177 A1 | 9/2004 | Lee |
| 2004/0199072 A1 | 10/2004 | Sprouse et al. |
| 2004/0220470 A1 * | 11/2004 | Karmarkar et al. ............ 600/423 |
| 2004/0225213 A1 | 11/2004 | Wang et al. |
| 2005/0010105 A1 | 1/2005 | Sra |
| 2005/0014995 A1 | 1/2005 | Amundson |
| 2005/0033164 A1 * | 2/2005 | Yatsuo et al. .................. 600/434 |
| 2005/0054910 A1 | 3/2005 | Tremblay et al. |
| 2005/0054913 A1 | 3/2005 | Duerk et al. |
| 2005/0113874 A1 | 5/2005 | Connelly |
| 2005/0119556 A1 | 6/2005 | Gillies et al. |
| 2005/0143651 A1 | 6/2005 | Verard et al. |
| 2005/0154279 A1 | 7/2005 | Li et al. |
| 2005/0154281 A1 | 7/2005 | Xue et al. |

(56) References Cited

U.S. PATENT DOCUMENTS

| | | |
|---|---|---|
| 2005/0154282 A1 | 7/2005 | Li et al. |
| 2005/0165301 A1 | 7/2005 | Smith et al. |
| 2005/0171427 A1 | 8/2005 | Nevo |
| 2005/0215886 A1 | 9/2005 | Schmidt |
| 2005/0222509 A1 | 10/2005 | Neason |
| 2005/0228252 A1 | 10/2005 | Neason |
| 2005/0256398 A1 | 11/2005 | Hastings et al. |
| 2005/0288599 A1 | 12/2005 | MacAdam et al. |
| 2006/0009756 A1 | 1/2006 | Francischelli et al. |
| 2006/0025677 A1 | 2/2006 | Verard et al. |
| 2006/0052706 A1 | 3/2006 | Hynynen |
| 2006/0084867 A1 | 4/2006 | Tremblay et al. |
| 2006/0089624 A1 | 4/2006 | Voegele et al. |
| 2006/0100506 A1 | 5/2006 | Halperin et al. |
| 2006/0106303 A1 | 5/2006 | Karmarkar et al. |
| 2006/0116576 A1 | 6/2006 | McGee |
| 2006/0184011 A1 | 8/2006 | Macaulay et al. |
| 2006/0224062 A1 | 10/2006 | Aggarwal et al. |
| 2006/0241392 A1 | 10/2006 | Feinstein |
| 2006/0247521 A1 | 11/2006 | McGee |
| 2006/0247684 A1 | 11/2006 | Halperin et al. |
| 2006/0258934 A1 | 11/2006 | Zenge et al. |
| 2007/0049817 A1 | 3/2007 | Preiss |
| 2007/0055328 A1 | 3/2007 | Mayse et al. |
| 2007/0062547 A1 | 3/2007 | Pappone |
| 2007/0073135 A1 | 3/2007 | Lee |
| 2007/0073179 A1 | 3/2007 | Afonso |
| 2007/0083195 A1 | 4/2007 | Werneth |
| 2007/0088295 A1 | 4/2007 | Bankiewicz |
| 2007/0088416 A1 | 4/2007 | Atalar et al. |
| 2007/0100223 A1 | 5/2007 | Liao et al. |
| 2007/0100232 A1 | 5/2007 | Hiller et al. |
| 2007/0106148 A1 | 5/2007 | Dumoulin |
| 2007/0112398 A1 | 5/2007 | Stevenson |
| 2007/0156042 A1 | 7/2007 | Unal et al. |
| 2007/0167726 A1 | 7/2007 | Unal et al. |
| 2007/0167736 A1 | 7/2007 | Dietz et al. |
| 2007/0167738 A1 | 7/2007 | Timinger et al. |
| 2007/0167745 A1 | 7/2007 | Case |
| 2007/0167801 A1 | 7/2007 | Webler et al. |
| 2007/0185485 A1 | 8/2007 | Hauck et al. |
| 2007/0208260 A1 | 9/2007 | Afonso |
| 2007/0233238 A1 | 10/2007 | Huynh et al. |
| 2007/0238970 A1 | 10/2007 | Kozerke et al. |
| 2007/0238978 A1 | 10/2007 | Kumar et al. |
| 2007/0238985 A1 | 10/2007 | Smith et al. |
| 2007/0249934 A1 | 10/2007 | Aksit et al. |
| 2007/0265521 A1 | 11/2007 | Redel et al. |
| 2007/0265642 A1 | 11/2007 | Chanduszko et al. |
| 2007/0270741 A1 | 11/2007 | Hassett et al. |
| 2007/0293724 A1 | 12/2007 | Saadat et al. |
| 2008/0009700 A1 | 1/2008 | Dumoulin et al. |
| 2008/0021336 A1 | 1/2008 | Dobak, III |
| 2008/0027696 A1 | 1/2008 | Pedain et al. |
| 2008/0032249 A1 | 2/2008 | Scommegna et al. |
| 2008/0033278 A1 | 2/2008 | Assif |
| 2008/0033281 A1 | 2/2008 | Kroeckel |
| 2008/0039897 A1 | 2/2008 | Kluge et al. |
| 2008/0049376 A1 | 2/2008 | Stevenson et al. |
| 2008/0058635 A1 | 3/2008 | Halperin et al. |
| 2008/0097189 A1 | 4/2008 | Dumoulin et al. |
| 2008/0097191 A1 | 4/2008 | Dumoulin et al. |
| 2008/0119919 A1 | 5/2008 | Atalar et al. |
| 2008/0125802 A1 | 5/2008 | Carroll |
| 2008/0130965 A1 | 6/2008 | Avinash et al. |
| 2008/0139925 A1 | 6/2008 | Lubock et al. |
| 2008/0143459 A1 | 6/2008 | Vernickel et al. |
| 2008/0154253 A1 | 6/2008 | Damasco et al. |
| 2008/0171931 A1 | 7/2008 | Maschke |
| 2008/0177183 A1 | 7/2008 | Courtney et al. |
| 2008/0183070 A1 | 7/2008 | Unal et al. |
| 2008/0190438 A1 | 8/2008 | Harlev et al. |
| 2008/0214931 A1 | 9/2008 | Dickfield |
| 2008/0215008 A1* | 9/2008 | Nance et al. ............ 604/164.03 |
| 2008/0231264 A1 | 9/2008 | Krueger et al. |
| 2008/0243081 A1* | 10/2008 | Nance et al. ............ 604/164.03 |
| 2008/0243218 A1 | 10/2008 | Bottomley et al. |
| 2008/0262584 A1 | 10/2008 | Bottomley et al. |
| 2008/0275395 A1 | 11/2008 | Asbury et al. |
| 2008/0287773 A1 | 11/2008 | Harvey et al. |
| 2008/0306375 A1 | 12/2008 | Sayler et al. |
| 2008/0306376 A1 | 12/2008 | Hyde et al. |
| 2009/0079431 A1 | 3/2009 | Piferi et al. |
| 2009/0082783 A1 | 3/2009 | Piferi |
| 2009/0088627 A1 | 4/2009 | Piferi et al. |
| 2009/0102479 A1 | 4/2009 | Smith et al. |
| 2009/0112082 A1 | 4/2009 | Piferi et al. |
| 2009/0112084 A1 | 4/2009 | Piferi et al. |
| 2009/0118610 A1 | 5/2009 | Karmarkar et al. |
| 2009/0131783 A1 | 5/2009 | Jenkins et al. |
| 2009/0143696 A1 | 6/2009 | Najafi et al. |
| 2009/0171184 A1 | 7/2009 | Jenkins et al. |
| 2009/0171421 A1 | 7/2009 | Atalar et al. |
| 2009/0306643 A1 | 12/2009 | Pappone et al. |
| 2010/0066371 A1 | 3/2010 | Vij |
| 2010/0198052 A1 | 8/2010 | Jenkins et al. |
| 2010/0286725 A1* | 11/2010 | Benjamin et al. ............ 606/213 |
| 2010/0312094 A1 | 12/2010 | Guttman et al. |
| 2010/0312095 A1 | 12/2010 | Jenkins et al. |
| 2010/0312096 A1* | 12/2010 | Guttman et al. ............ 600/411 |
| 2010/0317961 A1 | 12/2010 | Jenkins et al. |
| 2010/0317962 A1 | 12/2010 | Jenkins et al. |
| 2011/0040175 A1 | 2/2011 | Shahidi |
| 2011/0106131 A1* | 5/2011 | Argentine ............ 606/194 |
| 2011/0270192 A1* | 11/2011 | Anderson et al. ............ 604/164.1 |

FOREIGN PATENT DOCUMENTS

| | | |
|---|---|---|
| EP | 0557127 | 8/1993 |
| EP | 0673621 | 9/1995 |
| EP | 0701835 | 3/1996 |
| EP | 0701836 | 3/1996 |
| EP | 0702976 | 3/1996 |
| EP | 0732082 | 9/1996 |
| EP | 1 943 974 A1 | 7/2008 |
| JP | 62-16753 | 1/1987 |
| JP | 01-212569 | 8/1989 |
| JP | 2006-070902 | 3/1994 |
| JP | 09-094238 | 4/1997 |
| JP | 09-238924 | 9/1997 |
| JP | 09-299346 | 11/1997 |
| JP | 2001-238959 | 9/2001 |
| JP | 2003-325475 | 11/2003 |
| JP | 2004-113808 | 4/2004 |
| JP | 2006-296826 | 11/2006 |
| JP | 2006-334259 | 12/2006 |
| WO | WO/87/04080 | 7/1987 |
| WO | WO/92/10213 | 6/1992 |
| WO | WO/94/23782 | 10/1994 |
| WO | WO/95/04398 | 2/1995 |
| WO | WO/96/12972 | 5/1996 |
| WO | WO/97/29685 | 8/1997 |
| WO | WO/97/29710 | 8/1997 |
| WO | WO/97/40396 | 10/1997 |
| WO | WO/98/52461 | 11/1998 |
| WO | WO/98/55016 | 12/1998 |
| WO | WO/99/00052 | 1/1999 |
| WO | WO/99/16352 | 4/1999 |
| WO | WO/00/10456 | 3/2000 |
| WO | WO/00/25672 | 5/2000 |
| WO | WO/00/48512 | 8/2000 |
| WO | WO/00/57767 | 10/2000 |
| WO | WO/00/68637 | 11/2000 |
| WO | WO/01/01845 | 1/2001 |
| WO | WO/01/06925 | 2/2001 |
| WO | WO/01/12093 | 2/2001 |
| WO | WO/01/56469 A2 | 8/2001 |
| WO | WO 01/73461 A2 | 10/2001 |
| WO | WO/01/75465 | 10/2001 |
| WO | WO/01/87173 | 11/2001 |
| WO | WO/02/067202 | 8/2002 |
| WO | WO/02/083016 | 10/2002 |
| WO | WO/03/102614 | 12/2003 |
| WO | WO 2004/029782 A3 | 4/2004 |

(56) References Cited

FOREIGN PATENT DOCUMENTS

| | | |
|---|---|---|
| WO | WO/2005/067563 | 7/2005 |
| WO | WO/2006/081409 | 8/2006 |
| WO | WO/2006/094156 | 9/2006 |
| WO | WO/2006/136029 | 12/2006 |
| WO | WO/2007/002541 | 1/2007 |
| WO | WO/2007/005367 | 1/2007 |
| WO | WO/2007/033240 A1 | 3/2007 |
| WO | WO/2007/066096 | 6/2007 |
| WO | WO/2008/015605 | 2/2008 |
| WO | WO/2008/023321 | 2/2008 |
| WO | WO/2008/082661 | 7/2008 |
| WO | WO/2008/129510 | 10/2008 |

OTHER PUBLICATIONS

Atalar et al., "High Resolution Intravascular MRI and MRS using a Catheter Receiver Coil," MRM 36:596-605 (1996).

Bahnson, "Strategies to Minimize the Risk of Esophageal Injury During Catheter Ablation for Atrial Fibrillation: Catheter Ablation for AF Using a Combination of RF and Cryothermy Ablation—a Practical Approach," Pacing Clin. Electrophysiol. 32:248-260 (2009).

Bhakta et al., "Principles of Electroanatomic Mapping," Indian Pacing Electrophysiol. J. 8:32-50 (2008).

Biosense Webster, Inc., CARTO™ XP Electroanatomical Navigation System [Brochure] (2004) (accessed at www.biosensewebster.com/products/pdf/B0037Carto_V7_Bro_Fnl.pdf).

Bleier et al., "Real-time Magnetic Resonance Imaging of Laser Heat Deposition in Tissue," Mag. Reson. Med. 21:132-137 (1991).

Burke et al., "Integration of Cardiac Imaging and Electrophysiology During Catheter Ablation Procedures for Atrial Fibrillation," J. Electrocardiol. 39:S188-S192 (2006).

Chen et al., "Right Atrial Focal Fibriliation: Electrophysiologic Characteristics and Radiofrequency Catheter Ablation," J. Cardiovasc. Electrophysiol. 10:328-335 (1999).

Chorro et al., "Transcatheter ablation of the sinus node in dogs using high-frequency current," Eur Heart J 11:82-89 (1990).

Cummings et al., "Assessment of Temperature, Proximity, and Course of the Esophagus During Radiofrequency Ablation within the Left Atrium," Circulation 112:459-464 (2005).

Dick et al., "Magnetic Resonance Fluoroscopy Allows Targeted Delivery of Mesenchymal Stem Cells to Infarct Borders in Swine," Circulation, 108:2899-2904 (2003).

Dick et al., "Real-time MRI enables targeted injection of labeled stem cells to the border of recent porcine myocardial infarction based on functional and tissue characteristics," Proc. Intl. Soc. Mag. Reson. Med. 11, p. 365 (2003).

Dumoulin et al. "Real-Time Position Monitoring of Invasive Devices Using Magnetic Resonance," Mag. Reson. Med. 29:411-415 (1993).

Dumoulin et al., "Simultaneous Acquisition of Phase-Contrast Angiograms and Stationary-Tissue Images with Hadamard Encoding of Flow-induced Phase Shifts," JMRI 1:399-404 (1991).

Ector et al., Improved Efficiency in the EP Lab with syngo DynaCT Cardiac, AXIOM Innovations 26-32 (2008).

Edelman et al., "Magnetic Resonance Imaging," N. Engl. J. Med. 328:708-716 (1993).

Elgort et al., "Real-time Catheter Tracking and Adaptive Imaging," J. Magnetic Resonance Imaging 18:621-626 (2003).

Elgort, "Real-Time Catheter Tracking and Adaptive Imaging for Interventional Cardiovascular MRI," Case Western Reserve University student thesis (2005).

Fisher et al., "Atrial Fibrillation Ablation: Reaching the Mainstream: Methodology," Pacing Clin. Electrophysiol. 29:523-537 (2006).

Greenleaf et al., "Multidimensional Cardiac Imaging," Acoustical Imaging 20:403-411 (1993).

Grimson et al., "An Automatic Registration Method for Frameless Stereotaxy, Image Guided Surgery, and Enhanced Reality Visualization," IEEE Trans Med Imaging 15:129-140 (1996).

Guttman et al., "Imaging of Myocardial Infarction for Diagnosis and Intervention Using Real-Time Interactive MRI Without ECG-Gating or Breath-Holding," Mag. Reson. Med., 52:354-361 (2004).

Hamadeh et al., "Anatomy Based Multi-modal Medical Image Registration for Computer Integrated Surgery," SPIE 2355:178-188 (1994).

Hao and Hongo, "Use of Intracardiac Echocardiography During Catheter Ablation for Atrial Fibrillation: Maximizing Safety and Efficacy," EP Lab Digest 5(4) (2005).

Hillenbrand et al., "The Bazzoka Coil: A Novel Dual-Purpose Device for Active Visualization and Reduction of Cable Currents in Electrically Conductive Endovascular Instruments," Proc. Intl. Soc. Mag. Reson. Med. 13:197 (2005).

International Preliminary Report on Patentability Corresponding to International Application No. PCT/US2010/038816; Date of Mailing: Dec. 29, 2011; 5 pages.

International Preliminary Report on Patentability Corresponding to International Application No. PCT/US2010/038824; Date of Mailing: Dec. 29, 2011; 5 pages.

Jais et al., "Ablation Therapy for Atrial Fibrillation (AF): Past, Present and Future," Cardiovasc. Res. 54:337-346 (2002).

Jerwzewski et al., "Development of an MRI-Compatible Catheter for Pacing the Heart: Initial in Vitro and in Vivo Results," JMRI, ISHRM 6(6):948-949 (1996).

Jolesz et al., "MR Imaging of Laser-Tissue Interactions," Radiol. 168:249-253 (1988).

Kainz, "MR Heating Tests of MR Clinical Implants," J. Magnetic Resonance Imaging 26:450-451 (2007).

Kantor et al., "In vivo 31P Nuclear Magnetic Resonance Measurements in Canine Heart Using a Catheter-Coil," Circ. Res. 55:261-266 (1984).

Karmarkar, "An Active MRI Intramyocardial Injection Catheter," Proc. Intl. Soc. Mag. Reson. Med. 11:311 (2003).

Kerr et al., "Real-time Interactive MRI on a Conventional Scanner," MRM 38:355-367 (1997).

Kumar, "MR Imaging with a Biopsy Needle," Proc. Intl. Soc. Mag. Reson. Med. 9:2148 (2001).

Lewin et al., "Needle localization in MR-guided biopsy and aspiration: effects of field strength, sequence design, and magnetic field orientation," Am. J. Roentgenol. 166:1337-1345 (1996).

Morady, "Mechanisms and Catheter Ablation Therapy of Atrial Fibrillation," Tex. Heart Inst. J. 32:199-201 (2005).

Nademanee et al., "A New Approach for Catheter Ablation of Atrial Fibrillation: Mapping of the Electrophysiologic Substrate," J. Am. Coll. Cardiol. 43:2044-2053 (2004).

Notification of Transmittal of the International Search Report and the Written Opinion of the International Searching Authority issued Jan. 25, 2011 by the Korean Intellectual Property Office for corresponding PCT Application No. PCT/US2010/038816.

Notification of Transmittal of the International Search Report and the Written Opinion of the International Searching Authority issued Jan. 25, 2011 by the Korean Intellectual Property Office for corresponding PCT Application No. PCT/US2010/038824.

Ocali et al., "Intravascular Magnetic Resonance Imaging Using a Loopless Catheter Antenna," Mag. Reson. Med. 37:112-118 (1997).

Oral et al., "A Tailored Approach to Catheter Ablation of Paroxysmal Atrial Fibrillation," Circulation 113:1824-1831 (2006).

Pfister, "Architectures for Real-Time Volume Rendering," Future Generations Computer Systems 15(1):1-9 (1999).

Pickens, "Magnetic Resonance Imaging," Handbook of Medical Imaging (Beutel, et al. eds.) 1:373-461 (2000).

Quick et al., "Endourethral MRI," Mag. Reson. Med. 45:138-146 (2001).

Ratnayaka et al., "Interventional cardiovascular magnetic resonance: still tantalizing," J. Cardiovasc. Mag. Reson.10:62 (2008).

Reddy et al., "Integration of Cardiac Magnetic Resonance Imaging with Three-Dimensional Electroanatomic Mapping to Guide Left Ventiruclar Catheter Manipulation: Feasibility in a Porcine Model of Healed Myocardial Infarction," J. Am. Coll. Cardiol. 44(11):2202-2213 (2004).

Robin Medical, Inc., "Sensors" Robin Medical Inc. (2009) (accessed at http://www.robinmedical.com/sensors.html).

(56) References Cited

OTHER PUBLICATIONS

Robin Medical, Inc., "The EndoScout® Tracking System" Robin Medical Inc. (2009) (accessed at http://www.robinmedical.com/endoscout.html).

Robin Medical, Inc., Endoscout® Tracking System for MRI [Brochure] (2009) (accessed at http://www.robinmedical.com/Robin_Medical_Brochure.pdf).

Schirra et al., "A View-sharing Compressed Sensing Technique for 3D Catheter Visualization from Bi-planar Views," Proc. Intl. Soc. Mag. Reson. Med. 17:68 (2009).

Siemens USA, "Siemens Medical Solutions Revolutionizes Electrophysiology with syngo® DynaCT Cardiac Enhancement 3D Visualization of the Left Atrium, Reducing the Need for Pre-Procedural CT or MR Imaging, and Facilitating Improved Workflow," Siemens USA (2007) (accessed at http://press.siemens.us/index.php?s=43&item=94).

Silverman et al., "Interactive MR-guided Biopsy in an Open Configuration MR Imaging System," Radiol. 197:175-181 (1995).

St. Jude Medical, Inc., "EnSite Array™ Catheter," St. Jude Medical (2011) (accessed at http://wvvw.sjmprofessional.com/Products/Intl/Mapping-and-Visualization/EnSite-Array-Catheter.aspx).

St. Jude Medical, Inc., "EnSite Fusion™ Registration Module," St. Jude Medical (2011) (accessed at http://www.sjmprofessional.com/Products/US/Mapping-and-Visualization/EnSite-Fusion-Registration-Module.aspx).

St. Jude Medical, Inc., "EnSite NavX™ Navigation & Visualization Technology," St. Jude Medical (2011) (accessed at http://www.sjmprofessional.com/Products/US/Mapping-and-Visualization/EnSite-NavX-Navigation-and-Visualization-Technology.aspx).

St. Jude Medical, Inc., "EnSite Verismo™ Segmentation Tool," St. Jude Medical (2011) (accessed at http://www.sjmprofessional.com/Products/US/Mapping-and-Visualization/EnSite-Verismo-Segmentation-Tool.aspx).

St. Jude Medical, Inc., "EnSite™ System," St. Jude Medical (2011) (accessed at http://www.sjmprofessional.com/Products/US/Mapping-and-Visualization/EnSite-System.aspx).

St. Jude Medical, Inc., Ensite Fusion™ Registration Module Procedure Guide [Brochure] (2007) (accessed at http://www.ensitefusion.com/downloads/EnSiteFusionRegistrationModuleProcedureGuide.pdf).

Surgivision, Inc., "ClearTrace™ Cardiac Intervention System," Surgivision (2010) (accessed at http://www.surgivision.com/development).

Susil et al., "Multifunctional Interventional Devices for MRI: A Combined Electrophysiology/MRI Catheter," Mag. Reson. Med. 47:594-600 (2002).

Swain, "New MRI, Ultrasound Techniques Could Advance Breast Cancer Treatment," Medical Device & Diagnostic Industry Online (Apr. 1, 2004).

Torres et al.,"La cartografia electroanatomica (CARTO) en la ablacion de la fibrilacion auricular," Arch. Cardiol. Mex, 76(Supp 2):196-199 (2006).

Van Den Elsen et al., "Image Fusion Using Geometrical Features," SPIE 1808:172-186 (1992).

Weiss et al., "Transmission Line for Improved RF Safety of Interventional Devices," Mag. Reson. Med. 54:182-189 (2005).

Yang et al., "New Real-time Interactive Cardiac Magnetic Resonance Imaging System Complements Echocardiology," J. Am. Coll. Cardiol., 32:2049-2056 (1998).

Communication and extended European Search Report corresponding to European Patent Application No. EP 10 79 0114; Dated Apr. 19, 2013; 13 pages.

Office Action corresponding to Japanese Patent Application No. 2012-516263; Dispatch date: Feb. 18, 2014; 2 pages.

\* cited by examiner

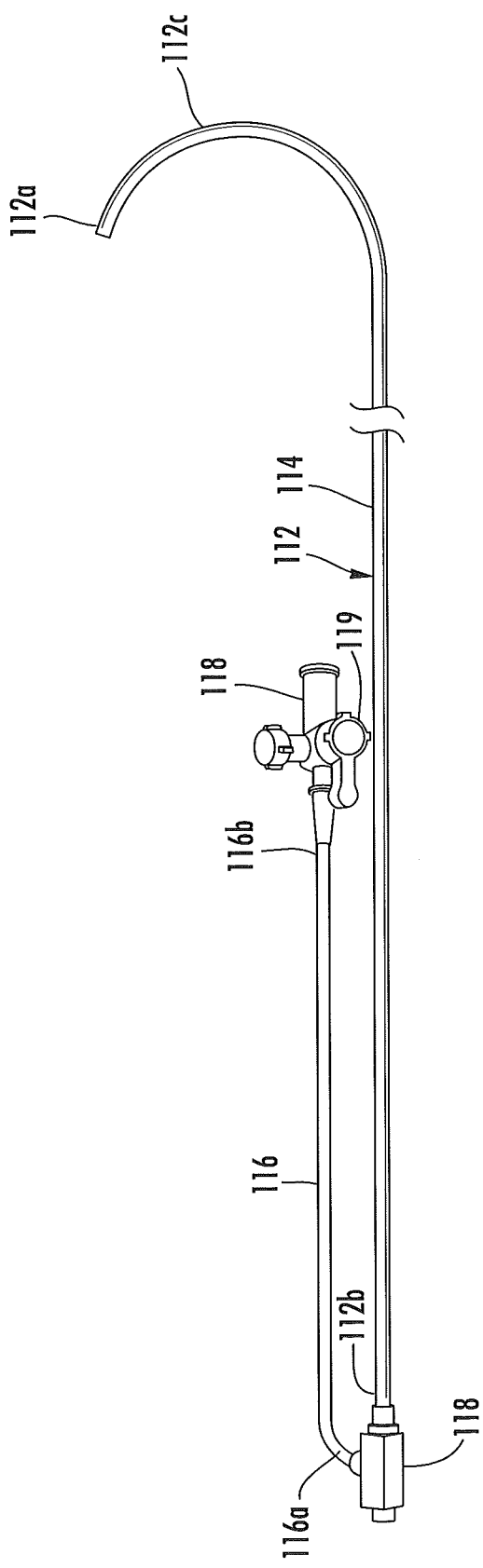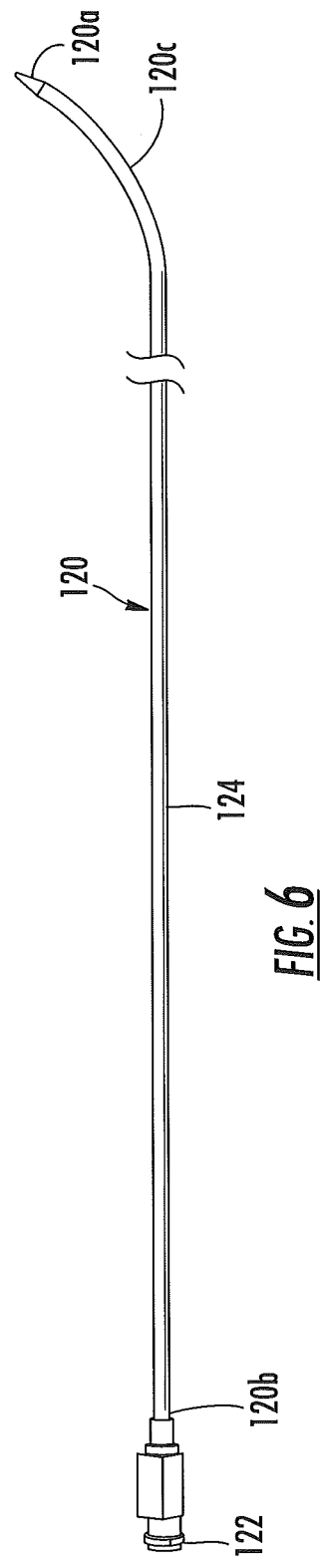
FIG. 5
FIG. 6

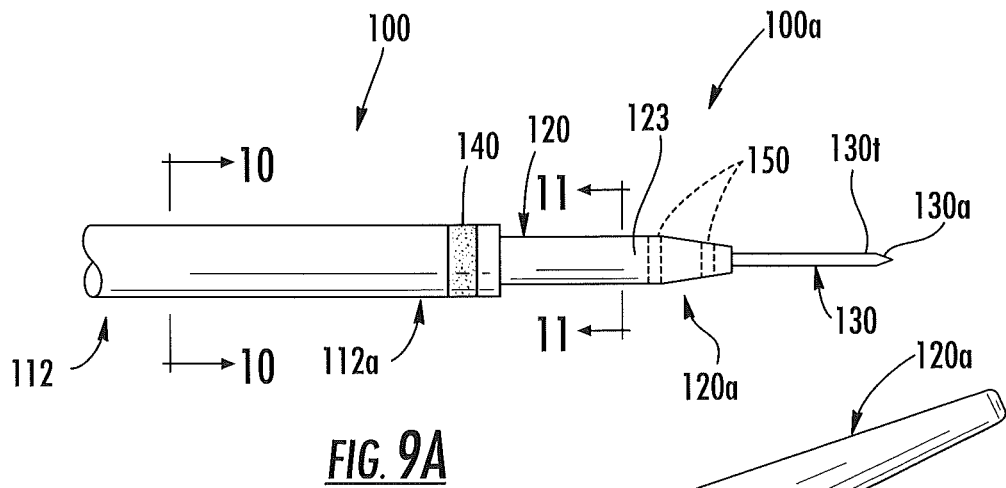
FIG. 9A
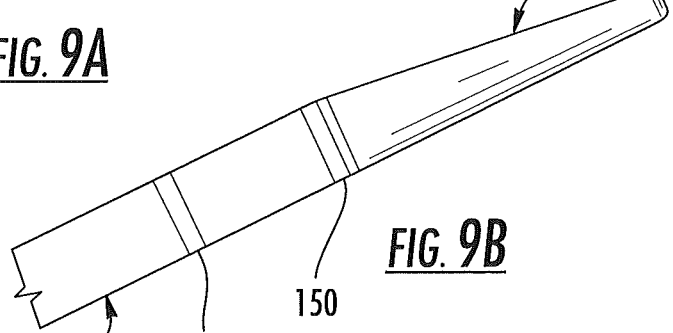
FIG. 9B
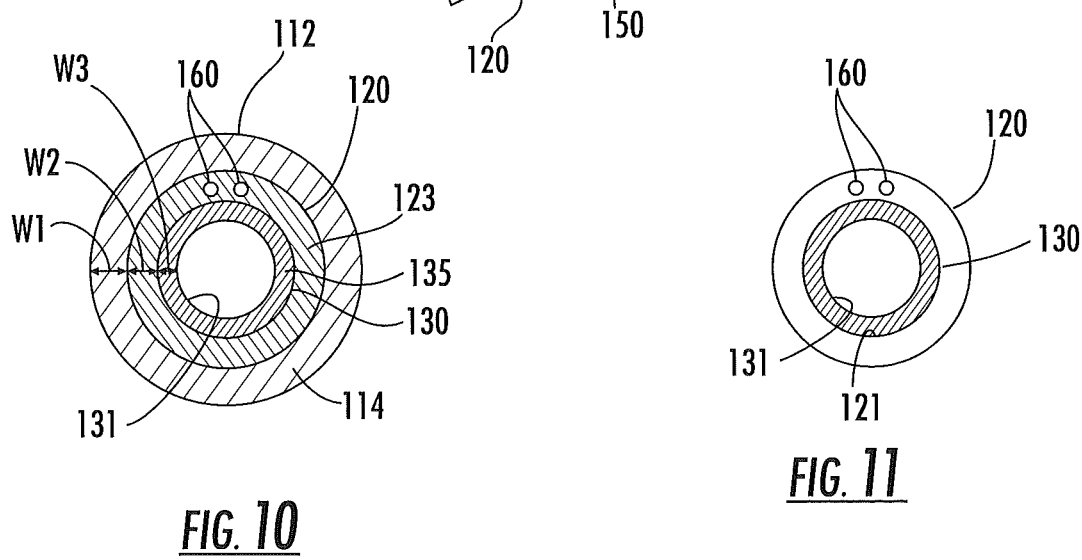
FIG. 10
FIG. 11

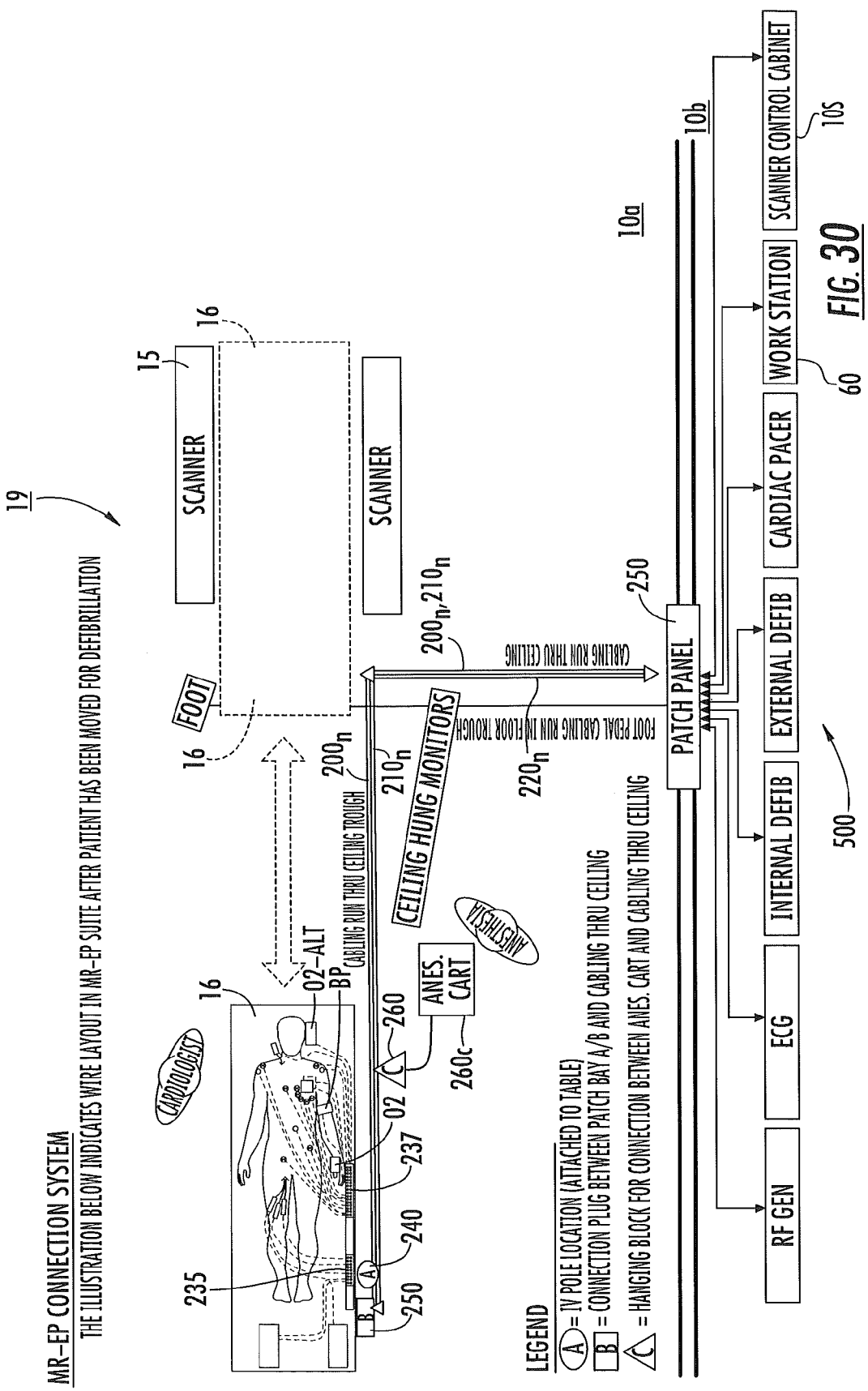

MRI-GUIDED DEVICES AND MRI-GUIDED INTERVENTIONAL SYSTEMS THAT CAN TRACK AND GENERATE DYNAMIC VISUALIZATIONS OF THE DEVICES IN NEAR REAL TIME

RELATED APPLICATION

This application is a continuation application of U.S. patent application Ser. No. 12/816,757, filed Jun. 16, 2010, which claims the benefit of and priority to U.S. Provisional Patent Application No. 61/187,323 filed Jun. 16, 2009, to U.S. Provisional Patent Application No. 61/219,638 filed Jun. 23, 2009, and to U.S. Provisional Patent Application No. 61/261,103 filed Nov. 13, 2009 the disclosures of which are incorporated herein by reference as if set forth in their entireties.

FIELD OF THE INVENTION

The present invention relates generally to medical devices and, more particularly, to MRI-guided medical devices.

BACKGROUND

Diagnostic and therapeutic procedures have been developed in which a catheter is transluminally advanced within a guide sheath or over a guidewire into various chambers of the human heart. The human heart includes a right ventricle, a right atrium, left ventricle, and left atrium. The right atrium is in fluid communication with the superior vena cava and the inferior vena cava. The tricuspid valve separates the right atrium from the right ventricle. The right atrium is separated from the left atrium by a septum that includes a thin membrane known as the fossa ovalis.

The left atrium is a difficult chamber of the heart to access with a catheter. One method of accessing the left atrium involves catheterization through the femoral vein into the right atrium, and subsequent penetration of the atrial septum to gain entry to the left atrium. Conventional transseptal medical devices used to penetrate this septum include a needle that is movable within an elongated dilator and/or sheath. The needle is maintained within the dilator until the assembly is positioned at the puncture location of the septum, and then is extended from the dilator to puncture the septum.

Conventional transseptal puncture procedures are conducted using X-ray and/or ultrasound imaging technology to facilitate guidance of the puncture device through the body and to the target location within the heart. Conventional X-ray based systems use electroanatomical maps which are virtual representations of the heart showing sensed electrical activity. Examples of such systems include the Carto® electroanatomic mapping system from Biosense Webster, Inc., Diamond Bar, Calif., and the EnSite NavX® system from Endocardial Solutions Inc., St. Paul, Minn. Unfortunately, X-ray imaging technology has a number of limitations, including limited anatomical visualization of the body and blood vessels, limited ability to obtain a cross-sectional view of a target vessel, and exposure of the subject to potentially damaging X-ray radiation.

SUMMARY

It should be appreciated that this Summary is provided to introduce a selection of concepts in a simplified form, the concepts being further described below in the Detailed Description. This Summary is not intended to identify key features or essential features of this disclosure, nor is it intended to limit the scope of the invention.

In view of the above, an MRI-guided medical device for puncturing atrial septums is provided. According to some embodiments of the present invention, the device includes an elongated sheath, an elongated dilator, and an elongated needle. The sheath has a distal end, an opposite proximal end, and a lumen extending between the proximal and distal ends. A portion of the sheath adjacent to the sheath distal end has a curved configuration that generally conforms to a curvature of the dilator and needle, as described below. The sheath comprises MRI-compatible material and includes a tracking member located adjacent to the sheath distal end that is visible in an MRI image. In some embodiments, the tracking member is a coating of MRI-visible material applied to the outer surface of the wall of the sheath.

The dilator comprises MRI-compatible material and is configured to be movably disposed within the sheath lumen. The dilator has a curved distal end, an opposite proximal end, and a central lumen extending between the dilator proximal and distal ends. The dilator distal end is configured to extend outwardly from the sheath distal end when the dilator is disposed within the sheath in an operative position. The dilator includes at least one tracking member adjacent the dilator distal end that is visible in an MRI image. The at least one tracking member may be embedded within the wall of the dilator. In some embodiments, the at least one tracking member is at least one RF coil that is electrically connected to a channel of an MRI Scanner. In some embodiments, the at least one RF coil is a pair of RF coils in adjacent spaced-apart relationship.

The needle is movably disposed within the dilator lumen and has a curved distal end, an opposite proximal end, and a central lumen extending between the needle proximal and distal ends. The needle includes a main body portion of non-conductive MRI-compatible material and a tip portion of conductive material. The tip portion is located at the needle distal end and has a tapered configuration that terminates at a sharp piercing tip. The needle is movable between retracted and extended positions relative to the dilator. The needle distal end is within the dilator lumen when in the retracted position and the needle distal end extends outwardly from the dilator distal end when in an extended or puncture position. The needle tip portion is deformable by a user. The deformable nature of the needle tip portion facilitates manipulation and placement of the needle within a subject's heart. A base dial is positioned at the needle proximal end and includes a directional indicator that indicates the direction of curvature of the needle distal end.

In some embodiments, the needle tip portion has an electrical length sufficient to define an odd harmonic/multiple of a quarter wavelength of an operational frequency of an MRI Scanner when in position in a magnetic field associated with the MRI Scanner. For example, in some embodiments, this may be a length of about four centimeters (4 cm) or less. In some embodiments, the needle tip portion may be longer than 4 cm, but may include multiple sections of conductive and non-conductive material alternately connected together, or a plurality of sections arranged in a telescopic configuration. In some embodiments, the needle tip portion includes a tracking member, such as an RF coil, to facilitate identification of the location of the needle tip portion within a subject.

In some embodiments, an RF shield is coaxially disposed within the elongated sheath so as to surround a portion of the sheath central lumen. The RF shield includes elongated inner and outer conductors, each having respective opposite first and second end portions. An elongated dielectric layer of MRI compatible material is sandwiched between the inner and outer conductors and surrounds the inner conductor. Only the respective first end portions (e.g., the proximal end portions) of the inner and outer conductors are electrically connected, and the second end portions are electrically isolated. In some embodiments, a plurality of RF shields are coaxially disposed within the elongated sheath in end-to-end spaced-apart relationship.

A transseptal medical device kit, according to some embodiments of the present invention, includes an elongated sheath, dilator, and needle as described above, along with an elongated guidewire. The guidewire has opposite distal and proximal ends and includes at least one tracking member adjacent the guidewire distal end that is visible in an MRI image. The guidewire is configured to be movably disposed within a body lumen e.g., the femoral vein, of a subject and to facilitate routing of the sheath and dilator to the heart of a subject.

The guidewire may comprise electrically non-conductive material to avoid heating when exposed to MRI. The guidewire has an atraumatic tip on the distal end thereof that is configured to guide the guidewire through the vein of a subject (e.g., the femoral vein) while avoiding perforation of the vein. In some embodiments, the atraumatic tip may have a "J-shaped" configuration. The guidewire includes at least one tracking member to facilitate routing of the guidewire in an MRI environment. In some embodiments a plurality of tracking members may be utilized and may be arranged in a defined pattern. For example, tracking members may be positioned adjacent the distal tip of the guidewire and along various other portions of the guidewire. The guidewire is routed, using MRI guidance, cranially toward the heart until it reaches the desired location. The tracking members are visible in MRI or trackable via tracking coil signals in MRI space and allow the position of the guidewire distal end to be accurately determined.

In some embodiments, the kit may include a shorter "introducer" guidewire that comprises non-metallic (at least non-ferromagnetic) material and that may initially be inserted into the vein of a subject. This introducer guidewire may have a similar configuration to the longer guidewire that is routed to the heart. For example, the introducer guidewire may have an atraumatic tip with a "J-shaped" tip, and may include multiple tracking members arranged, for example, in a pattern. This introducer guidewire is removed prior to the insertion of the longer guidewire that is routed into the heart.

Other embodiments of the present invention are directed to MRI guided interventional systems. The systems include at least one flexible medical device configured to be introduced into a patient via a tortuous and/or natural lumen path, and configured to penetrate the atrial septum in the patient's heart. In one embodiment, a flexible device includes the elongated sheath, dilator, and needle described above. At least one tracking member attached to the dilator is connected to a channel of an MRI Scanner. A circuit is adapted to communicate with and/or reside in the MRI Scanner, and is configured to: (a) obtain MR image data and generate a series of near real time (RT) MRI images of target anatomy of a patient during a surgical procedure using relevant anatomical scan planes associated with a 3-D MRI image space having a coordinate system; (b) identify coordinates associated with a location of at least a distal portion of the dilator via the at least one tracking member using the coordinate system of the 3-D MRI image space; and (c) render near RT interactive visualizations of the dilator in the 3-D image space with RT image data of target patient anatomical structure and a registered pre-acquired first volumetric model of the target anatomical structure of the patient, wherein the circuit illustrates at least a distal end portion of the dilator with a physical representation in the visualizations.

A display with a user interface is in communication with the circuit and is configured to display the visualizations during an MRI guided interventional procedure, wherein the user interface is configured to allow a user to (a) rotate the visualizations and (b) alter a displayed visualization to include only a near RT image of the target anatomy, to include the near RT image of the anatomy and the registered model of the anatomical structure, or to include only the registered model of the anatomical structure.

The MRI Scanner is configured to interleave signal acquisition of tracking signals from the at least one tracking member with image data for the near RT MRI images, and the circuit is configured to electronically track the flexible device in the 3-D image space independent of scan planes used to obtain the MR image data so that the flexible device is not required to be in any of the relevant anatomical scan planes used to obtain MR image data for the at least one near RT MRI image. The circuit is configured to calculate a device-tissue interface location proximate a tip location of the device in the three dimensional image space, and is configured to project axially forward a defined distance beyond the tip to define the device-tissue interface. The calculated tissue interface location can be utilized to automatically define at least one scan plane used to obtain the MR image data during and/or proximate in time to a septal puncture procedure using the flexible device.

It is noted that aspects of the invention described with respect to one embodiment may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail below.

BRIEF DESCRIPTION OF THE DRAWINGS

The accompanying drawings, which form a part of the specification, illustrate some exemplary embodiments. The drawings and description together serve to fully explain the exemplary embodiments.

FIG. 5 is a plan view of the sheath of the device of FIG. 4.

FIG. 6 is a plan view of the dilator of the device of FIG. 4.

FIG. 9A is an enlarged partial plan view of the distal end of the device of FIG. 4.

FIG. 9B is an enlarged partial plan view of a distal end of a dilator that may be used with the device of FIG. 4, according to other embodiments of the present invention.

FIG. 10 is a cross sectional view of the device of FIG. 9A, taken along lines 10-10.

FIG. 11 is a cross sectional view of the device of FIG. 9A, taken along lines 11-11.

FIG. 30 is a schematic illustration of an MRI-interventional suite according to some embodiments of the present invention.

DETAILED DESCRIPTION

Figure 1:
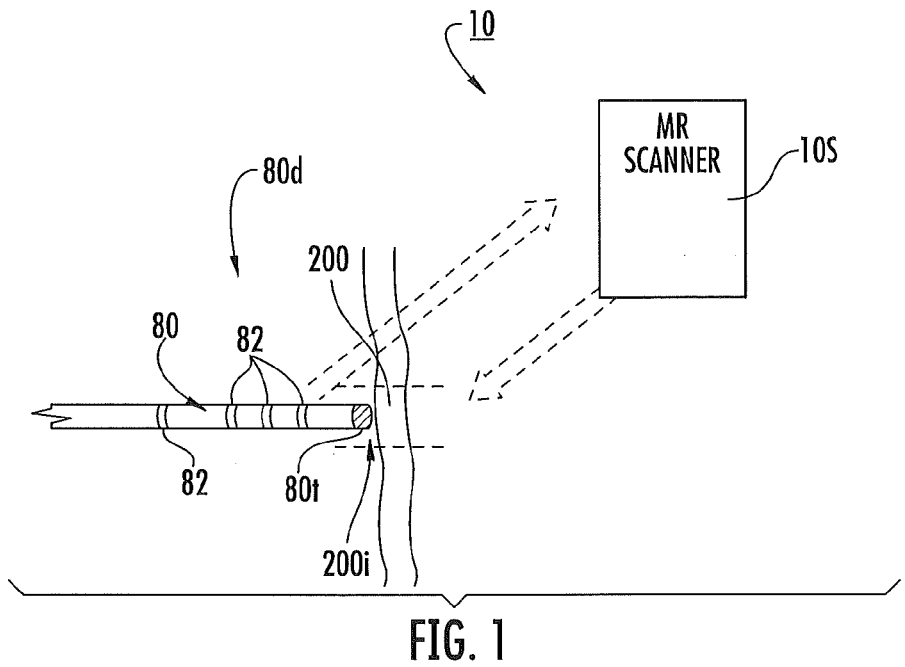
FIG. 1 is a schematic illustration of an MRI-guided system configured to show a device tissue interface using near RT MRI data according to some embodiments of the present invention.

The present invention now is described more fully hereinafter with reference to the accompanying drawings, in which some embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of "over" and "under". The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

The term "circuit" refers to an entirely software embodiment or an embodiment combining software and hardware aspects, features and/or components (including, for example, at least one processor and software associated therewith embedded therein and/or executable by and/or one or more Application Specific Integrated Circuits (ASICs), for programmatically directing and/or performing certain described actions or method steps). The circuit can reside in one location or multiple locations, it may be integrated into one component or may be distributed, e.g., it may reside entirely in an MR Scanner control cabinet, partially in the MR Scanner control cabinet, totally in a separate component or system such as a clinician workstation but communicate with MR Scanner electronics and/or in an interface therebetween, in a remote processor and combinations thereof.

The terms "MRI" or "MR Scanner" are used interchangeably to refer to a Magnetic Resonance Imaging system and includes the magnet, the operating components, e.g., RF amplifier, gradient amplifiers and processors that direct the pulse sequences and select the scan planes. Embodiments of the present invention can be utilized with any MRI Scanner including, but not limited to, GE Healthcare: Signa 1.5 T/3.0 T; Philips Medical Systems: Achieva 1.5 T/3.0 T; Integra 1.5 T; Siemens: MAGNETOM Avanto; MAGNETOM Espree; MAGNETOM Symphony; MAGNETOM Trio; and MAGNETOM Verio.

The term "pre-set scan plane" refers to scan planes electronically (programmatically) defined for subsequent use by an MRI Scanner as being associated with a location of relevant anatomical tissue of a patient during a MRI guided therapeutic or diagnostic procedure. The pre-set scan planes can be defined based on a volumetric model or map of patient anatomical structure that is subsequently registered or aligned in 3-D imaging space and can be used to acquire near real-time MR image data of patient tissue. The actual pre-set scan planes are typically electronically defined after the model used to select a desired spatial location of a corresponding relevant scan plane is registered to the 3-D imaging space.

The term "tissue characterization map" refers to a rendered visualization or image of one or more selected parameters, conditions, or behaviors of cardiac tissue using MR image data, e.g., the tissue characterization map is a rendered partial or global (volumetric) anatomical map that shows at least one defined tissue characteristic of the heart in a manner that illustrates relative degrees or measures of that tissue characteristic(s), typically in different colors, opacities and/or intensities. Notably, the tissue characterization map is to be contrasted with an electroanatomical tissue map which is based on sensed electrical activity of different regions of the heart rather than on MR image data. The visualizations can use one or both types of volumetric maps (the term "map" is interchangeably used herein with the word "model"). Thus, the visualizations can use one or both types of volumetric tissue maps, shown separately, overlaid on each other and/or integrated as a composite map. In some embodiments, tissue data from an electroanatomical map and/or the tissue characteristic map can be selectively turned on and off with respect to a pre-acquired map/model of the patient's anatomical structure (e.g., Left Atrium).

The actual visualization can be shown on a screen or display so that the map or anatomical structure is in a flat 2-D and/or in 2-D what appears to be 3-D volumetric images with data representing features or electrical output with different visual characteristics such as with differing intensity, opacity, color, texture and the like. A 4-D map can either illustrate a 3-D heart with movement (e.g., a beating heart and/or a heart with blood flow) or show additional information over a 3-D anatomic model of the contours of the heart or portions thereof.

The term "programmatically" means that the operation or step can be directed and/or carried out by a digital signal processor, computer program code and/or an Application Specific Integrated Circuit (ASIC). Similarly, the term "electronically" means that the step or operation can be carried out in an automated manner using electronic components rather than manually or using merely mental steps.

The term "RF safe" means that a device and any conductive lead is configured to operate safely when exposed to RF signals, particularly RF signals associated with MRI systems, without inducing unplanned current that inadvertently unduly heats local tissue or interferes with the planned therapy.

The term "MRI visible" means that a device or portion thereof is visible, directly or indirectly, in an MRI image. The visibility may be indicated by the increased signal-to-noise ratio (SNR) of the MRI signal proximate the device or a lack of signal at the device. When MRI-visible, a device can act as an MRI receive antenna to collect signal from local tissue and/or the device actually generates MRI signal itself, such as via suitable medical grade hydro-based coatings, fluid (e.g., aqueous fluid) filled channels or lumens.

The term "MRI compatible" means that a component is safe for use in an MRI environment and as such is typically made of non-ferromagnetic MRI compatible material(s) suitable to reside and/or operate in a high magnetic field environment.

The term "high-magnetic field" refers to field strengths above about 0.5 T, typically above 1.0 T, and more typically between about 1.5 T and 10 T. Embodiments of the invention may be particularly suitable for 1.5 T and/or 3.0 T systems.

The term "near real time" refers to both low latency and high frame rate. Latency is generally measured as the time from when an event occurs to display of the event (total processing time). For tracking, the frame rate can range from between about 100 fps (frames per second) to the imaging frame rate. In some embodiments, the tracking is updated at the imaging frame rate. For near 'real-time' imaging, the frame rate is typically between about 1 fps to about 20 fps, and in some embodiments, between about 3 fps to about 7 fps. For lesion imaging, a new image can be generated about every 1-7 s, depending on the sequence used. The low latency required to be considered "near real time" is generally less than or equal to about 1 second. In some embodiments, the latency for tracking information is about 0.01 s, and typically between about 0.25-0.5 s when interleaved with imaging data. Thus, with respect to tracking, visualizations with the location, orientation and/or configuration of a known intrabody device can be updated with low latency between about 1 fps to about 100 fps. With respect to imaging, visualizations using near real time MR image data can be presented with a low latency, typically within between about 0.01 ms to less than about 1 second, and with a frame rate that is typically between about 1-20 fps. Together, the system can use the tracking signal and image signal data to dynamically present anatomy and one or more intrabody devices in the visualization in near real-time. In some embodiments, the tracking signal data is obtained and the associated spatial coordinates are determined while the MR image data is obtained and the resultant visualization(s) with the intrabody device (e.g., flexible catheter using the tracking coil data) and the near RT MR image(s) is generated.

The term "tracking member", as used herein, includes all types of components that are visible in an MRI image including miniature RF tracking coils, passive markers, and receive antennas. In some embodiments of the present invention a miniature RF tracking coil can be connected to a channel of an MRI Scanner. The MR Scanner can be configured to operate to interleave the data acquisition of the tracking coils with the image data acquisition, as discussed further below.

MRI has several distinct advantages over X-ray imaging technology, such as: excellent soft-tissue contrast, the ability to define any tomographic plane, and the absence of ionizing radiation exposure. In addition, MRI offers several specific advantages that make it especially well suited for guiding transseptal puncture procedures including: 1) near real-time interactive imaging, 2) direct visualization of critical endocardial anatomic landmarks, 3) direct high resolution imaging of the septum, including the fossa ovalis, 4) visualization of the needle tip-tissue interface, 5) the ability to actively track needle position in three-dimensional space, and 6) elimination of radiation exposure.

Embodiments of the present invention can be configured to guide and/or place diagnostic or interventional devices in an MRI environment (e.g., interventional medical suite) to any desired internal region of a subject of interest, including, in some embodiments, to a cardiac location. The subject can be animal and/or human subjects.

Some embodiments of the invention provide systems that can be used to ablate tissue for treating AFIB, and/or to deliver stem cells or other cardio-rebuilding cells or products into cardiac tissue, such as a heart wall, via a minimally invasive MRI guided procedure while the heart is beating (i.e., not requiring a non-beating heart with the patient on a heart-lung machine).

Generally stated, advantageously, the system can be configured so that the surgical space is the imaging space and the tracking is performed in the imaging space so that there is no requirement to employ a discrete tracking system that must then be registered to the imaging space. In some embodiments, the tracking is carried out in the same 3-D imaging space but the flexible intrabody medical device is tracked independent of the imaging scan planes used to obtain the MR image data for generating images of local anatomy and is shown as a physical representation in the visualization. The system can be configured to work with robotic systems or non-robotic systems.

FIG. 1 illustrates an MRI interventional system 10 with a scanner 10S and a flexible intrabody medical device 80 proximate target tissue 200 at a device-tissue interface 200i. The system 10 can be configured to electronically track the 3-D location of the device 80 in the body and identify and/or "know" the location of the tip portion 80t of the device 80 (e.g., the dilator or needle tip) in a coordinate system associated with the 3-D imaging space. As shown in FIG. 1, the device 80 can include a plurality of spaced-apart tracking members 82 on a distal end portion thereof. The device 80 can be a device configured to punch through atrial septums (e.g., the device 100 of FIG. 4).

Figure 2:
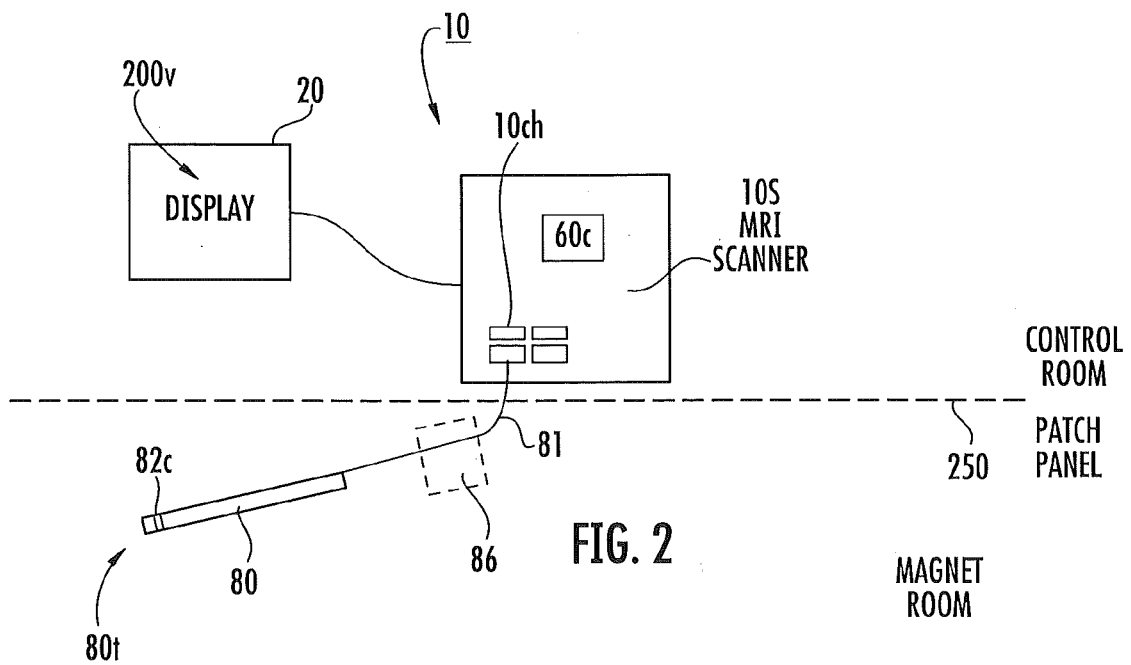
FIG. 2 is a schematic illustration of an intrabody device with a tracking coil electrically connected to a Scanner channel according to some embodiments of the present invention.

The tracking members 82 can comprise miniature tracking coils, passive markers and/or a receive antenna. In a preferred embodiment, the tracking members 82 include at least one miniature tracking coil 82c that is connected to a channel 10ch of an MRI Scanner 10S (FIG. 2). The MR Scanner 10S can be configured to operate to interleave the data acquisition of the tracking coils with the image data acquisition. The tracking data is acquired in a 'tracking sequence block' which takes about 10 msec (or less). In some embodiments, the tracking sequence block can be executed between each acquisition of image data (the 'imaging sequence block'). So the tracking coil coordinates can be updated immediately before each image acquisition and at the same rate. The tracking sequence can give the coordinates of all tracking coils simultaneously. So, typically, the number of coils used to track a device has substantially no impact on the time required to track them.

Embodiments of the present invention provide a new platform that can help facilitate clinical decisions during an MRI-guided procedure and can present real anatomical image data to the clinician in a visualization 200v. The visualizations 200v (e.g., as illustrated in FIGS. 25A-25D and 29A-29G) can be dynamically generated as the intrabody device 80 moves in the body into and/or about a target location, as a user rotates, crops or otherwise alters a displayed visualization or view and/or during navigation with minimal latent time between serial MRI image data acquisitions, typically less than about 5 seconds, typically substantially continuously with a minimal latent time of about 1 second or less, such as between about 0.001 seconds and 1 second. Together, the system 10 can use the tracking signal(s) and image signal data to dynamically track the device 80 (which is typically a plurality of devices) and present visualizations of the anatomy and one or more intrabody devices 80 in near real-time.

The term "physical representation" means that a device is not actually imaged but rather rendered with a physical form in the visualizations. The physical representation may be of any form including, for example, a graphic with at least one geometric shape, icon and/or symbol. In some particular embodiments, the physical representation may be a virtual graphic substantial replica substantially corresponding to an actual shape and configuration of the actual physical appearance and/or configuration of the associated device (see, e.g., FIGS. 29A-29G). The physical representation can be electronically generated based on a priori knowledge of the dimensions and configuration of the device. The tip and each tracking coil on a distal end of a particular device may be shown in a geometric shape (the same or different shapes, e.g., an arrow for the tip and a sphere or block or other (typically 3-D) shape for tracking coils, each in its real location in the 3-D space and in its relative position on the device and each may be rendered with the same or a different color. For example, the tip and each proximate tracking coil may be shown in a different color.

The term "tortuous" refers to a curvilinear pathway in the body, typically associated with a natural lumen such as vasculature. The term "dynamic visualizations" refers to a series of visualizations that show the movement of the device(s) in the body and can show a beating heart or movement based on respiratory cycle and the like.

The term "pre-acquired" means that the data used to generate the model or map of the actual patient anatomy was obtained prior to the start of an active therapeutic or diagnostic procedure and can include immediately prior to but during the same MRI session or at an earlier time than the procedure (typically days or weeks before).

Some embodiments of the invention provide systems that can be used to facilitate ablation of tissue for treating AFIB, or to repair or replace cardiac valves, repair, flush or clean vasculature and/or place stents, and/or to deliver stem cells or other cardio-rebuilding cells or products into cardiac tissue, such as a heart wall, via a minimally invasive MRI guided procedure while the heart is beating (i.e., not requiring a non-beating heart with the patient on a heart-lung machine). The cardiac procedures can be carried out from an inside of the heart or from an outside of the heart. The system may also be suitable for delivering a therapeutic agent or carrying out another treatment or diagnostic evaluation for any intrabody location, including, for example, the brain, gastrointestinal system, genourinary system, spine (central canal, the subarachnoid space or other region), vasculature or other intrabody locations. Additional discussion of exemplary target regions can be found at the end of this document.

The system 10 and/or circuit 60c can calculate the position of the tip 80t of the device 80 as well as the shape and orientation of the flexible device based on a priori information on the dimensions and behavior of the device 80 (e.g., for a steerable device, the amount of curvature expected when a certain pull wire extension or retraction exists, distance to tip from different coils 82 and the like). Using the known information of the device 80 and because the tracking signals are spatially associated with the same X, Y, Z coordinate system as the MR image data, the circuit 60c can rapidly generate visualizations showing a physical representation of the location of a distal end portion of the device 80 with near RT MR images of the anatomy.

In some embodiments, the tracking signal data is obtained and the associated spatial coordinates are determined while a circuit 60c in the MRI Scanner 10S (FIG. 2) and/or in communication with the Scanner 10S obtains MR image data. The reverse operation can also be used. The circuit 60c can then rapidly render the resultant visualization(s) 200v (see, e.g., FIGS. 25A-25D) with the flexible device(s) 80 shown with a physical representation based on spatial coordinates of the devices in the 3-D imaging space identified using the associated tracking coil data and the near RT MR image(s).

Figure 3:
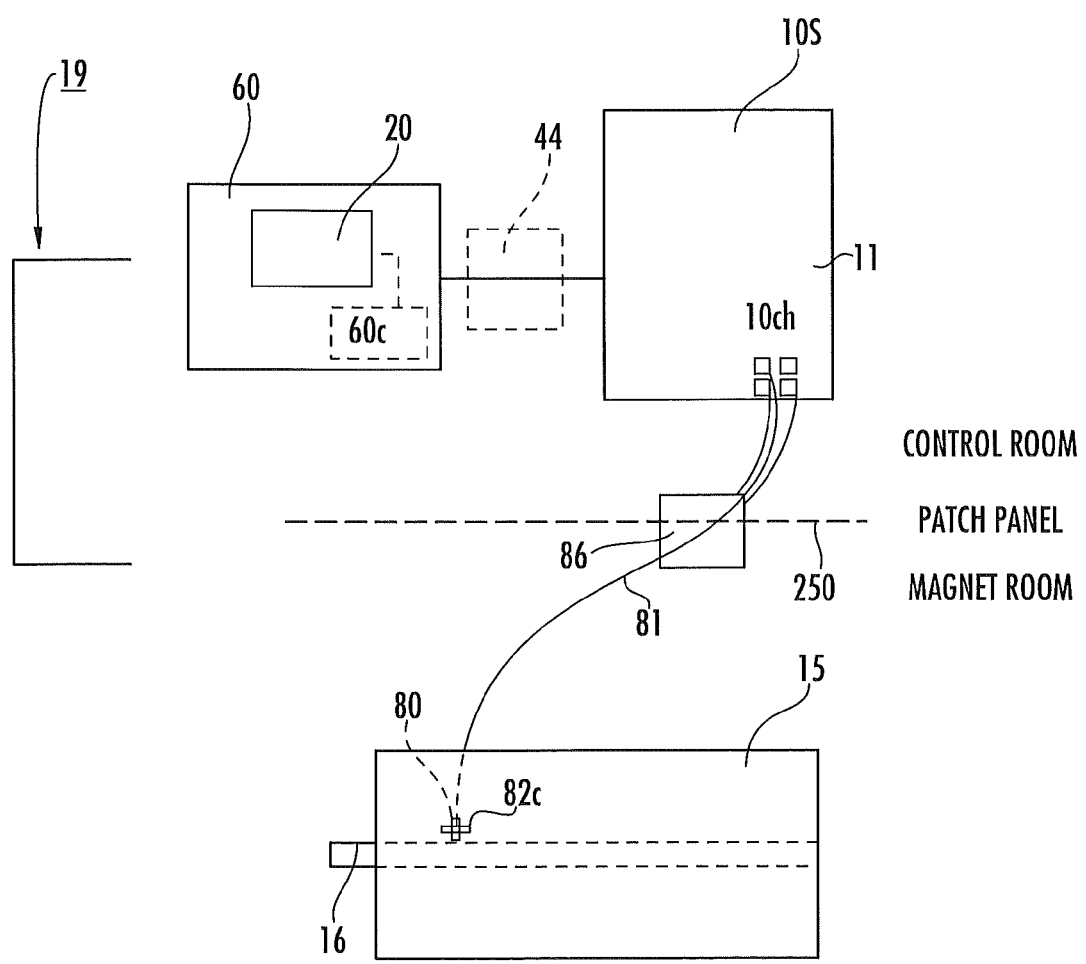
FIG. 3 is a schematic illustration of an MRI system with a workstation and display according to some embodiments of the invention.

The circuit 60c can be totally integrated into the MR Scanner 10S (e.g., control cabinet), partially integrated into the MR Scanner 10S or be separate from the MR Scanner 10S but communicate therewith. If not totally integrated into the MR Scanner 10S, the circuit 60c may reside partially or totally in a workstation 60 (FIG. 3) and/or in remote or other local processor(s) and/or ASIC. FIG. 3 illustrates that a clinician workstation 60 can communicate with the MR Scanner 10S via an interface 44. Similarly, the device 80 in the magnet room can connect to the MR Scanner 10S via an interface box 86 which may optionally be integrated into the patch panel 250.

As shown in FIGS. 2 and 3, for example, the system 10 can include at least one (interactive) display 20 in communication with the circuit 60c and/or the Scanner 10S. The display 20 can be configured to display the interactive visualizations 200v (e.g., FIGS. 25A-25D). The visualizations 200v can be dynamic showing the movement of the device 80 relative to the intrabody anatomical structure shown by the displayed near-real time MRI image. The system 10 can include a user interface (UI) 25, such as a graphical user interface (GUI) with several GUI controls 25c (FIG. 27) in communication with the display 20, and may be configured to allow a user to select to show one or more pre-acquired or in situ generated maps and/or images 30 of target tissue including different tissue characterization maps and/or an optional EA map (or data from those maps) which can be shown in and/or with the visualization 200v. For example, the system 10 can be configured to allow a user to select to show a map of patient vasculature and/or fibrous tissue based on pre-acquired image data (such as segmented MRA (Magnetic Resonance Angiography or other image slices) with the map or data therefrom being registered to and overlaid onto or incorporated into at least one of the models 200M (FIG. 25B) in the visualization and can be selectively turned on and off by a user. This information may help a clinician select a treatment site or avoid a treatment site or otherwise affect clinical choices. For example, for cardiac use, if vasculature with a relatively large blood flow is shown in a target lesion space in cardiac tissue and/or if fibrous tissue is shown, a clinician may choose another spot or may ablate longer to form a transmural lesion. Further examples of display options will be discussed further below.

In some embodiments, the system/circuit 10/60c can employ interactive application of non-selective saturation to show the presence of a contrast agent in near real-time scanning. This option can help, for example, during image-guided catheter navigation to target tissue that borders scar regions. See, e.g., Dick et al., *Real Time MRI enables targeted injection of labeled stem cells to the border of recent porcine myocardial infarction based on functional and tissue characteristics*, Proc. Intl. Soc. Mag. Reson. Med. 11, p. 365 (2003); Guttman et al., *Imaging of Myocardial Infarction for Diagnosis and Intervention Using Real-Time Interactive MRI Without ECG-Gating or Breath-Holding*, Mag. Reson. Med, 52: 354-361 (2004), and Dick and Guttman et al., *Magnetic Resonance Fluoroscopy Allows Targeted Delivery of Mesenchymal Stem Cells to Infarct Borders in Swine*, Circulation, 2003; 108:2899-2904, which describe, inter alia, imaging techniques used to show regions of delayed enhancement in (near) real-time scans. The contents of these documents are hereby incorporated by reference as if recited in full herein.

FIG. 2 illustrates that the device 80 can include at least one conductor 81, such as a coaxial cable that connects a respective tracking coil 82c to a channel 10ch of the MR Scanner 10S. The MR Scanner 10S can include at least 16 separate channels, and typically more channels but may operate with less as well. Each device 80 can include between about 1-10 tracking coils, typically between about 1-4. The coils 82c on a particular device 80 can be arranged with different numbers of turns, different dimensional spacing between adjacent coils 82c (where more than one coil is used) and/or other configurations. The circuit 60c can be configured to generate the device renderings based on tracking coil locations/positions relative to one another on a known device with a known shape and/or geometry or predictable or known changeable (deflectable) shape or form (e.g., deflectable end portion). The circuit can identify or calculate the actual shape and orientation of the device for the renderings based on data from a CAD (computer aided design) model of the physical device. The circuit can include data regarding known or predictable shape behavior based on forces applied to the device by the body or by internal or external components and/or based on the positions of the different tracking coils in 3-D image space and known relative (dimensional) spacings.

As shown in FIG. 3, the display 20 can be provided in or associated with a clinician workstation 60 in communication with an MRI Scanner 10. Other displays may be provided. The MRI Scanner 10S typically includes a magnet 15 in a shielded room and a control cabinet 11 (and other components) in a control room in communication with electronics in the magnet room. The MRI Scanner 10S can be any MRI Scanner as is well known to those of skill in the art.

Figure 32:
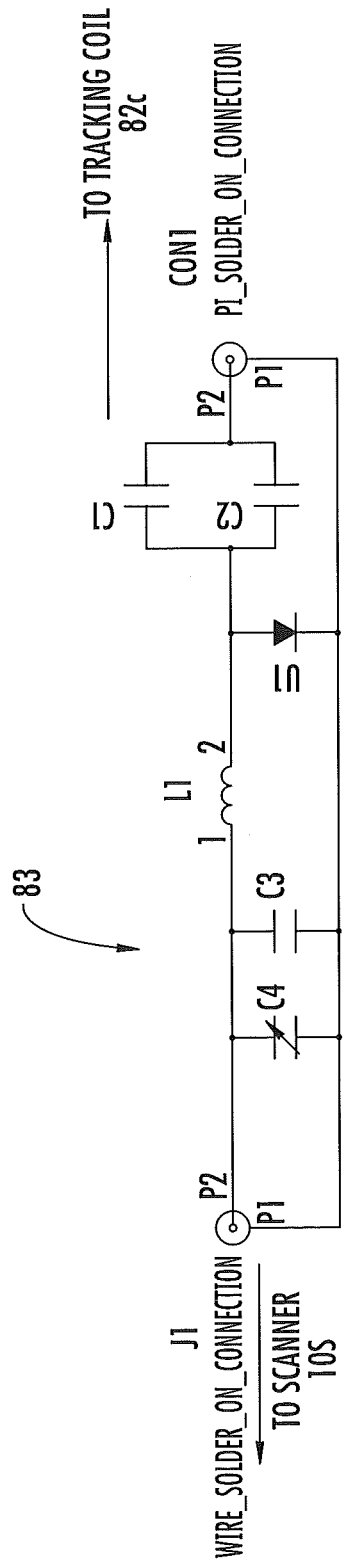
FIG. 32 is a circuit diagram of an exemplary tracking coil tuning circuit according to some embodiments of the present invention.

The tracking coils 82c can each include a tuning circuit that can help stabilize the tracking signal for faster system identification of spatial coordinates. FIG. 32 illustrates an example of a tuning circuit 83 that may be particularly suitable for a tracking coil 82c on an ablation catheter. As shown in FIG. 32, CON1 connects the coaxial cable to the tracking coil 82c on a distal end portion of the device 80 while J1 connects to the MR Scanner channel 10ch. The Scanner 10S sends a DC bias to the circuit 83 and turns U1 diode "ON" to create an electrical short which creates a high impedance (open circuit) on the tracking coil to prevent current flow on the tracking coil and/or better tracking signal (stability). The tuning circuit can be configured to have a 50 Ohm matching circuit (narrow band to Scanner frequency) to electrically connect the cable to the respective MR Scanner channel. When the diode U1 is open, the tracking coil data can be transmitted to the MR Scanner receiver channel 10ch. The C1 and C2 capacitors are large DC blocking capacitors. C4 is optional but can allow for fine tuning (typically between about 2-12 picofarads) to account for variability (tolerance) in components. It is contemplated that other tuning circuits and/or tracking signal stabilizer configurations can be used. The tuning circuit 83 can reside in the intrabody device 80 (such as in a handle or external portion), in a connector that connects the coil 82c to the respective MRI scanner channel 10ch, in the Scanner 10S, in an interface box 86 (FIG. 2), a patch panel 250 and/or the circuit 83 can be distributed among two or more of these or other components.

In some embodiments, each tracking coil 82c can be connected to a coaxial cable 81 having a length to the diode via a proximal circuit board (which can hold the tuning circuit and/or a decoupling/matching circuit) sufficient to define a defined odd harmonic/multiple of a quarter wavelength (lambda ($\lambda$)) at the operational frequency of the MRI Scanner 10S, e.g., $\lambda/4$, $3\lambda/4$, $5\lambda/4$, $7\lambda/4$ at about 123.3 MHz for a 3.0 T MRI Scanner. This length may also help stabilize the tracking signal for more precise and speedy localization. The tuned RF coils can provide stable tracking signals for precise localization, typically within about 1 mm or less. Where a plurality (e.g., two closely spaced) of adjacent tracking coils are fixed on a substantially rigid material, the tuned RF tracking coils can provide a substantially constant spatial difference with respect to the corresponding tracking position signals.

The tracking sequence used in the system 10 can intentionally dephase signal perpendicular to the read-out direction to attenuate unwanted signal from 1) bulk objects and 2) regions sensed by other signal sensitive parts of the catheter which couple to the tracking coil (e.g. the coaxial cable along the catheter shaft). This tends to leave only a sharp peak indicating the position of the tracking coil.

The tracking sequence block can include or consist of a plurality of (typically about three) repetitions of a small flip-angle excitation. Each repetition is designed to indicate the x, y or z component of the tracking coil coordinates in succession. Frequency encoding is used along the x-direction to obtain the x-coordinate, the y-direction for the y-coordinate, and the z-direction for the z-coordinate. When the frequency encoding is in the x-direction, the other two directions (y and z) are not spatially encoded, producing projection (spatially integrated) signals in those directions from all excitation regions. The dephasing gradient attempts to attenuate unwanted signal included in these projections. Once the tracking sequence block is complete, a spoiler gradient can be used to dephase any transverse signal remaining from the tracking before the imaging sequence block is executed.

The imaging sequence block obtains a portion, depending on the acceleration rate, of the data used to reconstruct an image of a single slice. If the acceleration rate is 1, then all of the data for an image is collected. If the acceleration rate is 2, then half is collected, etc. If multiple slices are activated, then each successive imaging block collects data for the next slice, in "round robin" fashion. If any saturation pulses are activated, these are executed after the tracking sequence block, immediately before the imaging sequence block.

Figure 4:
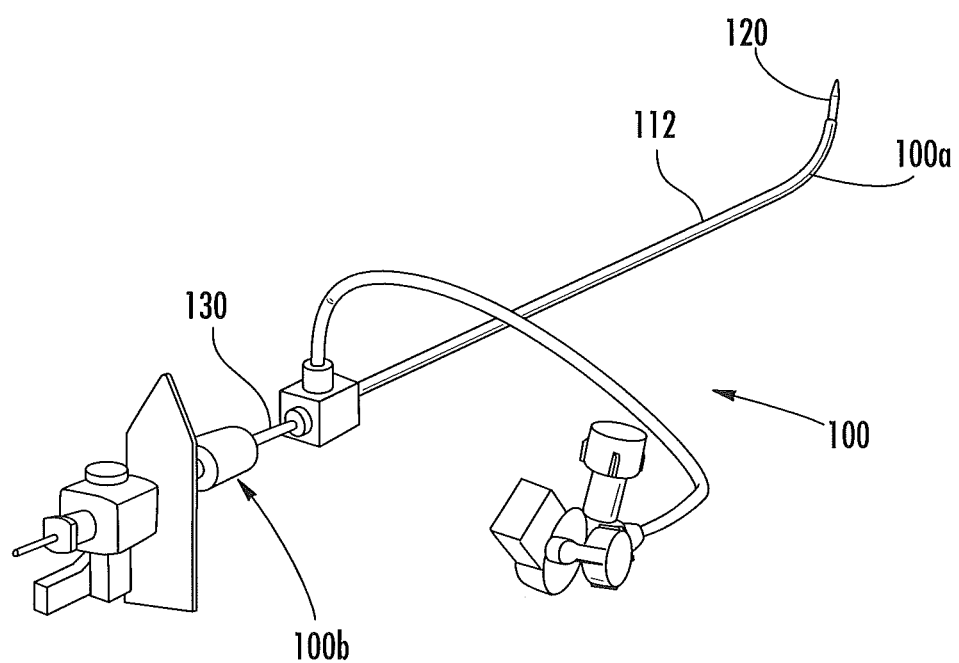
FIG. 4 is a perspective view of a flexible medical device for puncturing an atrial septum in the heart in an MRI environment, according to some embodiments of the present invention.
Figure 7:
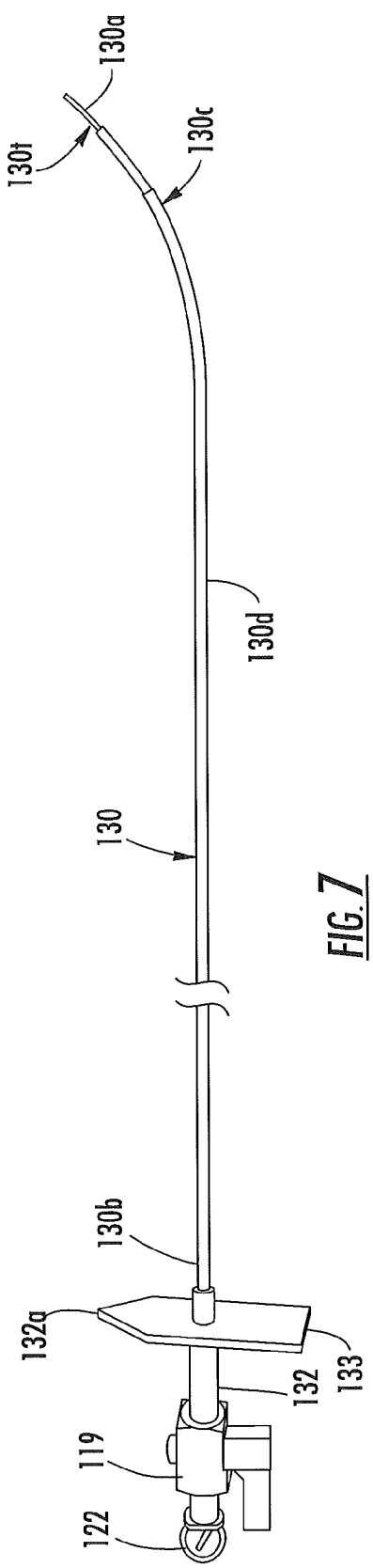
FIG. 7 is a perspective view of the needle of the device of FIG. 4.
Figure 8:
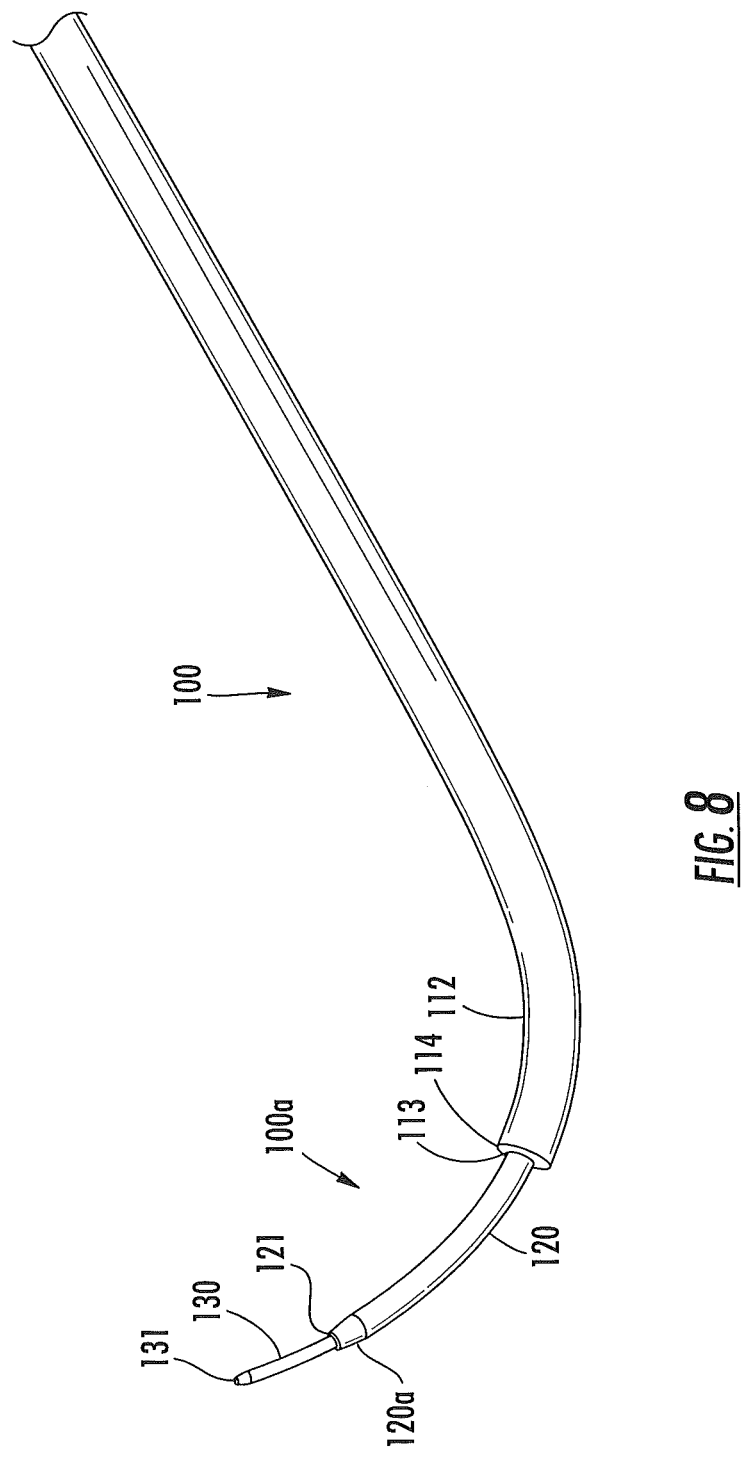
FIG. 8 is an enlarged partial perspective view of the distal end of the device of FIG. 4.

Referring now to FIGS. 4-8, a medical device 100 for use with the MRI interventional system 10 of FIG. 1, and that is configured to puncture atrial septums, will now be described. The device 100 can be tracked and displayed in an MR system 10 similar to or the same as device 80 described above with respect to FIGS. 1-3. The illustrated device 100 includes an elongated sheath 112, an elongated dilator 120, and an elongated needle 130. In FIG. 4, the needle 130 is retracted in the dilator 120. The sheath 112 has opposite distal and proximal ends 112a, 112b, and a central lumen 113 (FIGS. 5, 8). The sheath wall 114 is relatively thin. The diameter and length of the sheath 112 may vary depending upon the subject in which the device 100 is being utilized. In some embodiments, the sheath 112 may have a size of between about 5 French and about 12 French (0.010"-0.030"). However, embodiments of the present invention are not limited to any particular sheath size or length. The sheath 112 comprises MRI compatible material, such as flexible polymeric material and/or combinations of polymeric and/or non-ferromagnetic materials. Various types of materials may be utilized, as well. Embodiments of the present invention are not limited to the use of any particular MRI-compatible material.

A portion 112c of the sheath adjacent the distal end 112a has a generally curved configuration, as illustrated (FIG. 5), which generally corresponds with the curvature of the respective distal ends 120a, 130a of the dilator 120 and needle 130, respectively, and which facilitates movement and positioning of the distal end 112a of the sheath within a subject's heart. As will be described below, the distal end 112a of the sheath 112 includes at least one tracking member 140 (FIG. 9A). The tracking member 140 may comprise MRI-visible material deposited or coated or otherwise placed on or into the outer surface of the sheath wall 114. In some embodiments, the tracking member 140 may be a miniature tracking coil (e.g., tracking coil 82c, FIG. 2). In other embodiments, the tracking member 140 may be a receive antenna.

The sheath proximal end 112b is connected to a hemostasis valve 118 (FIG. 5) that is configured to seal around the dilator 120 and other devices that may be inserted through the sheath lumen 113 (FIG. 8) and to prevent or reduce blood loss and/or the entry of air. The illustrated sheath 112 in FIG. 5 also includes a tube 116 that is in fluid communication with the sheath lumen 113. The tube 116 includes opposite distal and proximal ends 116a, 116b. The tube distal end 116a is connected to the hemostasis valve 118 and is in fluid communication with the sheath lumen 113 via the hemostasis valve 118 to allow the delivery and/or removal of fluids through and from the sheath 112. The tube proximal end 116b is connected to a valve or stopcock 119 for controlling the delivery of fluids through the tube 116. Another hemostasis valve 118 is in fluid communication with the stopcock 119, as illustrated, and is configured to seal around a device inserted through the tube 116.

The dilator 120 has opposite distal and proximal ends 120a, 120b, and a central lumen 121 (FIGS. 6, 8). The dilator wall 124 is relatively thin. The diameter and length of the dilator 120 may vary depending upon the subject in which the device 100 is being utilized. In some embodiments, the dilator 120 may have a size of between about 5 French and about 12 French (0.010"-0.030"). However, embodiments of the present invention are not limited to any particular dilator size or length. The dilator 120 comprises MRI-compatible material, such as a flexible polymeric material. Various other types of MRI-compatible materials may be utilized. Embodiments of the present invention are not limited to the use of any particular MRI-compatible material.

The dilator distal end 120a has a tapered configuration, as illustrated in FIGS. 6, 9A and 9B. A portion 120c of the dilator adjacent the distal end 120a has a generally curved configuration, as illustrated. As will be described below, the dilator distal end 120a typically includes at least two tracking members 150 (FIGS. 6, 9A, 9B). FIG. 9B illustrates the distal end 120a of a dilator 120, according to other embodiments of the present invention, with a longer taper than that shown in FIG. 9A and with tracking coils 150 spaced further apart.

As shown in FIG. 6, the dilator proximal end 120b includes a Luer-lock fitting 122 that is configured to matingly engage with a mating fitting of another device. Luer-lock fittings are well known and need not be described further herein. The dilator 120 is configured to be inserted within the sheath lumen 113, as will be described below.

The needle 130 has a distal end 130a, an opposite proximal end 130b, and a central lumen 131 (FIG. 8) extending therethrough from the proximal end 130b to the distal end 130a. The size and length of the needle 130 may vary depending upon the subject in which the device 100 is being utilized. In some embodiments, the needle 130 may have a size of between about 5 French and about 12 French (0.010"-0.030"). However, embodiments of the present invention are not limited to any particular needle size or length.

A portion 130c of the needle 130 adjacent the distal end 130a has a generally curved configuration and is bendable, as illustrated in FIG. 7. The needle proximal end 130b includes a Luer-lock fitting 122 that is configured to matingly engage with a mating fitting connected to a device. The needle proximal end 130b also includes a stopcock 119 for controlling the delivery of fluids through the needle lumen 131. For example, the needle lumen 131 can be flushed with a saline or other solution delivered via a pump or other delivery system through the Luer-lock fitting 122 at the needle proximal end 130b.

As shown in FIG. 7. the needle proximal end 130b also includes a handle 132 with a base dial 133. The handle 132 is configured to be gripped by a user and to facilitate insertion of the needle 130 into the dilator 120, to facilitate extension of the needle 130 from the dilator distal end 120a, and to facilitate puncturing the septal wall via the needle distal end 130a.

As shown, the base dial 133 attached to the handle 132 includes a tapered end portion 132a that serves as a directional indicator for the curvature of the needle distal end 130a. The base dial 133 is connected to the needle proximal end 130b such that the tapered end portion 132a points in the direction that needle portion 130c is curved. The base dial tapered end portion 132a allows a user to always know in which direction the needle curved portion 130c is oriented. Other configurations/members that can indicate direction of the needle may also be utilized.

Figure 18:
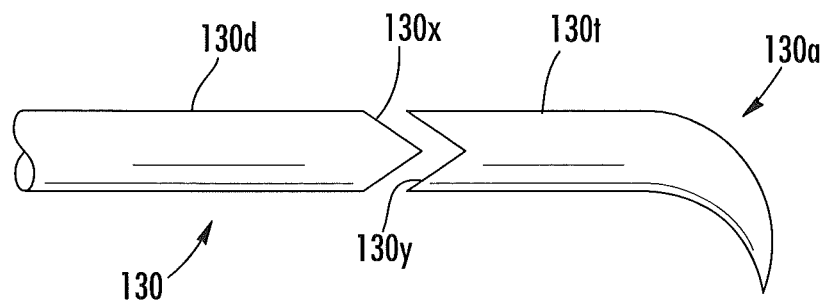
FIG. 18 is an enlarged partial plan view of the distal end of a needle that can be utilized in the device of FIG. 4, and illustrating a mating configuration of the needle tip portion and needle body, according to some embodiments of the present invention.

A tip portion 130t of the needle can comprise material visible in MRI and is configured to be deformable. Exemplary MRI-visible material includes, but is not limited to, nickel, nickel-molybdenum alloys, nickel-titanium alloys, stainless steel, titanium, and combinations thereof. The main body 130d of the needle 130 (i.e., the remaining portion of the needle 130) comprises MRI-compatible material, such as polyester or other polymeric materials. However, various other types of MRI-compatible materials may be utilized. Embodiments of the present invention are not limited to the use of any particular MRI-compatible material. Tip 130t can be bonded to the polymeric main body 130d of the needle in any of various known ways of bonding metallic and polymeric materials together including, but not limited to, adhesive bonding, ultrasonic welding or other welding, mechanical coupling, etc. FIG. 18 illustrates an exemplary embodiment wherein needle tip 130t and the needle body 130d have corresponding mating ends 130x, 130y that facilitate bonding therebetween and allow for a bendable tip 130t.

Figure 19:
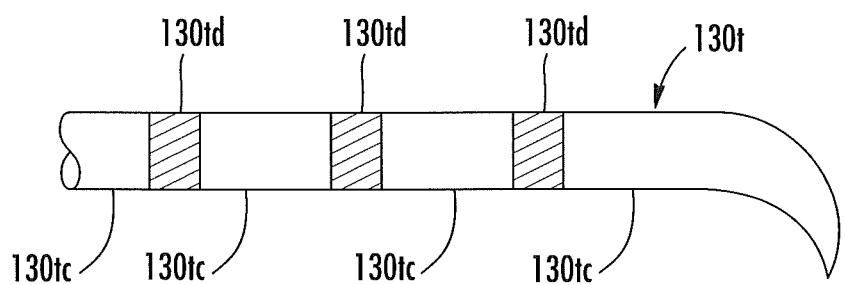
FIG. 19 is an enlarged partial plan view of the distal end of a needle that can be utilized in the device of FIG. 4, and illustrating alternating sections of conductive and non-conductive material, according to some embodiments of the present invention.
Figure 20:
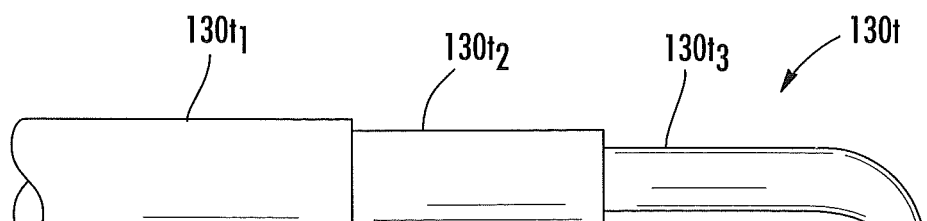
FIG. 20 is an enlarged partial plan view of the distal end of a needle that can be utilized in the device of FIG. 4, and illustrating telescoping segments, according to some embodiments of the present invention.

In some embodiments, the needle tip 130t may have a length of about four centimeters (4 cm) or less. In other embodiments, the needle tip 130t may have a length of greater than 4 cm. However, when the needle tip 130t has a length greater than 4 cm and is metallic or conductive, the needle tip 130t may be divided into physically separate sections of conductive and non-conductive material to prevent or reduce heating of the needle tip 130t when exposed to RF energy. For example, tip portion 130t may be formed of alternating sections of conductive 130tc and non-conductive 130td materials (FIG. 19). In other embodiments, the needle tip portion 130t can comprise multiple segments 130t$_1$, 130t$_2$, 130t$_3$ (FIG. 20) of MRI-visible material arranged telescopically (i.e., multiple segments joined together, each subsequent segment having a reduced outer diameter compared to the previous segment). In this embodiment, insulation between one or more segments can be utilized to reduce unwanted heating. Regardless of the length or configuration of needle tip 130t, it is desirable to limit heat generated in the presence of MRI so that the electrical length of the conductive material is less than or equal to one-quarter wavelength ($\leq \frac{1}{4}\lambda$) (e.g., in a 3 T MRI scanner, this is $\leq$4 cm for a "bare" metal needle) or an odd harmonic thereof.

In the illustrated embodiment of FIG. 9A, tip portion 130t has a tapered configuration that terminates at sharp piercing tip (i.e., the needle distal end 130a) that is configured to puncture the septal wall. The piercing tip may have a beveled configuration. In some embodiments, the needle tip portion 130t may include a tracking member, as will be described below.

Figure 24:
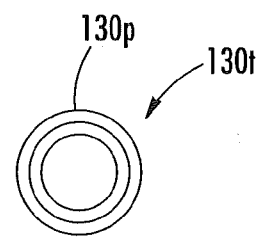
FIG. 24 is an enlarged cross sectional view of the tip portion of a needle that can be utilized in the device of FIG. 4 and illustrating a coating of material therearound, according to some embodiments of the present invention.

In some embodiments, the needle tip portion 130t has an outer coating 130p of material, as illustrated in FIG. 24.

Exemplary coating materials may include, but are not limited to, MRI-visible materials, conductive materials, non-conductive materials, polymeric materials, etc. In some embodiments, the coating 130p may extend around the entire circumference of tip portion 130t. However, in other embodiments, the coating 130p may extend only partially around the circumference of the tip portion 130t. In some embodiments, the coating 130p may extend along the entire length of the tip portion 130t. However, in other embodiments, the coating 130p may only extend along a partial length of the tip portion 130t.

FIG. 8 is an enlarged partial perspective view of the distal end 100a of the device 100 of FIGS. 4-7. Portions of the needle 130 and dilator 120 are positioned within the sheath 112, and the needle tip 130t is extended outwardly from the dilator distal end 120a (i.e., in a puncture position).

FIG. 9A is an enlarged partial plan view of the distal end 100a of the device 100 of FIGS. 4-7. In the illustrated embodiment, the distal end 112a of the sheath 112 includes a tracking member 140 in the form of a passive MRI marker. As would be understood by one of skill in the art of the present invention, passive MRI markers are visible in MRI as they generate MRI image data signals, but use no wires or circuitry. The passive MRI marker 140 can be formed from material that contains nuclei with their own distinct signal that is different from water or fat. Exemplary material includes, but is not limited to, fluorine-19 material, hydrogel, etc. When exposed to MRI, the position of the passive MRI marker 140 and, thus, the distal end 112a of the sheath 112 can be determined within the body of a subject and relative to the 3-D coordinate system of an MRI scanner. In some embodiments, the passive MRI marker 140 can be a material that does not provide any signal (i.e., shows as a dark spot in an MR image).

Figure 12A:
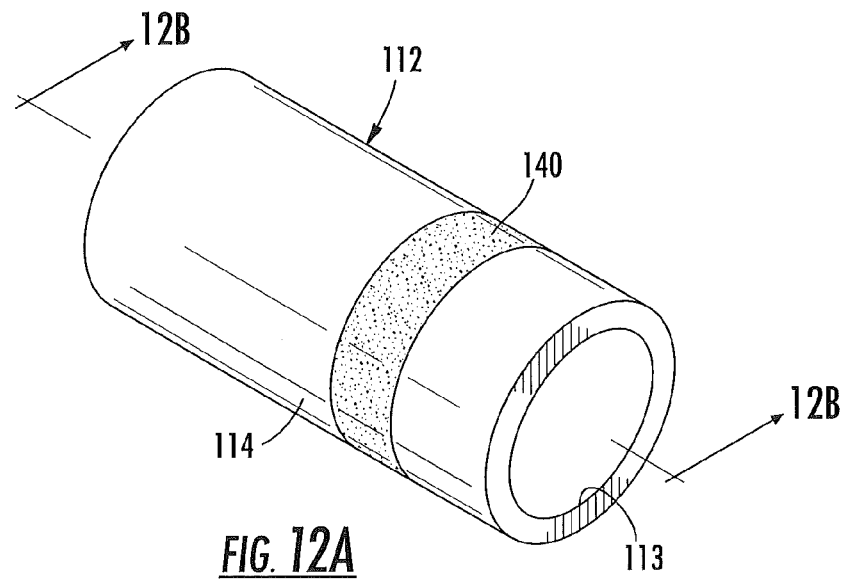
FIG. 12A is an enlarged partial perspective view of the distal end of the sheath illustrated in FIG. 9A and illustrating a tracking member, according to some embodiments of the present invention.
Figure 12B:
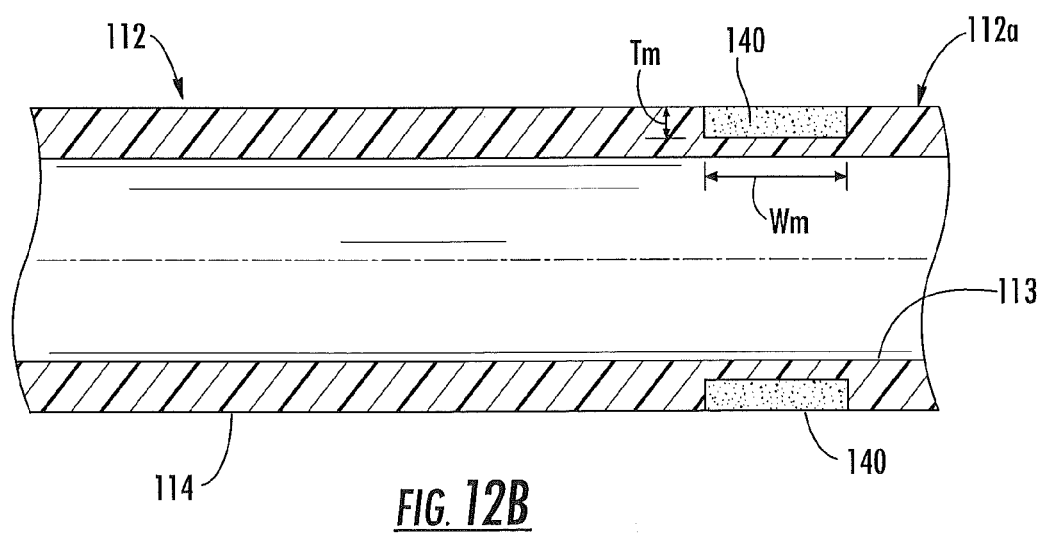
FIG. 12B is an enlarged cross sectional view of the sheath of FIG. 12A taken along lines 12B-12B.

In the illustrated embodiment, passive MRI marker 140 is a band or coating of material extending circumferentially around the sheath 112 having a thickness $T_m$ of between about 0.0005 inches and about 0.010 inches, and having a width $W_m$ of between about 0.010 inches and about 0.50 inches. FIGS. 12A-12B illustrate this embodiment in more detail. FIG. 12A is an enlarged partial perspective view of the sheath distal end 112a. The passive MRI marker 140 can be substantially flush with the surface of the sheath wall 114 and extends circumferentially therearound.

Figure 13:
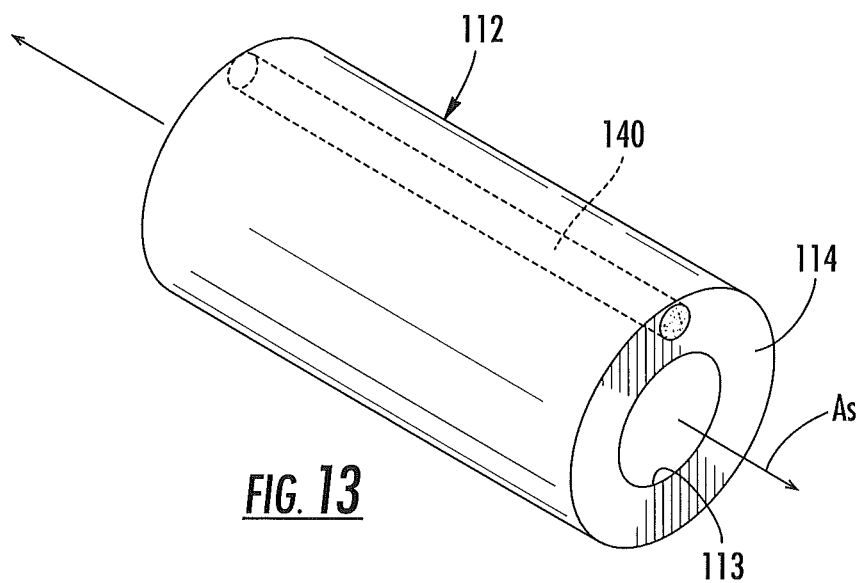
FIG. 13 is an enlarged partial perspective view of the distal end of the sheath of the device of FIG. 4 and illustrating a tracking member, according to other embodiments of the present invention.
Figure 14:
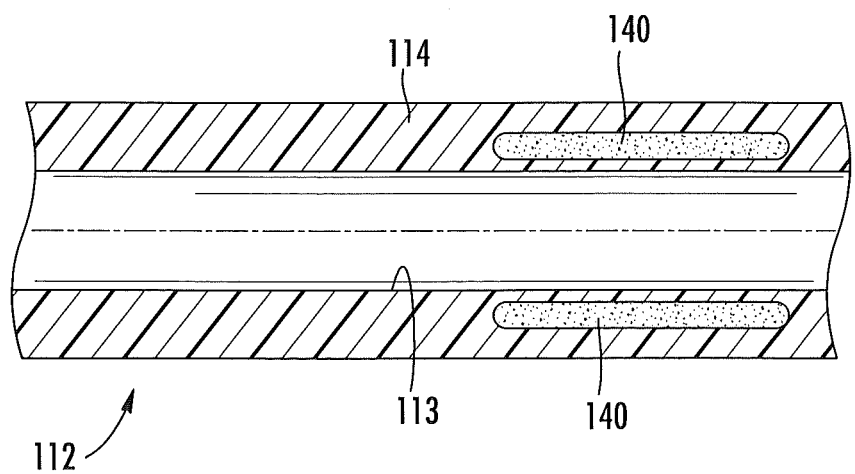
FIG. 14 is an enlarged partial cross sectional view of the distal end of the sheath of the device of FIG. 4 and illustrating a tracking member, according to other embodiments of the present invention.

Embodiments of the present invention are not limited to the illustrated configuration of passive MRI marker 140. Passive MRI marker 140 can have other configurations and shapes, without limitation. For example, as illustrated in FIG. 13, passive MRI marker 140 may be an elongated, non-ferromagnetic rod of material embedded within the sheath wall 114 and extending axially in a direction substantially parallel with the axis $A_s$ of the sheath lumen 113. In another embodiment illustrated in FIG. 14, passive MRI marker 140 may be embedded within the sheath wall 114 and extend circumferentially and elongately therearound. In other embodiments, passive MRI marker 140 may be a coating applied to the surface of the sheath wall 114. Combinations of the above may also be utilized.

Referring back to FIG. 9A, the dilator distal end 120a includes a pair of active tracking members 150 in adjacent, spaced-apart relationship. As would be understood by one of skill in the art of the present invention, active tracking members 150 generate tracking signals due to the RF signal transmission of an MRI scanner. This includes tracking members that emit an RF signal, tracking members that transmit an RF signal to the MR scanner via a connection, and tracking members that generate their own magnetic or electrical field by application of electrical currents.

In the illustrated embodiment, the active tracking members 150 are miniature RF tracking coils configured to be electrically connected to an MRI scanner channel (e.g., similar to tracking coil 82c being connected to channel 10ch in FIG. 2). The RF tracking coils 150 are typically embedded within the dilator wall 123. In some embodiments, each RF tracking coil 150 is connected to a respective coaxial cable 160 that may also be embedded within the dilator wall 123 (FIGS. 9A, 10, and 11) and extends longitudinally along the dilator 120 to an electrical connector interface 168 (FIG. 16) within housing 170 at the dilator proximal end 120b. Coaxial cables 160 are typically constructed of a metallic inner conductor and a metallic sheath "coaxially" surrounding the inner conductor that serves as an outer conductor. A dielectric material surrounds the inner conductor and electrically insulates the inner conductor from the surrounding metallic sheath. When exposed to MRI, the location of the RF tracking coils 150, and thus the location of the dilator distal end 120a can be determined based on the signal generated and/or associated with each RF tracking coil 150.

In some embodiments of the present invention, RF tracking coils 150 may be between about 2-16 turn solenoid coils, typically 2-10 turn solenoid coils. However, other coil configurations may be utilized in accordance with embodiments of the present invention. Each of the RF tracking coils 150 can have the same number of turns or a different number of turns. It is believed that an RF tracking coil 150 with between about 2-4 turns at 3.0 T provides a suitable signal for tracking purposes. A dephasing signal acquisition can be used to obtain the tracking signals as described above.

Figure 21:
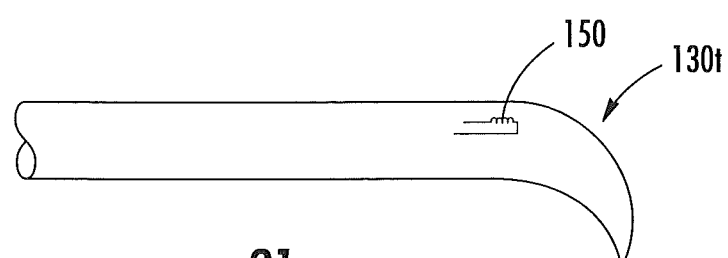
FIG. 21 is an enlarged partial plan view of the distal end portion of a needle that can be utilized in the device of FIG. 4, and illustrating an RF tracking coil associated therewith, according to some embodiments of the present invention.

In some embodiments, the tip portion 130t of the needle 130 (FIG. 21) may also or alternately include an RF tracking coil 150. Such an RF tracking coil, because of its close proximity to the RF tracking coils 150 at the dilator distal end 120a may provide increased SNR because of the cooperation of the RF coils 150 of the dilator 120 and needle tip 130t during MRI. This close positioning of RF tracking coils may provide a greater SNR than possible with just the RF tracking coils 150 on the dilator distal end 120a.

Figure 15:
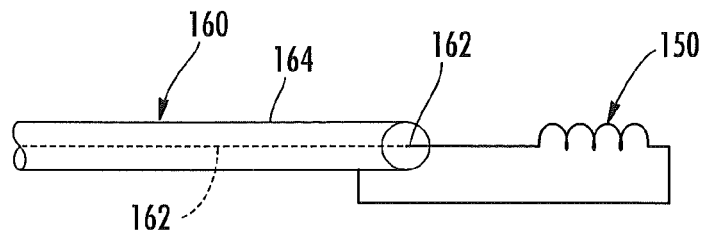
FIG. 15 is an electrical schematic diagram of an RF tracking coil at the distal end of the dilator as illustrated in FIG. 9A and a corresponding coaxial cable connected thereto, according to some embodiments of the present invention.
Figure 16:
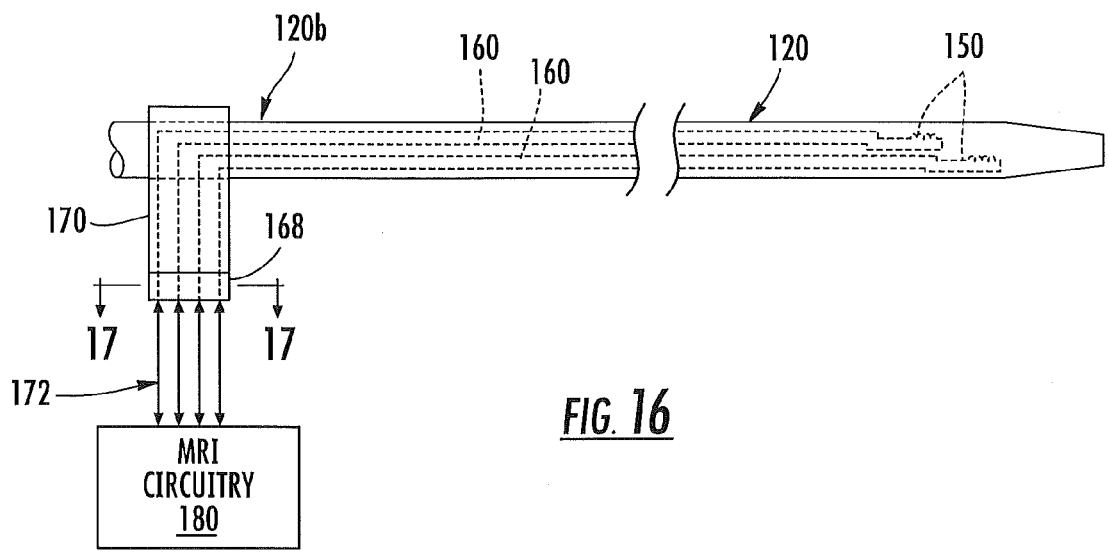
FIG. 16 schematically illustrates two coaxial cables extending along a length of the dilator of the device of FIG. 4 and terminating at a connector housing at the dilator proximal end, according to some embodiments of the present invention.

FIG. 15 is an electrical schematic diagram of an RF tracking coil 150 and corresponding coaxial cable 160 connected thereto. One end of the RF tracking coil 150 is connected to the center conductor 162 of the coaxial cable 160, and the other end of the RF tracking coil 150 is connected to the outer conductor 164 of the coaxial cable 160. FIG. 16 schematically illustrates two coaxial cables extending along the length of the dilator 120 and terminating at a connector housing 170 at the dilator distal end 120b. Cabling 172 is configured to electrically connect the coaxial cables 160 and RF tracking coils 150 to MRI circuitry 180.

Figure 17:
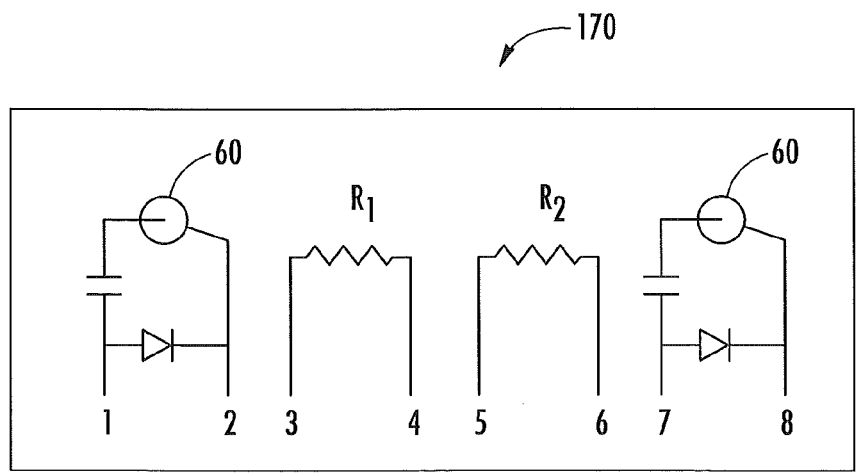
FIG. 17 is an electrical schematic illustration of the electrical connections within the connector housing illustrated in FIG. 16, according to some embodiments of the present invention.

FIG. 17 is a schematic illustration of the electrical connections (labeled as connectors 1-8) within connector housing 170. Connectors 1 and 2 are associated with one coaxial cable 160 and RF tracking coil 150, and connectors 7 and 8 are associated with the other coaxial cable 160 and RF tracking coil 150. Connectors 3 and 4 and connectors 5 and 6 are associated with the MRI scanner identification channels (e.g., channel 10ch, FIG. 2) and are used to identify that the proper device or portion thereof is connected to the proper channel. For example, this identification circuitry communicates an identification of the dilator 120 to the MRI circuitry 180 so that the MRI scanner recognizes that the dilator 120 and RF tracking coils 150 are present. However, embodiments of the present invention are not limited to the illustrated circuitry associated with RF tracking coils 150, as discussed above.

In some embodiments, the device 100 is configured to allow for safe MRI operation so as to reduce the likelihood of undesired deposition of current or voltage in tissue. The device 100 can include RF chokes such as a series of axially spaced apart Balun circuits or other suitable circuit configurations. See, e.g., U.S. Pat. No. 6,284,971, the contents of which are hereby incorporated by reference as if recited in full herein, for additional description of RF inhibiting coaxial cable that can inhibit RF induced current. In other embodiments, the device 100 can include one or more RF shields for reducing RF induced currents, as described below with respect to FIGS. 31A-31C.

The RF coils 150 and coaxial cables 60 in the device 100 can include a series of back and forth segments (e.g., it can turn on itself in a lengthwise direction a number of times along its length) and/or include high impedance circuits. See, e.g., U.S. patent application Ser. Nos. 11/417,594; 12/047, 832; and 12/090,583, the contents of which are hereby incorporated by reference as if recited in full herein. The coaxial cables 160 can be co-wound for a portion or all of a length of the dilator 120.

In some embodiments, connector housing 170 may not be located at the dilator proximal end 120b. Instead, a cable associated with the above-described electronics of the dilator 120 can extend from the dilator distal end 120b and can be configured to directly connect to an interface associated with an MRI scanner, e.g., at the edge of a gantry associated with an MR scanner or with a grounding mat utilized with the MR scanner.

Figure 22:
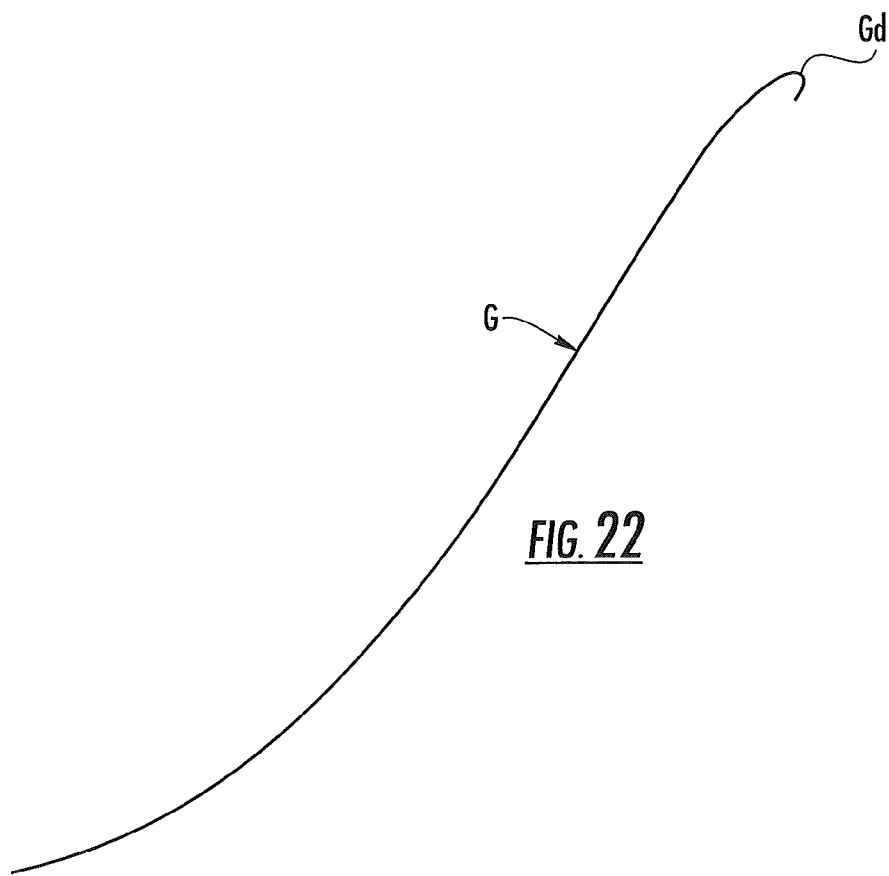
FIG. 22 is a perspective view of a guidewire that can be utilized with the device of FIG. 4, according to some embodiments of the present invention.
Figure 23:
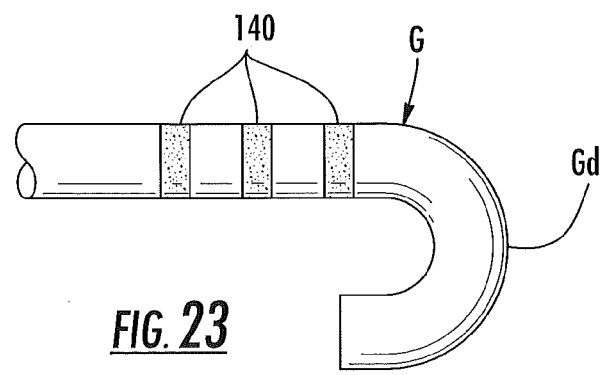
FIG. 23 is an enlarged partial plan view of the distal end of the guidewire of FIG. 22 illustrating a pattern of tracking members, according to some embodiments of the present invention.

The general steps of using the device 100 of FIG. 4 will now be described. Initially, an introducer tube is inserted into the femoral vein via a percutaneous puncture. A guidewire G (FIG. 22) is inserted through the introducer tube and into the femoral vein. The guidewire comprises non-metallic material to avoid heating issues when exposed to MRI. The guidewire has an atraumatic tip on the distal end $G_d$ thereof that is configured to guide the guidewire through the femoral vein while avoiding perforation of the femoral vein. In some embodiments, the atraumatic tip may have a "J-shaped" configuration, as illustrated in FIG. 23. The guidewire includes one or more tracking members. If a plurality of tracking members are utilized, they may be arranged in a pattern. For example, tracking members 140 (FIG. 23) may be positioned adjacent the distal tip $G_d$ of the guidewire G and along various other portions of the guidewire. The guidewire is routed, using MRI guidance, cranially toward the heart until it reaches the right atrium via the inferior vena cava. The tracking members 140 are visible in MRI and allow the position of the guidewire distal end $G_d$ to be accurately determined. An exemplary length of the guidewire is about one hundred fifty centimeters (150 cm), although embodiments of the present invention are not limited to guidewires of this length.

In some embodiments, a shorter "introducer" guidewire, e.g., about fifty centimeters (50 cm) in length, and comprising non-metallic material may initially be inserted through the introducer tube and into the femoral vein. This introducer guidewire may have a similar configuration to the longer guidewire that is routed to the heart. For example, the introducer guidewire may have an atraumatic tip with a "J-shaped" tip, and may include multiple tracking members arranged in a pattern. This introducer guidewire is removed prior to the insertion of the guidewire that is routed into the heart.

The sheath 112 is routed over the guidewire G, through the skin puncture, through the wall of the femoral vein, and into the central lumen of the femoral vein. The dilator 120 is inserted through the proximal end 112b of the sheath 112 and routed through the sheath 112, over the guidewire, and advanced to the right atrium. The guidewire is removed and the needle 130 is inserted through the proximal end 120b of the dilator 120 and routed to the right atrium. In some embodiments, the sheath 112 and dilator 120 are routed over the guidewire together as a unit, rather than as separate steps. It is understood that the above described steps may vary depending on the physician performing the procedure.

The sheath 112 and dilator 120 are positioned, under MRI guidance, so that the distal end 112a, 120a of each is located at the desired location with respect to the atrial septum that divides the right atrium from the left atrium. The needle 130 is next advanced through the distal end 120a of the dilator 120 and punctures the atrial septum. The dilator 120 is then advanced over the needle 130 until the distal end 120a of the dilator resides within the left atrium. The sheath 112 is then advanced into the left atrium. The dilator 120 and needle 130 are removed from the sheath 112 leaving the sheath 112 in position in the left atrium and providing an access path into the heart for diagnostic and/or therapeutic procedures.

Referring now to FIGS. 25A-25D and 26, examples of visualizations 200v with a physical representation 80R of the intrabody device 80 (e.g., the septal puncture device 100 of FIGS. 4-7), a volumetric model 200M of target anatomical structure and a near real-time MRI image 200MRI. For clarity, it is restated that device 80 may represent the septal puncture device 100 of FIGS. 4-7, and the physical representation 80R may be the physical representation of at least a distal end of one or more components of device 100. The circuit 60c/Scanner 10S is configured to present a 3-D volumetric model of at least a portion of the patient's heart 200M in the visualization 200v with the model registered to the 3-D imaging space along with a physical representation of at least the distal end portion of the at least one intrabody device 80R in the imaging space. Optionally, the visualizations can be carried out to show the tracking coils in the physical representation of the distal end portion of the medical device in different colors using the identified location of the tracking coils and defined form factor and/or dimensional data regarding actual coil placement on the device.

The circuit 60c can be configured to generate the visualizations 200v with at least two visual reference planes 41, 42 (shown with a third intersecting plane 43) that are typically oblique or orthogonal to each other and extend through at least a major portion of the visualization 200v. The planes 41, 42 (and 43) can be transparent and/or translucent. They may be shown with different color perimeters that correspond to a respective two-dimensional image slice (which may be shown as thumbnails on the display also with a perimeter of similar or the same color).

The planes 41, 42 can move relative to each other in the imaging space or may be locked together, in any case they can be configured to move relative to the model 200M in the imaging space. As shown in FIGS. 25A-25D, a user can rotate and zoom the visualization 200v which automatically adjusts the visualization shown on the display. As also shown, the flexible device 80 is not required to be in any of the relevant anatomical scan planes used to obtain MR data for the at least one near RT MRI image 100MRI in the visualization and the distal end portion 80d of the flexible device 80 can take on a curvilinear shape and the tip 80t can be steered or guided into different target positions.

Figure 25A:
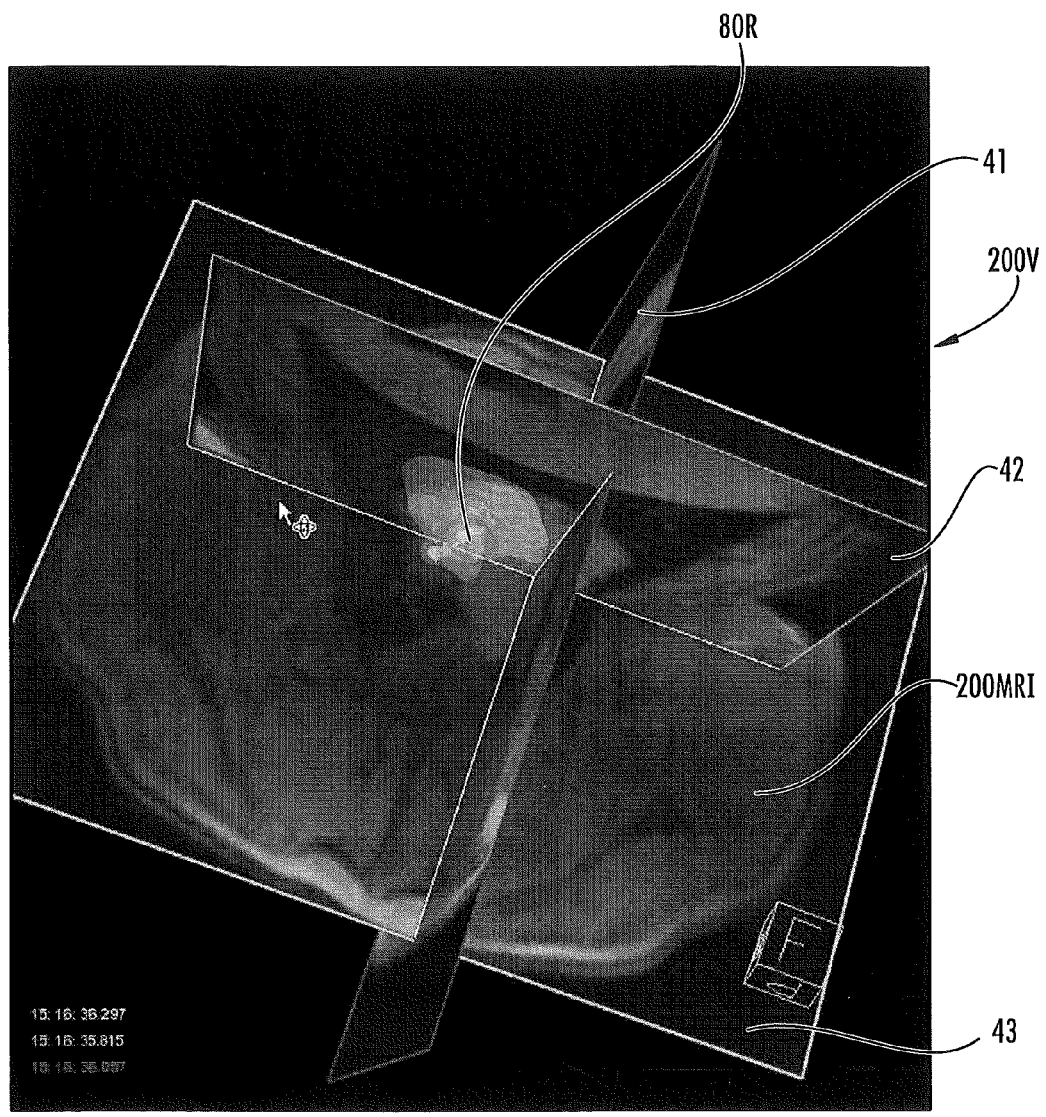
FIGS. 25A-25D are contemplated screen shots of exemplary interactive visualizations with a physical representation of an intrabody flexible medical device, such as the device of FIG. 4, according to some embodiments of the present invention.
Figure 25B:
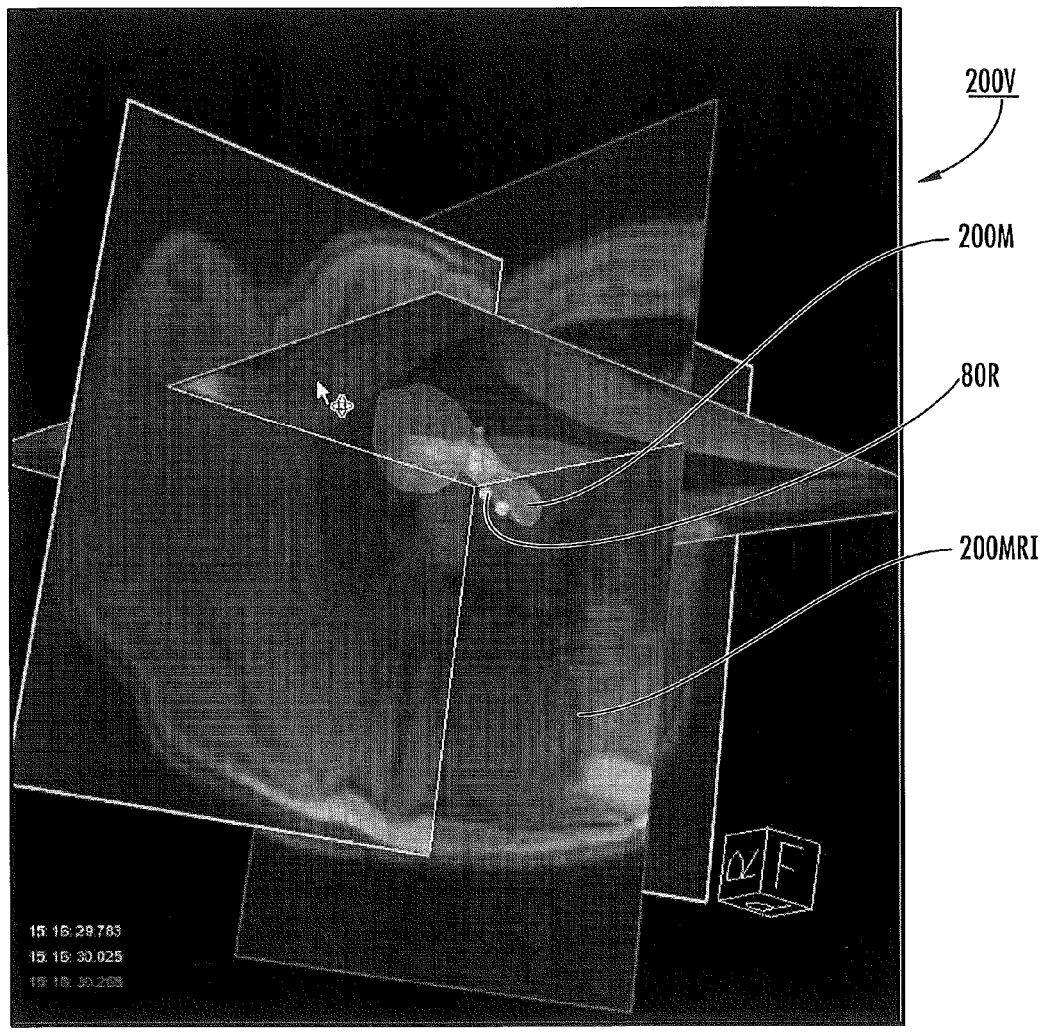
Figure 25C:
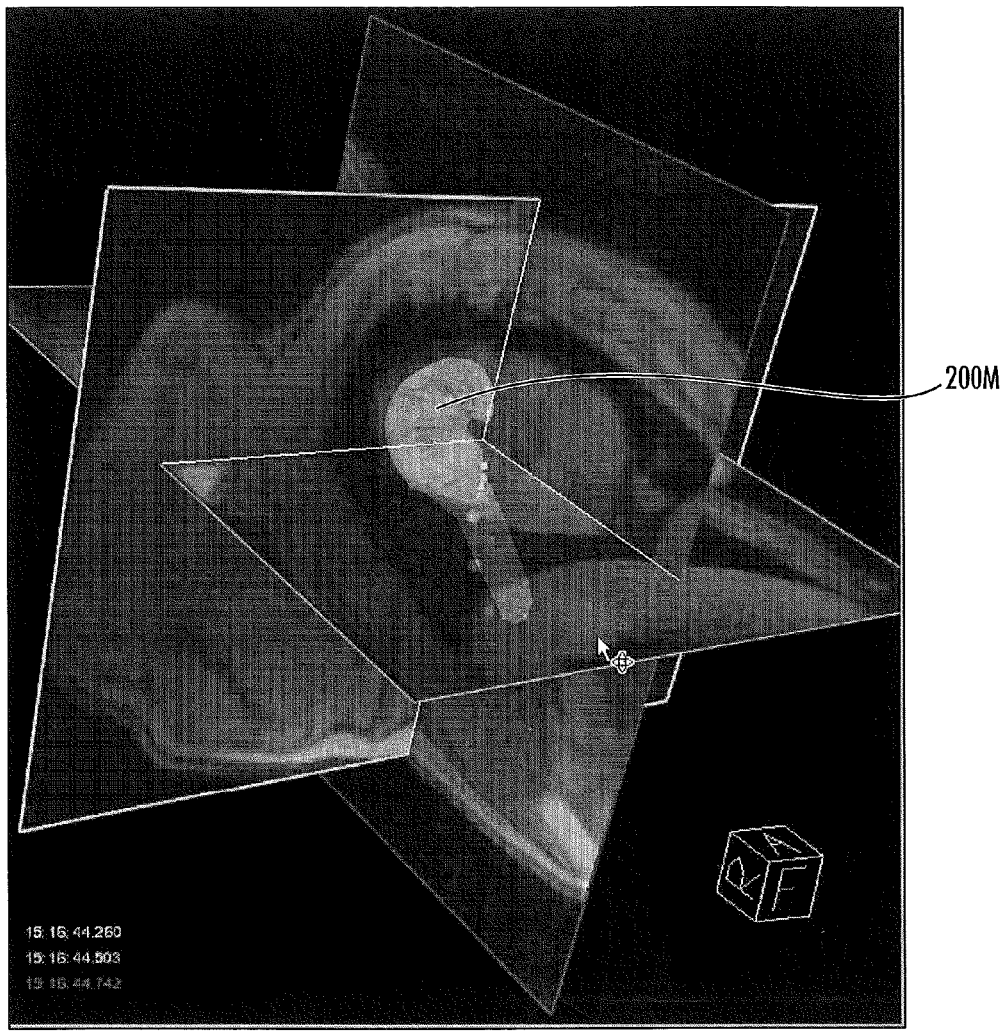
Figure 25D:
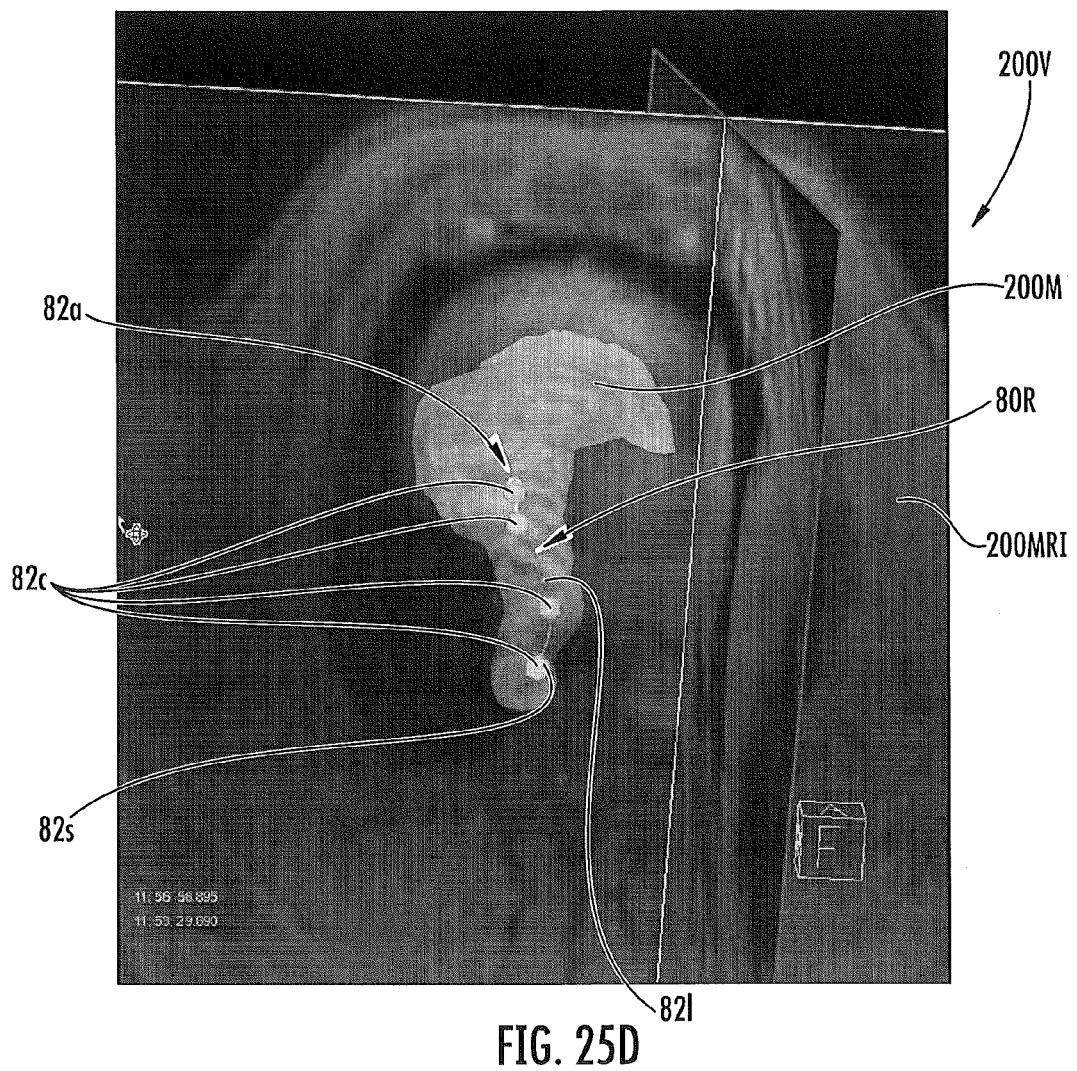

In some embodiments, as shown in FIG. 25D, the circuit 60c (FIG. 2) is configured to associate a tip location of the device 80 with an arrow 82a and render the visualization so that each tracking coil 82 on the distal end portion 80d has a shape 82s with a color, with each tracking coil 82 having a respective different color from the other tracking coils, and with a line or spline 82/connecting the tip 82a and the coils 82c and the line 82l is able to flex, bend and move to reflect movement of the device 80 in the visualizations 200v. The system/circuit can be configured to display color-highlighted images from tracking coil channels and display them with the images in the 3D rendering of the physical representation.

Figure 26:
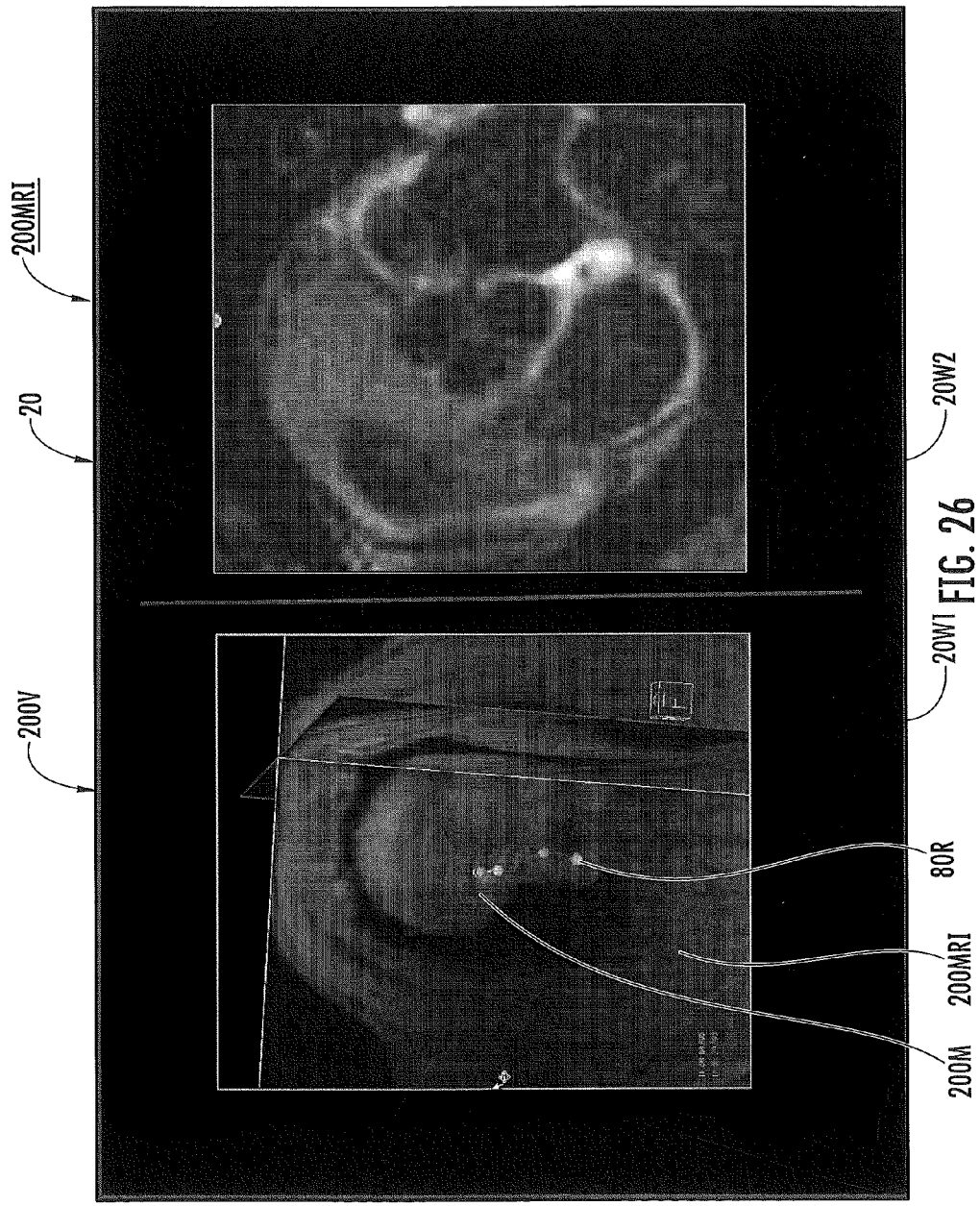
FIG. 26 is a schematic illustration of a display with two viewing windows, one showing an interactive visualization and the other showing at least one relevant near RT MRI image according to some embodiments of the present invention.

FIG. 26 illustrates that the system 10 (FIG. 1) can be configured to show both the interactive visualization 200v in one viewing window 20w1 and an MRI image 200MRI alone in a second viewing window 20w2. The MRI image 200MRI in the second window 20w2 is typically associated with the target anatomy location (identified by a user) in the interactive visualization 200v in the first viewing window 20w1.

Figure 27:
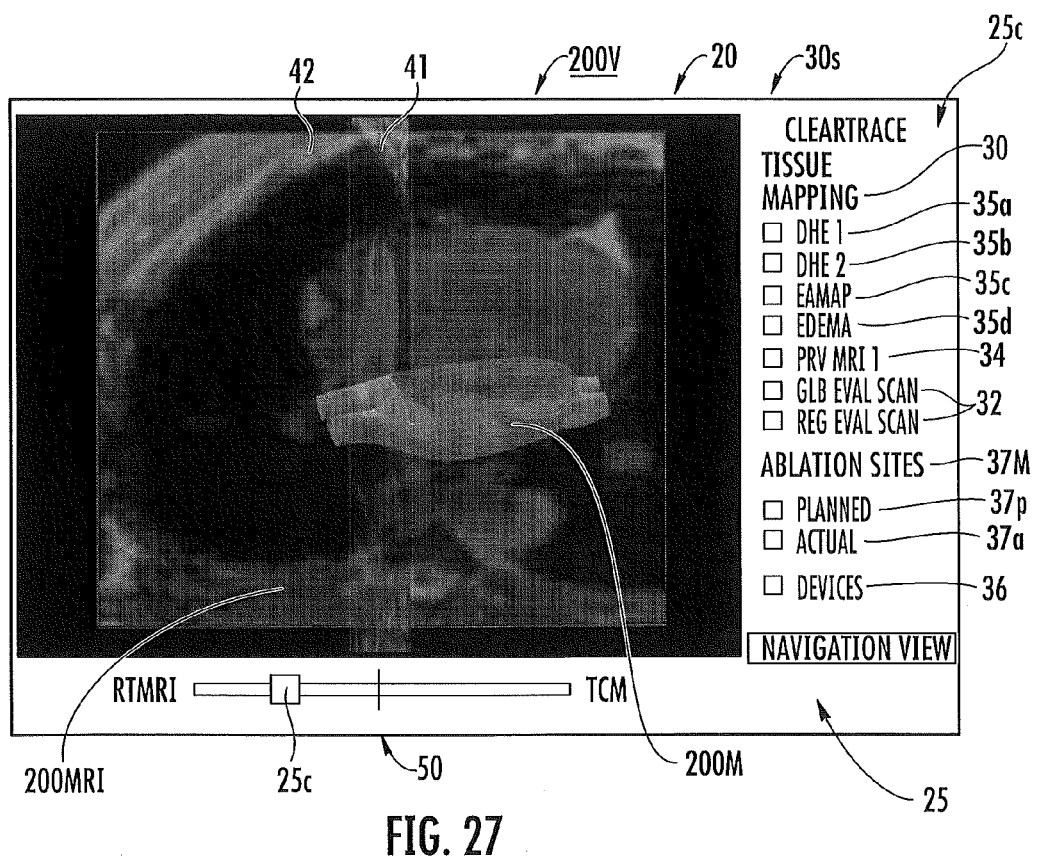
FIG. 27 is a contemplated screen shot of an exemplary visualization on a display and GUI controls that can be generated to facilitate an MRI guided procedure using the device of FIG. 4, according to some embodiments of the present invention.

As shown in FIG. 27, the display 20 can have a UI 25 configured to allow a physician or other clinician to select whether to show near real time MR images of target tissue 200MRI either with a model 200M of the target anatomical structure (e.g., heart or access path thereto) and/or in a separate viewing window (FIG. 26). The circuit 60 is in communication with at least one display 20 with the UI 25.

The UI 25 can be configured to allow a user to alter the displayed visualization (fade) to include only a near RT image of the anatomy, to include the near RT image of the anatomy and the registered model of the heart, or to include only the registered model, see, e.g., FIG. 27 showing both types of images in the visualization 200v. The UI 25 can be an on off selection of these options or may "fade" from one viewing option to another. As shown, a virtual sliding GUI control 25c allows a user to change what is shown ((near) RTMRI 100MRI to only the Model 100M).

The circuit 60c can also be configured to generate images showing the device location in MR image space. The UI 25 can also be configured to allow a user to fade the renderings of the device 80 in and out of the visualizations with actual images of the device and tracking coils to confirm location or for additional visual input. The device may include other fiducial markers (e.g., a passive marker or an active marker such as receive antenna) for facilitating the visual recognition in the MR image.

The UI 25 typically includes multiple GUI controls 25c that can include a touch screen input control to allow a clinician/physician to select a region of interest in the map 200M by placing a cursor or by touching the screen at a region of interest. This can cause the system to obtain real time MR image data of that region and provide the associated image on the display and/or define scan planes (which may be preset scan planes) at that location in space.

Figure 28:
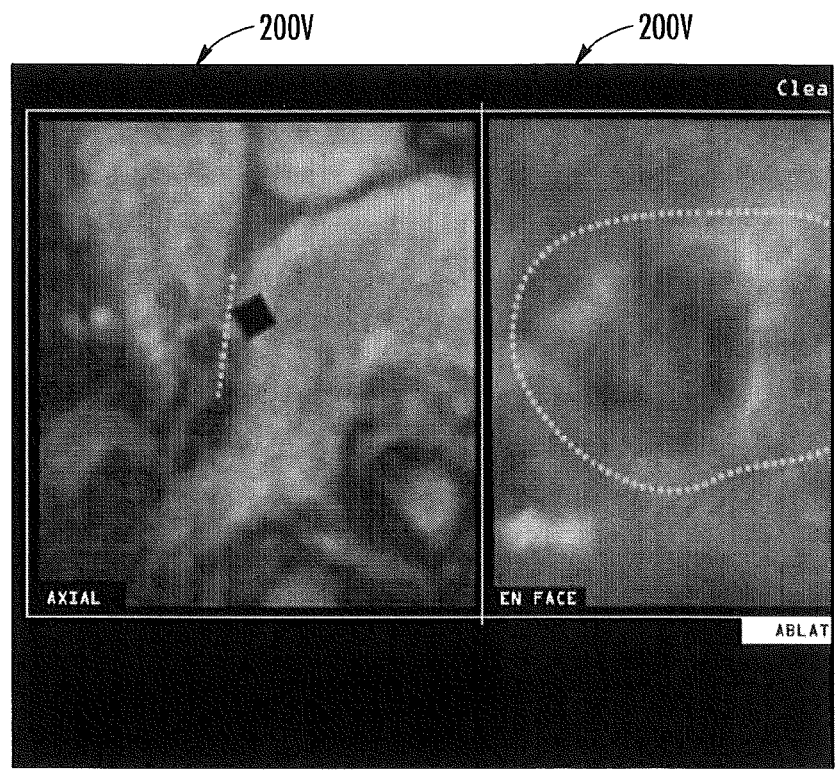
FIGS. 28 and 29A-29G are exemplary screen shots illustrating navigational indicia that can be used to help guide and/or position an intrabody device, such as the septal puncture device of FIG. 4, according to embodiments of the present invention.

FIG. 28 illustrates that the system 10 (FIG. 1) can illustrate the location of the treatment device 80 with additional visual indicators and a "target" mark for help in navigation to the site.

Figure 29A:
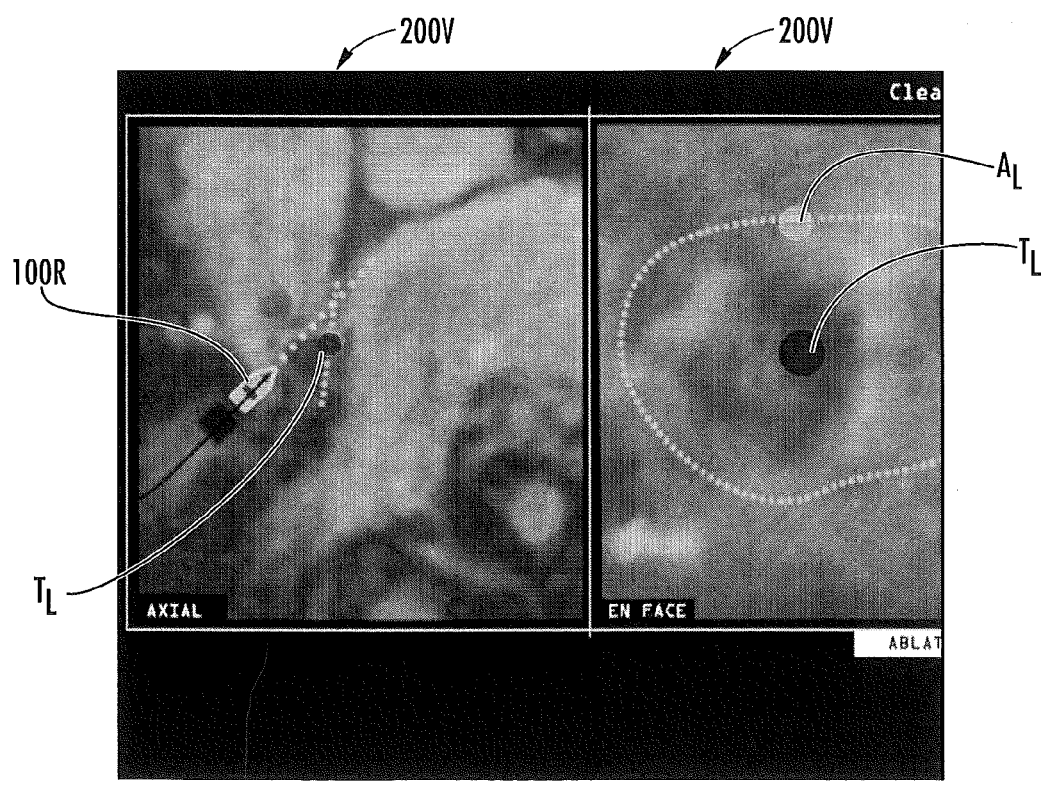
Figure 29B:
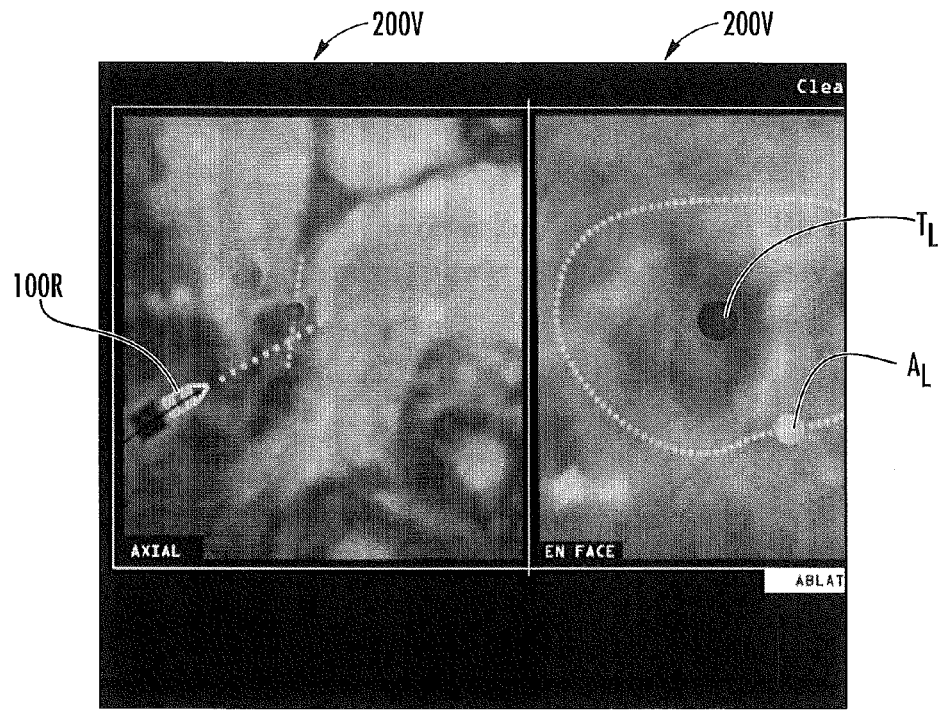
Figure 29C:
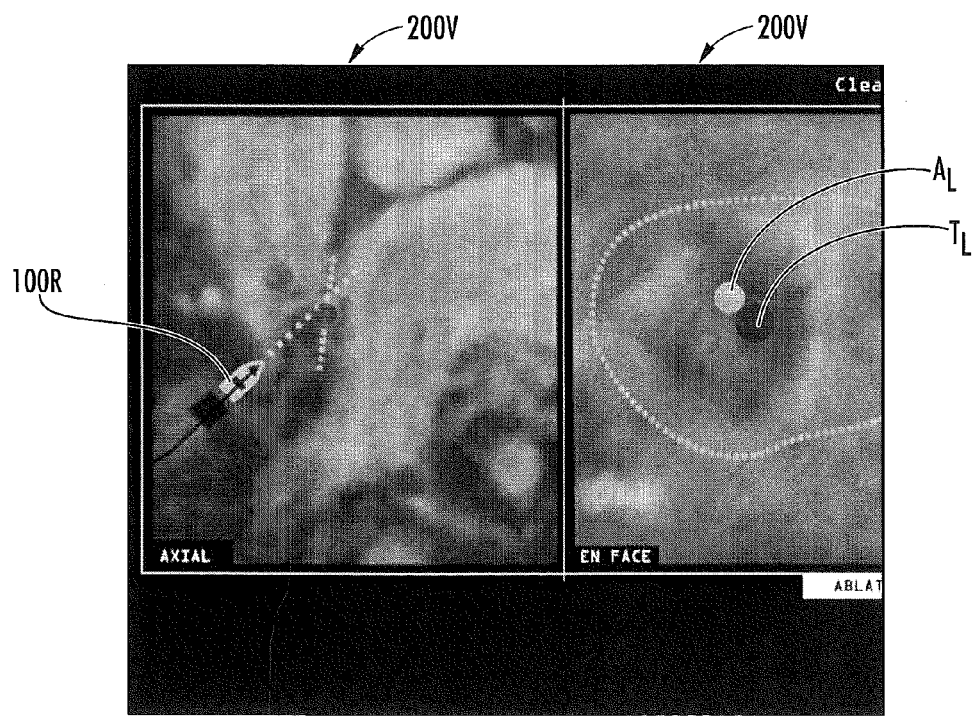
Figure 29D:
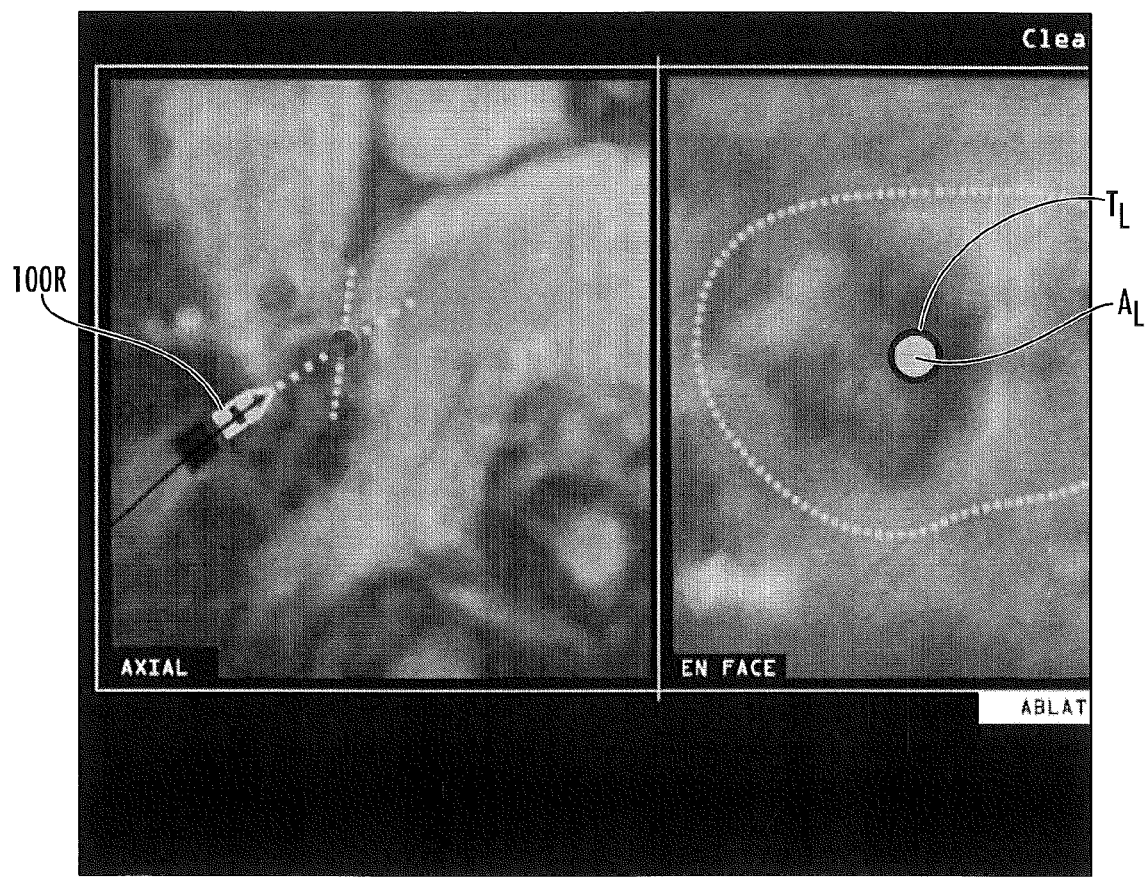

FIGS. 29A-29G illustrate side by side windows displaying visualizations 200v of local tissue rendered by system 10 (FIG. 1) in axial and en face views. A physical representation 100R of the septal puncture device 100 (including physical representations 120R and 130R of the dilator 120 and needle 130) is rendered in the left window, along with a rendering of the target location $T_L$ for puncturing a septal wall. In the right window, the relative location of the target location $T_L$ and the actual location $A_L$ of the distal end 100a of the device 100 are rendered. FIGS. 29A-29C illustrate movement of the device 100 closer to the target location $T_L$, and FIG. 29D illustrates the actual location $A_L$ of distal end portion 100a of the device 100 at the target location $T_L$.

Figure 29E:
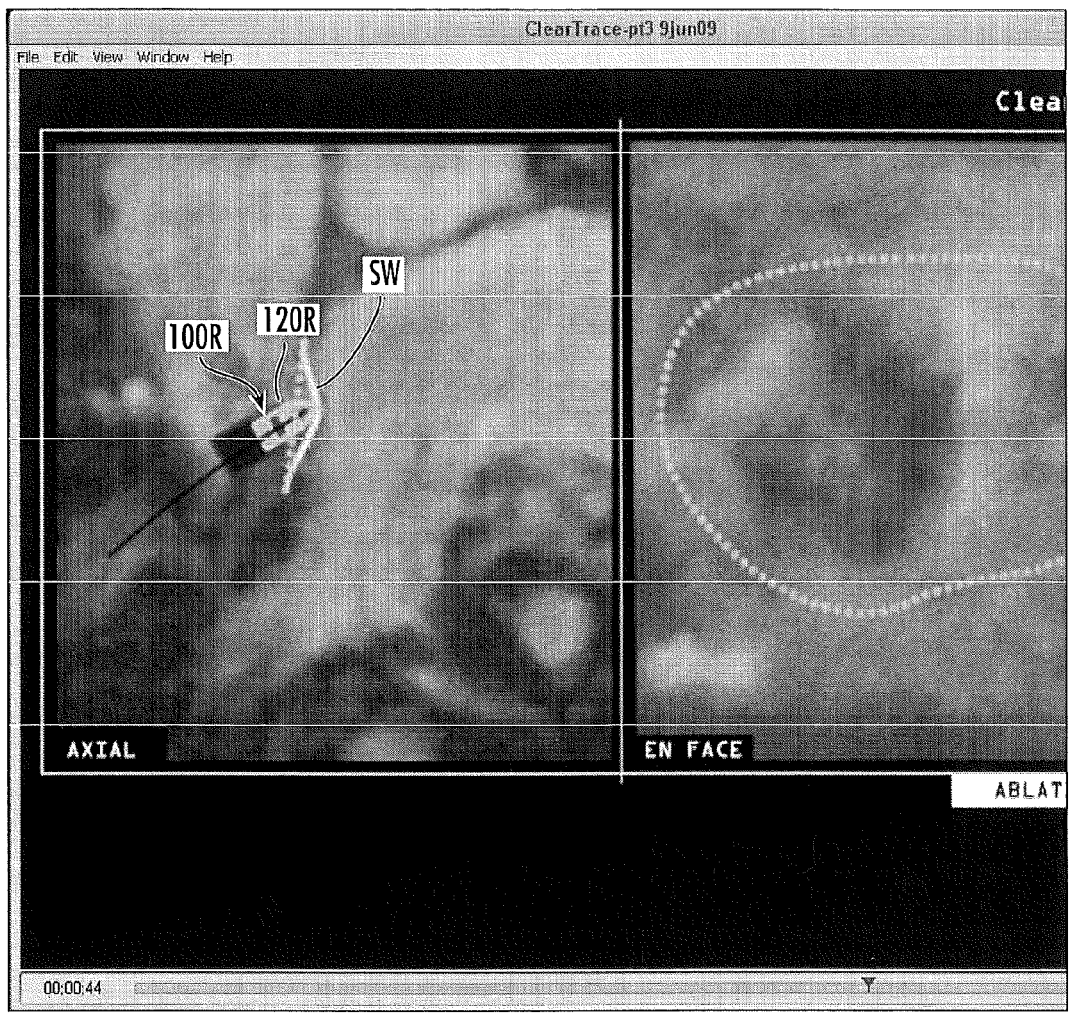
Figure 29F:
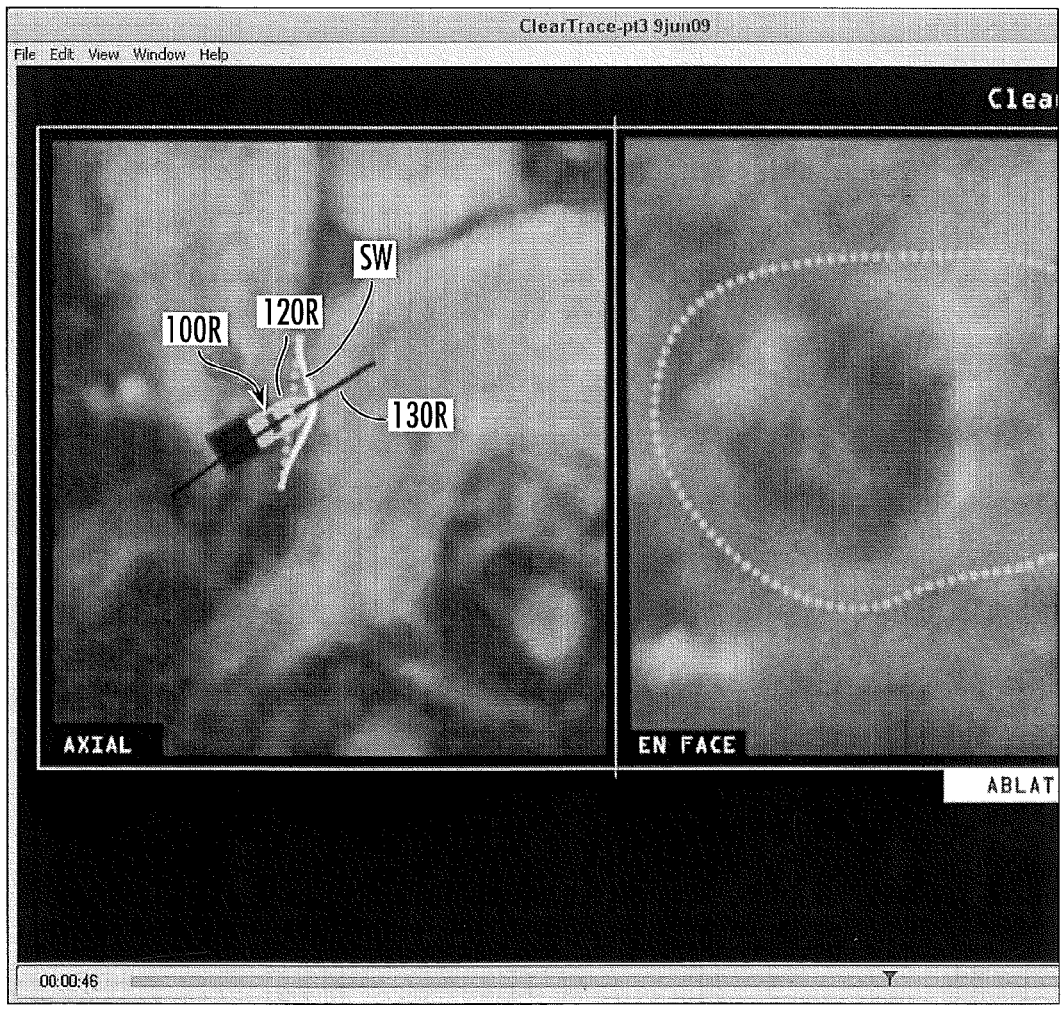
Figure 29G:
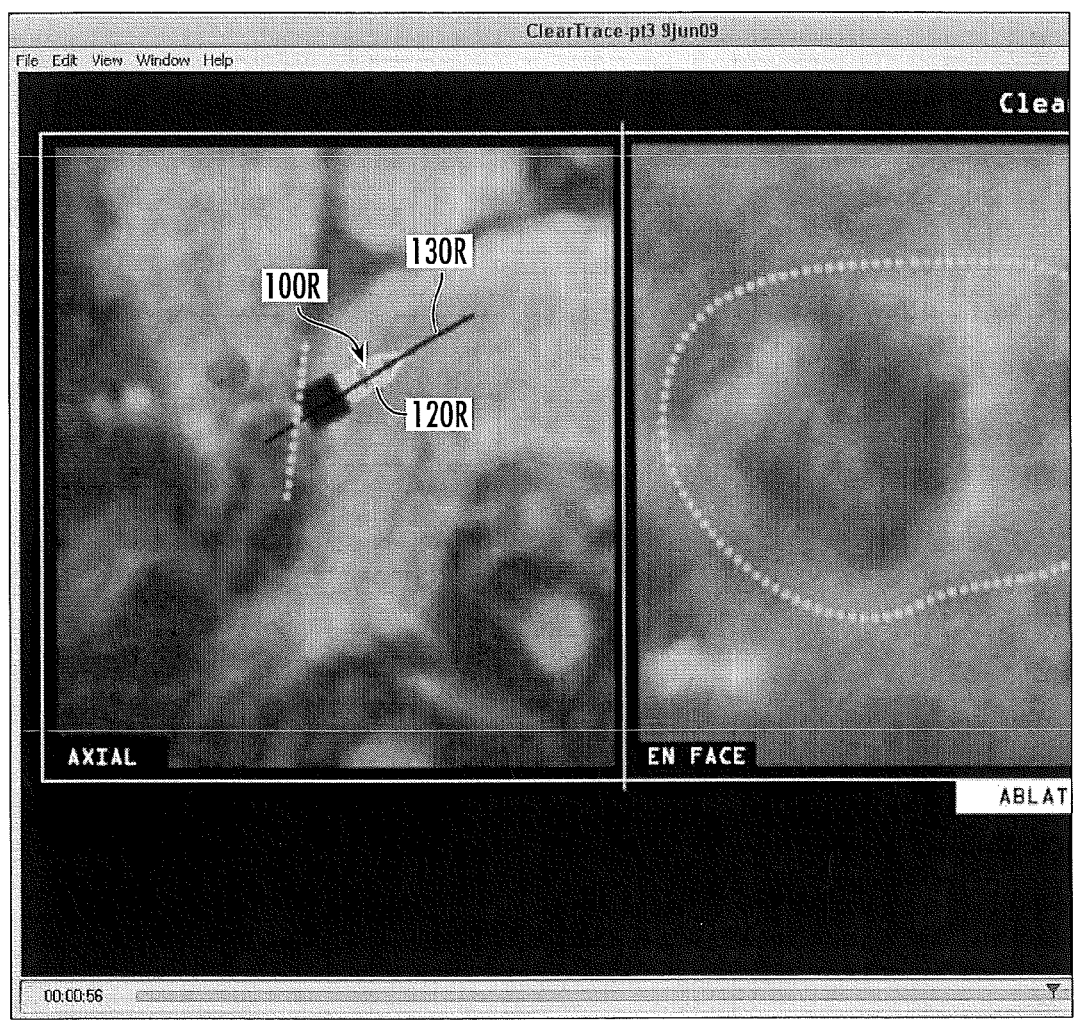

In FIG. 29E, the dilator distal end 120a of the device 100 is pushing against the septal wall tissue SW at the target location $T_L$. The septal wall tissue SW may be tented to show that it is being pushed on. In FIG. 29F, the needle 130 of the device 100 punctures the septal wall tissue SW. (130R is the physical representation of the needle 130.) In some embodiments, a dye may be injected into the left atrium to facilitate MR visibility of the tissue associated therewith. In FIG. 29G, the dilator distal end 120a is moved through the septal wall tissue SW into the left atrium of the heart.

In some particular embodiments, during navigation mode, the device 100 can be visualized using a different pulse sequence from that used in a high-resolution ablation mode, such as, for example, an RT MRI sequence using GRE or SSFP (e.g., TrueFISP) pulse sequence with about 5.5 fps), the tracking coils 150 can be used for spatial orientation and positioning. Typical scan parameters for (near) real-time include: echo time (TE) 1.5 ms, repetition time (TR) 3.5 ms, flip angle 12 degrees, slice thickness 5 mm, resolution 1.8 mm×2.4 mm, parallel imaging with reduction factor (R) of 2.

Once the device position is deemed appropriate (using tracking coils 150), a pulse sequence at the associated scan plane can be used to generate high resolution visualization of the dilator distal end 120a and (myocardial) tissue interface. For example, a T1-weighted 3D FLASH sequence (T1w FLASH) as noted above. Myocardial or other target tissue images during ablation or other therapy can be acquired using an Inner Volume Acquisition (IVA) dark-blood prepared T2-weighted HASTE (T2w HASTE) or dark-blood prepared Turbo Spin Echo (TSE) sequence. Examples of HASTE and TSE sequence parameters include: TE=79 ms/65 ms, TR=3 heart beats, 3 contiguous slices with thickness of about 4 mm, resolution 1.25 mm×1.78 mm/1.25 mm×1.25 mm, fat saturation using SPAIR method, and parallel imaging with R=2, respectively.

Typical heart beat rates and free breathing can present imaging challenges. In some embodiments, (near) RT navigation imaging slices (e.g., GRE pulse sequence at 5.5 fps) can be aligned with high-resolution tissue interface slices (e.g., T1w FLASH) for visualization of the device-tissue interface.

In some embodiments, slices acquired with different sequences can be interlaced to provide an interactive environment for device 100 visualization and lesion delivery, a GUI can allow a user to toggle between these views or can alternate the views based on these image slices or navigation versus ablation or interventional modes/views.

FIG. 30 illustrates one particular embodiments using a cardiac MRI Interventional suite 19 with an integrated cable management system that connects multiple patient connected leads that remain in position even when a patient is translated in or out of a magnet bore on the gantry 16 (the magnet can be an open face or closed magnet configuration) to allow a clinician direct access to a patient. The other ends of the leads connect to power sources, monitors and/or controls located remote from the patient (typically in the control room not the magnet room). As shown in FIG. 30, the MRI interventional suite 19 can include an IV pole 240 (typically attached to the scanner table/gantry 16) and a connection block 250 of cables 200n that are routed through a ceiling (e.g., they extend up, through and above a ceiling) (where "n" is typically between about 1-400, typically between about 5-100), that connect to patch bay 235 and/or 237. Cabling 210n for anesthesia cart 260 can also be routed through the ceiling (where n is typically between about 1-400, typically between about 5-100). The cabling 200n, 210n extends through the ceiling between the rooms 10a, 10b and can connect to the remote devices 500 through a patch panel 250. In some embodiments foot pedal cabling 220n can extend through a floor trough to the patch panel/second room 10b as well (where "n" is typically between about 1-100 cables). For additional description of an exemplary cardiac suite, see, U.S. patent application Ser. No. 12/708,773, the contents of which are hereby incorporated by reference as if recited in full herein. The cables may also alternately be routed under, on or over the floor, suspended on walls, employ wireless connections and the like (and combinations of same).

The system 10 can include a monitoring circuit that can automatically detect which devices are connected to the patient patch bay. One way this can be achieved is by using ID resistors in the patch bay and/or interface as well as in various devices that connect thereto. The MRI scanner computer or processor or the clinician workstation module or processor can monitor resistors via connections CON1, CON2 and CON3. The devices 80 (FIG. 1) can have built-in resistors that modify the resistance by lines that connect to CON1, CON2 and CON3. Variation in resistance values helps the monitor which device is connected. Once that determination is made the scanner may automatically load special acquisition parameters, display parameters and update the progress of the procedure to display on the display 20 such as at workstation 60 (FIG. 3), for example.

Electrical isolation between the MR Scanner 10S and the device 80 can be provided via low pass filters inside and outside the MRI suite. As is known to those of skill in the art, components in the MRI Suite can be connected to external components using a waveguide built into the RF shield that encloses the MRI suite. The ablation catheter 80 can be connected to an appropriate energy source, such as, for example, a Stockert 70 RF generator (Biosense Webster, Diamond Bar, Calif., USA) with MR compatible interface circuits configured for 3 T magnetic fields (where a 3 T system is used). The system can comprise an EP Suite with a Siemens Verio system (Siemens Healthcare, Erlangen, Germany) or other suitable scanner as well as suitable external imaging coils, such as spine and/or body array coils as is known to those of skill in the art.

Embodiments of the present invention may be utilized in conjunction with navigation and mapping software features. For example, current and/or future versions of devices and systems described herein may include features with adaptive projection navigation and/or 3-D volumetric mapping technology, the latter may include aspects associated with U.S. patent application Ser. No. 10/076,882, which is incorporated herein by reference in its entirety.

Figure 31A:
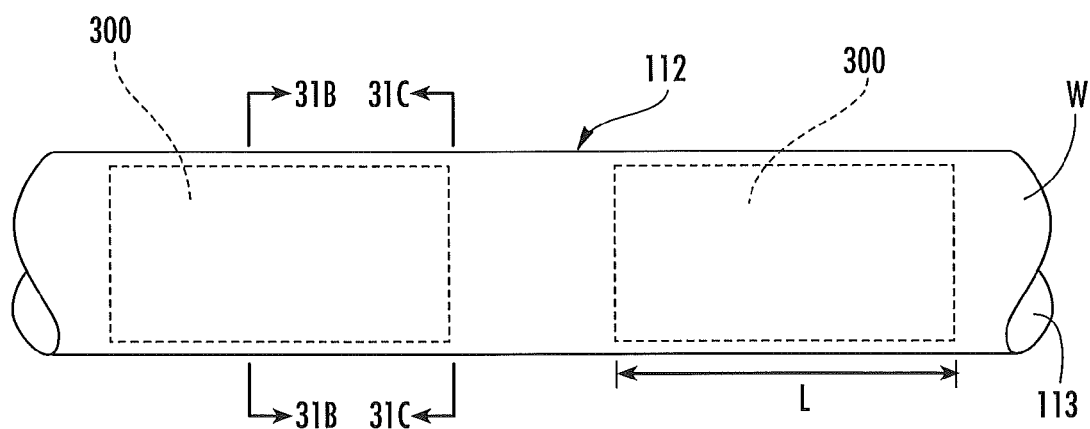
FIG. 31A is a partial side view of the sheath of the device of FIG. 4 including multiple RF shields in end-to-end spaced-apart relationship, according to some embodiments of the present invention.
Figure 31B:
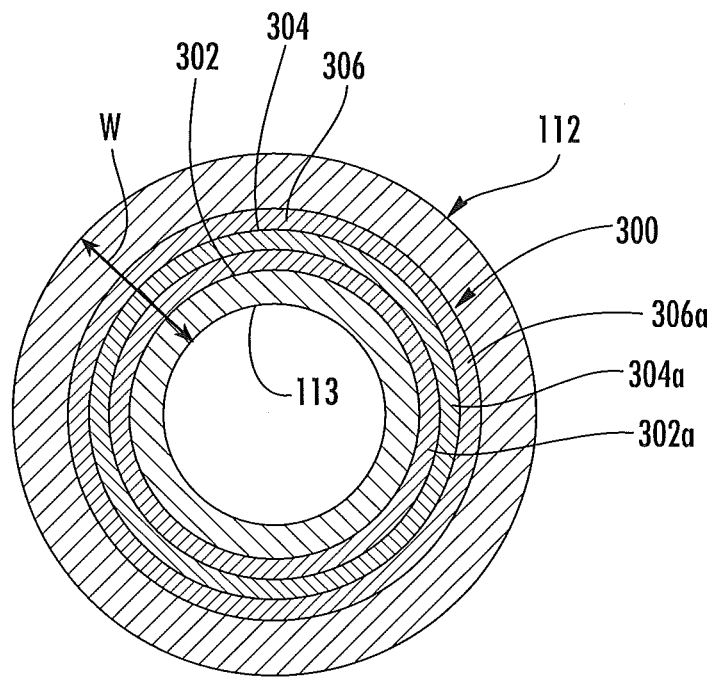
FIG. 31B is a cross-sectional view of the sheath of FIG. 31A taken along line 31B-31B.
Figure 31C:
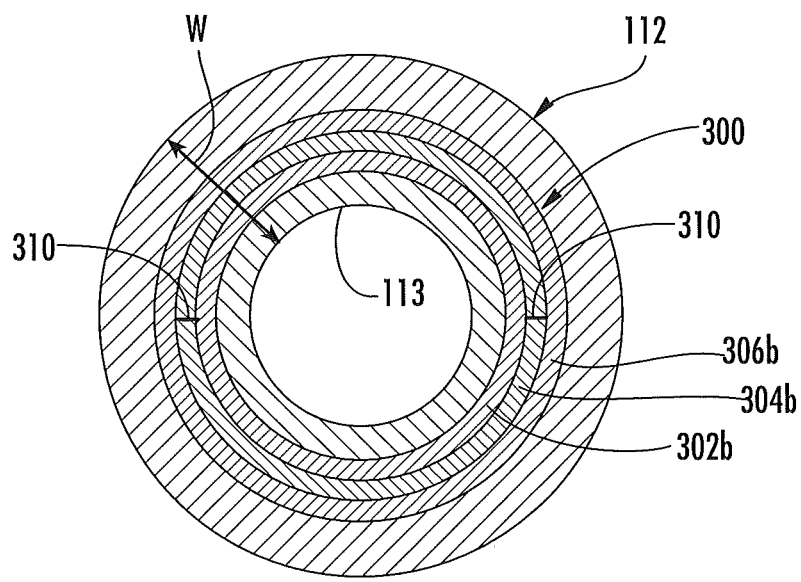
FIG. 31C is a cross-sectional view of the sheath of FIG. 31A taken along line 31C-31C.

Referring now to FIGS. 31A-31C, the sheath 112 of the septal puncture device 100 of FIGS. 4-7 may include a plurality of RF shields 300 coaxially disposed within the wall W of the sheath 112 in end-to-end spaced-apart relationship. The RF shields 300 are configured to impede RF coupling along the dilator 120 and/or needle 130 inserted within the sheath 112 when exposed to an MRI environment. Although a pair of RF shields 300 are illustrated in FIG. 31A, it is understood that many additional RF shields 300 may be coaxially disposed within the elongated sheath wall W in end-to-end spaced-apart relationship. Only two RF shields 300 are shown for ease of illustration.

The RF shields 300 are configured to completely surround the central lumen 113 of the sheath 112. As more clearly shown in FIGS. 31B-31C, each RF shield 300 includes an elongated inner tubular conductor 302 having opposite end portions 302a, 302b, an elongated dielectric layer 304 that coaxially surrounds the inner conductor 302, and an elongated outer tubular conductor 306 that coaxially surrounds the dielectric layer 304 and has opposite end portions 306a, 306b. The inner and outer tubular conductors 302, 306 are electrically connected to each other at only one of the end portions. The opposite respective end portions are electrically isolated. In the illustrated embodiment, the inner and outer tubular conductors 302, 306 are electrically connected to each other via jumper wires 310 at adjacent end portions 302b, 306b (FIG. 31C).

In some embodiments, the inner and outer conductors can be formed as thin-film foil layers of conductive material on opposite sides of a thin film insulator (e.g., a laminated, thin flexible body).

The RF shields 300 are spaced-apart sufficiently to allow articulation of the sheath 112 and without any stiff points. In some embodiments, adjacent RF shields 300 may be spaced-apart between about 0.1 inches and about 1.0 inches.

By electrically connecting (i.e., shorting) the inner and outer tubular conductors 302, 306 at only one end and not attaching the conductors to ground, each RF shield 300 serves as a quarter-wave resonant choke that forms an effective parallel resonance circuit at a frequency of interest and/or generates high impedance at the inner shield at the location not shorted. Each RF shield 300 impedes the formation of resonating RF waves along conductive members, such as electrical leads and, thus, the transmission of unwanted RF energy along the dilator 120 and/or needle 130 at such frequency.

Each of the illustrated RF shields 300 can be tuned to a particular frequency by adjusting the length L of the RF shield 300 and/or the thickness of the dielectric layer 304. Typically, the length L of RF shield 300 is about twenty inches (20") or less. However, the RF shield 300 is not limited to a particular length.

While embodiments have been primarily discussed with respect to an MRI-guided cardiac system, the system can be used for other anatomical regions and deliver or apply other therapies as well as for diagnostic procedures. For example, the esophagus and anatomy near the esophagus, e.g., the aorta, coronary arteries, mediastinum, the hepaticobiliary system or the pancreas in order to yield anatomic information about the structures in those areas, "pancreaticohepaticobiliary" structures (collectively the structures of the liver, gallbladder, bile ducts and pancreas), the tracheobronchopulmonary structure (structures including the lungs and the tracheobronchial tree), the nasopharynx system (e.g., a device introduced transnasally may be adapted for evaluating the arterial circle of Willis and related vascular structures for abnormalities, for example congenital or other aneurysms), the proximal aerodigestive system or the thyroid, the ear canal or the Eustachian tube, permitting anatomic assessment of abnormalities of the middle or inner ear, and further permitting evaluation of adjacent intracranial structures and lesions.

The systems and methods of the present invention may be particularly useful in those lesions whose extent is not readily diagnosed, such as basal cell carcinomas. These lesions may follow nerves into the orbit or into the intracranial area, extensions not evident with traditional imaging modalities to the surgeon undertaking the resection to provide real time information to the resecting surgeon or the surgeon performing a biopsy as to the likely areas of lymph node invasion.

It is also contemplated that the systems can be used in the "head and neck" which refers collectively to those structures of the ear, nose and throat and proximal aerodigestive system as described above, traditionally falling within the province of otorhinolaryngology. The term "head and neck," as used herein, will further include those structures of the neck such as the thyroid, the parathyroid, the parotid and the cervical lymph nodes, and will include also the extracranial portions of the cranial nerves, including but not limited to the facial nerve, this latter nerve being included from its entry into the internal auditory meatus outward. The term "head and neck, as used herein, will also include those structures of the orbit or of the globe, including the oculomotor muscles and nerves, lacrimal glands and adnexal structures. As used herein, the term "head and neck" will further include those intracranial structures in proximity to the aforesaid head and neck structures. These intracranial structures may include, as examples, the pituitary gland, the pineal gland, the nuclei of various cranial nerves, the intracranial extensions of the cranial nerves, the cerebellopontine angle, the arterial circle of Willis and associated vascular structures, the dura, and the meninges.

In yet other embodiments, the systems can be used in the genourinary system, such as the urethra, prostate, bladder, cervix, uterus, and anatomies in proximity thereto. As used herein, the term "genitourinary" shall include those structures of the urinary tract, the male genital system and the female genital system. The urinary tract structures include the urethra, the bladder, the ureters, the kidney and related neural, vascular, lymphatic and adnexal structures. The male genital tract includes the prostate, the seminal vesicles, the testicles, the epididymis and related neural, vascular, lymphatic, ductal and adnexal structures. The female genital tract includes the vagina, the cervix, the non-gravid and gravid uterus, the fallopian tubes, the ovaries, the ova, the fertilized egg, the embryo and the fetus. The term "genitourinary" further refers to those pelvic structures that surround or support the above-mentioned structures, such as the paraurethral tissues, the urogenital diaphragm or the musculature of the pelvic floor. The devices can be configured for transurethral placement for evaluation and treatment of female urinary incontinence or bleeding and may use high resolution images of the local tissue, e.g., different layers of the paraurethral tissues. It is understood, for example, that a clearly identified disruption in the muscle layers surrounding the urethra may be repaired surgically, but also must be guided by detailed anatomic information about the site of the abnormality. The devices may also be configured for placement in the genitourinary system such as into the ureter or renal pelvis, urinary tract, or transvaginal use in analysis of the vagina and anatomies in proximity thereto. For example, transvaginal or transcervical endouterine placement may be useful in the diagnosis of neoplasia, in the diagnosis and treatment of endometriosis and in the evaluation of infertility or diagnosis, treatment of pelvic disorders resulting in pelvic pain syndromes, evaluation/treatment of cervical and uterine malignancies and to determine their stages, obstetric use such as permitting anatomic evaluation of mother and fetus.

In another embodiment, the systems can be used for evaluating and/or treating the rectum or colon, typically by the transrectal route that can be inserted through the anus to a level within the rectum, sigmoid or descending colon where the designated anatomy can be visualized. For example, this approach may be used to delineate the anatomy of the prostate gland, and may further guide the biopsy or the extirpation of lesions undertaken transrectally or transurethrally.

In other embodiments, the systems and methods of the present invention may be used for the evaluation, diagnosis or treatment of a structure in the gastrointestinal system, or for the evaluation, diagnosis or treatment of a region of the gastrointestinal anatomy. As used herein, the term "gastrointestinal" shall include structures of the digestive system including the esophagus, the stomach, the duodenum, jejunum and ileum (small intestine), the appendix and the colon. The term "gastrointestinal anatomy" shall refer to the structures of the gastrointestinal system as well as the surrounding supporting structures such as the mesentery and the enclosing structures such as the peritoneum, the diaphragm and the retroperitoneum. Disorders of the gastrointestinal system are well-known in the medical arts, as are disorders of the gastrointestinal anatomy. In an exemplary embodiment, the intrabody device may be passed into the stomach.

In other embodiments, the systems and methods of the present invention may be used for the evaluation, diagnosis and treatment of the vascular system. The vascular system is understood to include the blood vessels of the body, both arterial and venous. The vascular system includes both normal and abnormal blood vessels, named and unnamed vessels, and neovascularization. Access to the vascular system takes place using techniques familiar to practitioners of ordinary skill in the art. The present invention may be used in blood vessels of all size and the intrabody devices may be dimensionally adapted to enter smaller caliber vessels, such as those comprising the distal coronary circulation, the intracranial circulation, the circulation of the distal extremities or the distal circulation of the abdominal viscera. According to these systems and methods, furthermore, positioning a device within the vascular system may be useful for evaluating, diagnosing and treating conditions in structures adjacent to or in proximity to the particular vessel within which the device is situated. Such structures are termed "perivascular structures." As an example, a device placed within a coronary artery may provide information about the vessel itself and about the myocardium that is perfused by the vessel or that is adjacent to the vessel. A device thus positioned may be able to guide therapeutic interventions directed to the myocardial tissue, and may also be able to guide endovascular or extravascular manipulations directed to the vessel itself. It will be readily appreciated by those of ordinary skill in the art that a number of other applications exist or may be discovered with no more than routine experimentation using the systems and methods of the present invention within the vascular system.

It is understood that access to anatomic structures using the systems, devices modified to fit the intended purpose and anatomy, and methods of the present invention may be provided via naturally occurring anatomic orifices or lumens, as indicated in the examples above. It is further understood, however, that access to anatomic structures using these systems and methods may be additionally provided using temporary or permanent orifices that have been created medically.

Further, the methods and systems may cooperate with robotic driven systems rather than manual systems.

The aforesaid embodiments are understood to be exemplary only. Other embodiments wherein devices may be used within body areas such as body canals, cavities, lumens, passageways, actual or potential spaces will be apparent to practitioners of ordinary skill in the relevant arts.

Some embodiments of the present invention may take the form of an entirely software embodiment or an embodiment combining software and hardware aspects, all generally referred to herein as a "circuit" or "module." Furthermore, the present invention may take the form of a computer program product on a computer-usable storage medium having computer-usable program code embodied in the medium. Any suitable computer readable medium may be utilized including hard disks, CD-ROMs, optical storage devices, a transmission media such as those supporting the Internet or an intranet, or magnetic storage devices. Some circuits, modules or routines may be written in assembly language or even micro-code to enhance performance and/or memory usage. It will be further appreciated that the functionality of any or all of the program modules may also be implemented using discrete hardware components, one or more application specific integrated circuits (ASICs), or a programmed digital signal processor or microcontroller. Embodiments of the present invention are not limited to a particular programming language.

Computer program code for carrying out operations of data processing systems, method steps or actions, modules or circuits (or portions thereof) discussed herein may be written in a high-level programming language, such as Python, Java, AJAX (Asynchronous JavaScript), C, and/or C++, for development convenience. In addition, computer program code for carrying out operations of exemplary embodiments may also be written in other programming languages, such as, but not limited to, interpreted languages. Some modules or routines may be written in assembly language or even micro-code to enhance performance and/or memory usage. However, embodiments are not limited to a particular programming language. It will be further appreciated that the functionality of any or all of the program modules may also be implemented using discrete hardware components, one or more application specific integrated circuits (ASICs), or a programmed digital signal processor or microcontroller. The program code may execute entirely on one (e.g., a workstation computer or a Scanner's computer), partly on one computer, as a stand-alone software package, partly on the workstation's computer or Scanner's computer and partly on another computer, local and/or remote or entirely on the other local or remote computer. In the latter scenario, the other local or remote computer may be connected to the user's computer through a local area network (LAN) or a wide area network (WAN), or the connection may be made to an external computer (for example, through the Internet using an Internet Service Provider).

Some embodiments of the present invention are described in part with reference to flowchart illustrations and/or block diagrams of methods, apparatus (systems) and computer program products. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer-readable memory that can direct a computer or other programmable data processing apparatus to function in a particular manner, such that the instructions stored in the computer-readable memory produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing some or all of the functions/acts specified in the flowchart and/or block diagram block or blocks.

The flowcharts and block diagrams of certain of the figures herein illustrate exemplary architecture, functionality, and operation of possible implementations of embodiments of the present invention. In this regard, each block in the flow charts or block diagrams represents a module, segment, or portion of code, which comprises one or more executable instructions for implementing the specified logical function(s). It should also be noted that in some alternative implementations, the functions noted in the blocks may occur out of the order noted in the figures. For example, two blocks shown in succession may in fact be executed substantially concurrently or the blocks may sometimes be executed in the reverse order or two or more blocks may be combined, depending upon the functionality involved.

The workstation 60 and/or interface 44, 84, or patch bay, may also include a decoupling/tuning circuit that allows the system to cooperate with an MRI scanner 10S and filters and the like. See, e.g., U.S. Pat. Nos. 6,701,176; 6,904,307 and U.S. Patent Application Publication No. 2003/0050557, the contents of which are hereby incorporated by reference as if recited in full herein.

Figure 33:
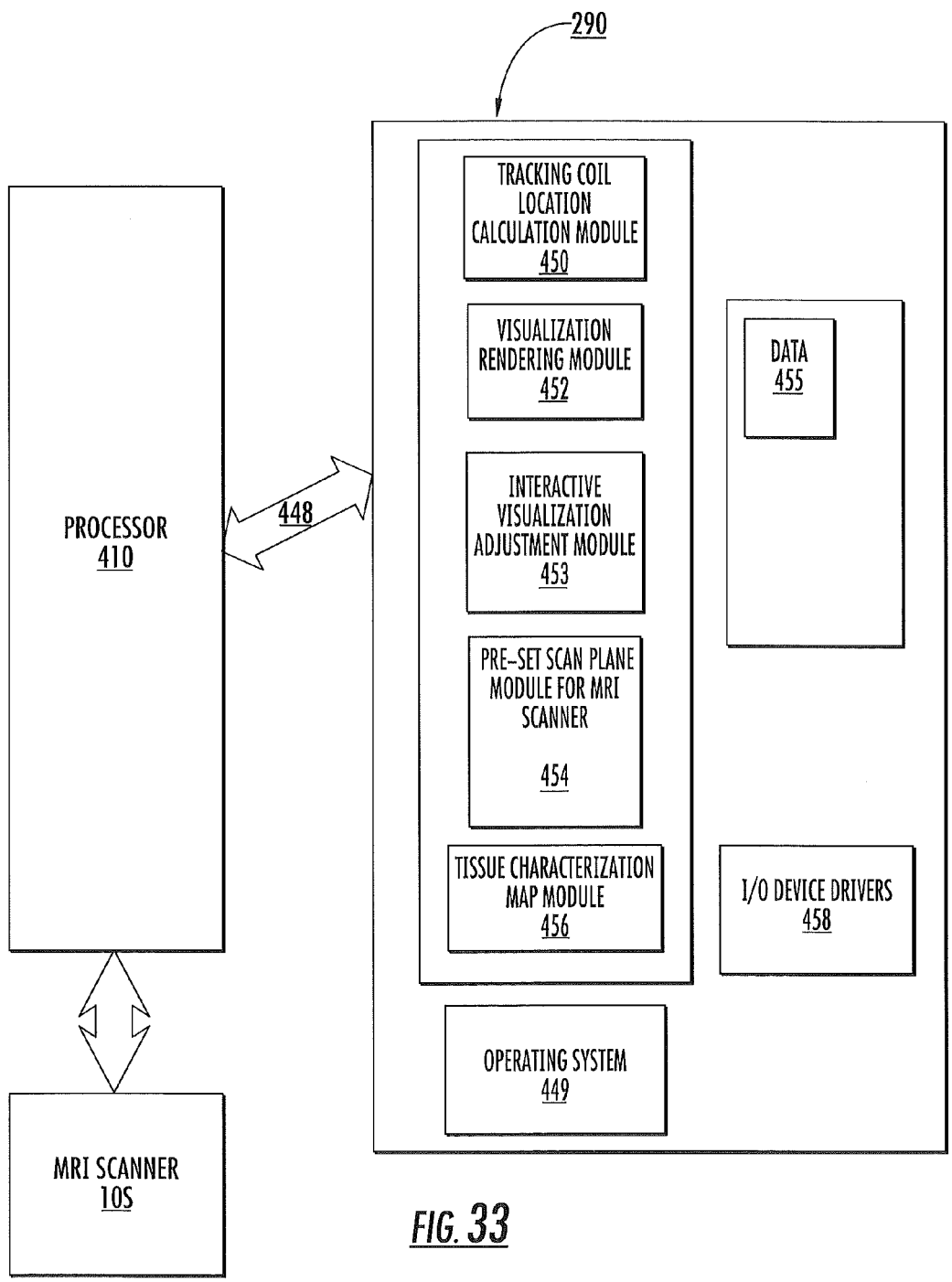
FIG. 33 is a schematic illustration of a data processing circuit or system according to embodiments of the present invention.

FIG. 33 is a schematic illustration of a circuit or data processing system that can be used with the system 10 (FIG. 1). The circuits and/or data processing systems 290 may be incorporated in a digital signal processor in any suitable device or devices. As shown in FIG. 33, the processor 410 communicates with and/or is integral with an MRI scanner 10S and with memory 414 via an address/data bus 448. The processor 410 can be any commercially available or custom microprocessor. The memory 414 is representative of the overall hierarchy of memory devices containing the software and data used to implement the functionality of the data processing system. The memory 414 can include, but is not limited to, the following types of devices: cache, ROM, PROM, EPROM, EEPROM, flash memory, SRAM, and DRAM.

FIG. 33 illustrates that the memory 414 may include several categories of software and data used in the data processing system: the operating system 449; the application programs 454; the input/output (I/O) device drivers 458; and data 456. The data 456 can also include device (ablation catheter) dimensions (e.g., distance of a tracking coil to the tip) and patient-specific image data 455. FIG. 33 also illustrates the application programs 454 can include a Tracking Coil Location Identification Calculation Module 450, a Visualization Rendering Module 452, an Interactive Visualization (and UI) Module 453, a Tissue Characterization Map Module 456, and a Pre-Set Scan Plane to Target Ablation Site Module 454, a and a UI Interface Module 453. As will be appreciated by those of skill in the art, the operating systems 449 may be any operating system suitable for use with a data processing system, such as OS/2, AIX, or z/OS from International Business Machines Corporation, Armonk, N.Y., Windows CE, Windows NT, Windows95, Windows98, Windows2000, WindowsXP, Windows Visa, Windows7, Windows CE or other Windows versions from Microsoft Corporation, Redmond, Wash., Palm OS, Symbian OS, Cisco IOS, VxWorks, Unix or Linux, Mac OS from Apple Computer, LabView, or proprietary operating systems. For example, VxWorks which can run on the Scanner's sequence generator for precise control of pulse sequence waveform timings.

The I/O device drivers 458 typically include software routines accessed through the operating system 449 by the application programs 454 to communicate with devices such as I/O data port(s), data storage 456 and certain memory 414 components. The application programs 454 are illustrative of the programs that implement the various features of the data processing system and can include at least one application, which supports operations according to embodiments of the present invention. Finally, the data 456 represents the static and dynamic data used by the application programs 454, the operating system 449, the I/O device drivers 458, and other software programs that may reside in the memory 414.

While the present invention is illustrated, for example, with reference to the Modules 450, 452, 453, 454, 456 being application programs in FIG. 33, as will be appreciated by those of skill in the art, other configurations may also be utilized while still benefiting from the teachings of the present invention. For example, the Modules and/or may also be incorporated into the operating system 449, the I/O device drivers 458 or other such logical division of the data processing system. Thus, the present invention should not be construed as limited to the configuration of FIG. 33 which is intended to encompass any configuration capable of carrying out the operations described herein. Further, one or more of modules, i.e., Modules 450, 452, 453, 454, 456 can communicate with or be incorporated totally or partially in other components, such as separate or a single processor, an MRI scanner 10S or workstation 60.

The I/O data port can be used to transfer information between the data processing system, the workstation, the MRI scanner, and another computer system or a network (e.g., the Internet) or to other devices controlled by the processor. These components may be conventional components such as those used in many conventional data processing systems, which may be configured in accordance with the present invention to operate as described herein.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the teachings and advantages of this invention. Accordingly, all such modifications are intended to be included within the scope of this invention as defined in the claims. The invention is defined by the following claims, with equivalents of the claims to be included therein.

That which is claimed is:

1. An MRI-compatible medical device, comprising:
    an elongated sheath having a distal end, an opposite proximal end, and a central lumen extending between the proximal and distal ends, wherein the sheath includes at least one tracking member adjacent the sheath distal end;
    a dilator movably disposed within the sheath lumen and having a distal end, an opposite proximal end, and a lumen extending between the dilator proximal and distal ends, wherein the dilator includes at least one tracking member adjacent the dilator distal end, wherein the at least one tracking member includes a cable configured to electrically connect the at least one tracking member to an MRI scanner, and wherein the dilator distal end is configured to extend outwardly from the sheath distal end; and
    a needle movably disposed within the dilator lumen and having a distal end, an opposite proximal end, and a central lumen extending between the needle proximal and distal ends, wherein the needle comprises a main body portion of an MRI-compatible material and a tip portion, wherein the tip portion is located at the needle distal end, wherein the needle is movable between retracted and extended positions, wherein the needle distal end is within the dilator lumen when in the retracted position and wherein the needle distal end extends outwardly from the dilator distal end when in the extended position, wherein the needle tip portion includes a tracking member that is closely spaced-apart from the at least one tracking member on the dilator distal end when the needle is in the extended position.

2. The device of claim 1, wherein a portion of the sheath adjacent the sheath distal end has a generally curved configuration.

3. The device of claim 1, wherein the at least one tracking member adjacent the sheath distal end comprises a coating of MRI visible material on the sheath.

4. The device of claim 1, wherein the at least one tracking member adjacent the sheath distal end comprises at least one RF coil.

5. The device of claim 1, wherein the at least one tracking member adjacent the dilator distal end comprises at least one RF coil.

6. The device of claim 1, wherein the at least one tracking member adjacent the dilator distal end comprises a pair of RF coils in adjacent spaced-apart relationship.

7. The device of claim 5, wherein the at least one RF coil adjacent the dilator distal end is embedded within a wall of the dilator.

8. The device of claim 1, wherein the needle tip portion comprises multiple sections of conductive and non-conductive material alternately connected together.

9. The device of claim 1, wherein the needle tip portion comprises a plurality of sections of different diameters arranged in a telescopic configuration.

10. The device of claim 1, wherein the needle tip portion comprises a coating of material.

11. The device of claim 1, wherein a portion of the needle adjacent the needle distal end has a generally curved configuration.

12. The device of claim 1, wherein the needle tip portion is deformable.

13. The device of claim 1, further comprising a guidewire having a distal end, and an opposite proximal end, wherein the guidewire includes at least one tracking member adjacent the guidewire distal end, and wherein the guidewire is configured to be movably disposed within the dilator lumen when the needle is absent therefrom.

14. An MRI-compatible medical device, comprising:
    an elongated sheath having a distal end, an opposite proximal end, and a central lumen extending between the proximal and distal ends, wherein the sheath includes at least one tracking member adjacent the sheath distal end;
    a dilator movably disposed within the sheath lumen and having a distal end, an opposite proximal end, and a lumen extending between the dilator proximal and distal ends, wherein the dilator includes at least one tracking member adjacent the dilator distal end, wherein the at least one tracking member includes a cable configured to electrically connect the at least one tracking member to an MM scanner, and wherein the dilator distal end is configured to extend outwardly from the sheath distal end; and
    a needle movably disposed within the dilator lumen and having a distal end, an opposite proximal end, and a central lumen extending between the needle proximal and distal ends, wherein the needle comprises a main body portion of an MM-compatible material and a tip portion, wherein the tip portion is located at the needle distal end, wherein the needle is movable between retracted and extended positions, wherein the needle distal end is within the dilator lumen when in the retracted position and wherein the needle distal end extends outwardly from the dilator distal end when in the extended position.

15. The device of claim 14, wherein the needle tip portion includes a tracking member that is closely spaced-apart from the at least one tracking member on the dilator distal end when the needle is in the extended position.

16. The device of claim 14, wherein the at least one tracking member adjacent the sheath distal end comprises a coating of MM visible material on the sheath.

17. The device of claim 14, wherein the at least one tracking member adjacent the sheath distal end comprises at least one RF coil.

18. The device of claim 14, wherein the at least one tracking member adjacent the dilator distal end comprises at least one RF coil.

19. The device of claim 14, wherein the at least one tracking member adjacent the dilator distal end comprises a pair of RF coils in adjacent spaced-apart relationship.

* * * * *

UNITED STATES PATENT AND TRADEMARK OFFICE
CERTIFICATE OF CORRECTION

PATENT NO. : 8,768,433 B2  
APPLICATION NO. : 13/723612  
DATED : July 1, 2014  
INVENTOR(S) : Jenkins et al.

Page 1 of 1

It is certified that error appears in the above-identified patent and that said Letters Patent is hereby corrected as shown below:

In the Specification:
Column 12, Line 20: Please begin a new paragraph after "MRI image." in line 20 so that it reads as:
-- MRI image.
   The system 10 can include --

Column 28, Line 47: Please begin a new paragraph after "Module 453." in line 47 so that it reads as:
-- Module 453.
   As will be appreciated --

In the Claims:
Column 30, Claim 14, Line 56: Please correct "an MM scanner,"
   to read -- an MRI scanner, --

Column 30, Claim 14, Line 63: Please correct "an MM-compatible material"
   to read -- an MRI-compatible material --

Column 31, Claim 16, Line 10: Please correct "of MM visible"
   to read -- of MRI visible --

Signed and Sealed this
Thirtieth Day of December, 2014

Michelle K. Lee
*Deputy Director of the United States Patent and Trademark Office*